United States Patent
Schmitt et al.

(10) Patent No.: US 7,329,663 B2
(45) Date of Patent: Feb. 12, 2008

(54) SUBSTITUTED-TRIAZOLOPYRIMIDINES AS ANTICANCER AGENTS

(75) Inventors: Mark R. Schmitt, Trenton, NJ (US); Donald R. Kirsch, Princeton, NJ (US); Jane E. Harris, Pennington, NJ (US); Carl F. Beyer, Chester, NY (US); Klaus-Jüergen Pees, Mainz (DE); Paul A. Carter, Biberach an der Riss (DE); Waldemar Pfrengle, Siebersbach (DE); Guido Albert, Hackenheim (DE)

(73) Assignee: Wyeth, Madison, NJ (US)

( * ) Notice: Subject to any disclaimer, the term of this patent is extended or adjusted under 35 U.S.C. 154(b) by 343 days.

(21) Appl. No.: 09/895,975

(22) Filed: Jun. 29, 2001

(65) Prior Publication Data
US 2002/0068744 A1   Jun. 6, 2002

Related U.S. Application Data

(60) Provisional application No. 60/215,585, filed on Jun. 30, 2000.

(51) Int. Cl.
*A61K 31/519* (2006.01)
*C07D 487/04* (2006.01)

(52) U.S. Cl. .................. 514/259.31; 544/263

(58) Field of Classification Search ........... 514/259.31, 514/228.2, 233.2; 544/254, 61, 111, 263
See application file for complete search history.

(56) References Cited

U.S. PATENT DOCUMENTS

| | | | |
|---|---|---|---|
| 4,444,774 A | | 4/1984 | Dusza et al. |
| 5,387,747 A * | | 2/1995 | Bru-Magniez et al. ... 514/233.2 |
| 5,753,665 A * | | 5/1998 | Sargent et al. ......... 514/259.31 |
| 5,854,252 A * | | 12/1998 | Pees et al. ............. 514/259.31 |
| 5,869,486 A * | | 2/1999 | Lee et al. .................... 514/248 |
| 5,948,783 A * | | 9/1999 | Pees et al. ............. 514/259.31 |
| 5,994,360 A * | | 11/1999 | Pfrengle ................ 514/259.31 |
| 6,001,830 A * | | 12/1999 | Lee et al. .................... 514/248 |
| 6,020,338 A * | | 2/2000 | Pfrengle et al. ........ 514/259.31 |
| 6,114,338 A * | | 9/2000 | Lee et al. ............... 514/210.21 |
| 6,117,876 A * | | 9/2000 | Pees et al. ............. 514/259.31 |
| 6,165,940 A * | | 12/2000 | Aven ......................... 504/118 |
| 6,255,309 B1 * | | 7/2001 | Pees et al. .................. 514/256 |
| 6,297,251 B1 * | | 10/2001 | Pees et al. ............. 514/259.31 |
| 6,369,065 B1 * | | 4/2002 | Chatelain et al. ...... 514/259.31 |
| 6,380,202 B1 * | | 4/2002 | Pees et al. ............. 514/259.31 |
| 2004/0063687 A1 * | | 4/2004 | Atwal et al. ........... 514/214.01 |
| 2004/0142943 A1 * | | 7/2004 | Gebauer et al. ........ 514/259.31 |
| 2004/0157863 A1 * | | 8/2004 | Gebauer et al. ........ 514/259.31 |
| 2004/0171541 A1 * | | 9/2004 | Olsson et al. ................. 514/12 |
| 2004/0176398 A1 * | | 9/2004 | Gebauer et al. ........ 514/259.31 |
| 2005/0090508 A1 * | | 4/2005 | Zhang et al. ........... 514/259.31 |
| 2007/0060597 A1 * | | 3/2007 | Qi et al. ................. 514/259.31 |

FOREIGN PATENT DOCUMENTS

| | | |
|---|---|---|
| DE | 55956 A | 5/1967 |
| DE | 61269 A | 4/1968 |
| EP | 0305093 A | 3/1989 |
| FR | 2784380 A | 4/2000 |
| JP | 56110620 | 11/1981 |
| JP | 02212488 | 8/1990 |

OTHER PUBLICATIONS

H.P. Hsieh et al, Bioorganic and Chemistry Letters, 13, 101-105 (2003).
Park et al, International Journal of Oncology, 20(2), 333-338 (2002).
Gerald Bacher et al, Cancer Research, 61, 392-399, Jan. 1, 2001.
M. Iwahana et al, Anticancer research 20(2A), 785-92 (Mar.-Apr. 2000).
Richard J. Bleicher et al, Cancer Letters, 150, 129-135 (2000).
Qian Cheng, et al, Bioorganic and Medicinal Chemistry Letters, 10, 517-521, (2000).
Ke. Chen et al, J.Med.Chem. 1997, 40, 3049-3056.
(Trock B. J., Leonessa F., Clarke R. Multidrug resistance in breast cancer: a meta-analysis of MDR1/gp170 expression and its possible functional significance. J. Natl. Cancer Inst. (Bethesda), 89: 917-931, 1997).
N. Koyanagi et al, Cancer Research, 54(7), 1702-6 (Apr. 1, 1994).
A.P. Novikova, et al., Khim-Farm. ZH., vol. 15, No. 4, 1981, pp. 31-35.
A.P. Novikova, et al., Khim-Farm. ZH, vol. 15, No. 4, 1981, pp. 31-35, English Abstract.
T. Okabayashi, Chem. Pharm. Bull., vol. 8, No. 2, 1960, pp. 162-167.
M. Suiko, et al., Sgric. Biol. Chem., vol. 41, No. 10, 1977, pp. 2047-2053.
PCT International Search , PCT/USO1/20672, Jul. 31, 2002.

* cited by examiner

*Primary Examiner*—James O. Wilson
*Assistant Examiner*—Tamthom N Truong
(74) *Attorney, Agent, or Firm*—Daniel B. Moran

(57) ABSTRACT

The invention provides a method of treating or inhibiting the growth of cancerous tumor cells and associated diseases in a mammal in need thereof which comprises administering to said mammal an effective amount of a substituted triazolopyrimidine derivative or a pharmaceutically acceptable salt thereof and further provides a method of treating or inhibiting the growth of cancerous tumor cells and associated diseases in a mammal in need thereof by interacting with tubulin and microtubules and promoting microtubule polymerization which comprises administering to said mammal an effective amount of a substituted triazolopyrimidine derivative or a pharmaceutically acceptable salt thereof.

16 Claims, No Drawings

SUBSTITUTED-TRIAZOLOPYRIMIDINES AS ANTICANCER AGENTS

CROSS REFERENCE TO RELATED APPLICATIONS

This application claims benefit of U.S. Provisional Appl. No. 60/215,585, which was filed Jun. 30, 2000. This application is herein incorporated by reference.

BACKGROUND OF THE INVENTION

1. Field of the Invention

The present invention relates to a method of treating or inhibiting the growth of cancerous tumour cells and associated diseases in a mammal by administering an effective amount of a substituted-triazolopyrimidine derivative and pharmaceutically acceptable salts thereof. Further, the present invention relates to a method for the treatment or prevention of (MDR) multiple drug resistance in a mammal in need thereof which method comprises adminstering to said mammal an effective amount of a substituted triazolopyrimidine derivative or a pharmaceutically acceptable salt thereof. More specifically, the present invention relates to a method of treating or inhibiting the growth of cancerous tumour cells and associated diseases in a mammal by interacting with tubulin and microtubules and promotion of microtubule polymerization which comprises administering to said mammal an effective amount of a substituted-triazolopyrimidine derivative and pharmaceutically acceptable salts thereof.

2. Description of the Prior Art

Most of the cytostatics in use today either inhibit the formation of essential precursors for biosynthesis of DNA or block DNA polymerases or interfere with the template function of DNA because DNA was the primary target for developing therapeutic drugs for chemotherapy. Unfortunately, inhibition of the formation of essential precursors for biosynthesis of DNA or blocking DNA polymerases or interference with the template function of DNA also affects normal tissues.

Microtubules are among the cellular structures necessary for cell growth. Tubulin is the biochemical target for several anticancer drugs, which include the vinca alkaloids vincristine and vinblastine. The interaction of vincristine and vinblastine by binding to the alpha and beta-tubulin subunits interfere with the growing and shortening of the microtubules and prevents the formation of microtubules necessary for cell functions. While these compounds have efficacy in cancer chemotherapy, they also have a destabilizing effect on the microtubules which also affects rapidly proliferating normal tissues and leads to toxicity.

Paclitaxel and its semisynthetic derivative docetaxel (Taxotere®) also interfere with microtubule formation and stabilise microtubules. Paclitaxel (Taxol®),is a diterpene isolated from the bark of the Western (Pacific) yew, *Taxus brevifolia* and is representative of a new class of therapeutic agent having a taxane ring system. It was additionally found in other members of the Taxacae family including the yew of Canada (*Taxus canadensis*) found in Gaspesia, eastern Canada and *Taxus baccata* found in Europe whose needles contain paclitaxel and analogs and hence provide a renewable source of paclitaxel and derivatives. The crude extract was tested for the first time during the 1960s and its active principle was isolated in 1971 and the chemical structure identified (M. C. Wani et al, J. Am. Chem. Soc., 93, 2325 (1971)). Further, a wide range of activity over melanoma cells, leukemia, various carcinomas, sarcomas and non-Hodgkin lymphomas as well as a number of solid tumors in animals was shown through additional testing. Paclitaxel and its analogs have been produced by partial synthesis from 10-deacetylbaccatin III, a precursor obtained from yew needles and twigs, and by total synthesis (Holton, et al., J. Am. Chem. Soc. 116:1597-1601 (1994) and Nicolaou, et al., Nature 367:630-634 (1994)). Paclitaxel has been demonstrated to possess antineoplastic activity. More recently, it was shown that the antitumor activity of paclitaxel is due to a promotion of microtubule polymerization (Kumar, N., J. Biol. Chem. 256:10435-10441 (1981); Rowinsky, et al., J. Natl. Cancer Inst., 82:1247-1259 (1990); and Schiff, et al., Nature, 277:665-667 (1979)). Paclitaxel has now demonstrated efficacy in several human tumors in clinical trials (McGuire, et al., Ann. Int. Med., 111:273-279 (1989); Holmes, et al., J. Natl. Cancer Inst., 83:1797-1805 (1991); Kohn et al., J. Natl. Cancer Inst., 86:18-24 (1994); and A. Bicker et al., Anti-Cancer Drugs, 4,141-148 (1993)

Paclitaxel is a microtubule blocker, inhibiting mitosis by interaction with microtubules. Paclitaxel does not prevent tubulin assembly but rather accelerates tubulin polymerization and stabilizes the assembled microtubules. Paclitaxel acts in a unique way which consists in binding to microtubules, preventing their depolymerization under conditions where usually depolymerization occurred(dilution, calcium, cold and microtubules disrupting drugs). Paclitaxel blocks the cell cycle at prophase which results in an accumulation of cells in G2+M.

Accordingly, there is still a need in the art for cytotoxic agents for use in cancer therapy. In particular, there is a need for drugs which inhibit or treat the growth of tumors which have an effect similar to paclitaxel and interfere with the process of microtubule formation. Additionally, there is a need in the art for agents which accelerate tubulin polymerization and stabilize the assembled microtubules.

Accordingly, it would be advantageous to provide a method of treating or inhibiting cell proliferation, neoplastic growth and malignant tumor growth in mammals by administering compounds which have paclitaxel like anticancer activity.

Additionally, it would be advantageous to provide a method for treating or inhibiting multiple drug resistance (MDR).

Substituted triazolopyrimidine compounds of this invention are known to the art and have found use in agriculture as fungicides. The preparation of compounds of this invention and methods of preparation are disclosed in the following U.S. Pat. Nos.: 5,593,996; 5,756,509; 5,948,783; 5,981,534; 5,612,345; 5,994,360; 6,020,338; 5,985,883; 5,854,252; 5,808,066; 5,817,663; 5,955,252; 5,965,561; 5,986,135; and 5,750,766.

Compounds of this invention are also prepared according to procedures described in the following International Publication Numbers: WO98/46607; WO98/46608; WO99/48893; WO99/41255; EPO 834513A2; EPO 782997A2; EPO 550113B1; EPO 613900B1; FR2784381A1; EPO 989130A1; WO98/41496; WO94/20501; EPO 945453A1; EPO 562615A1 and EPO 562615B1.

SUMMARY OF THE INVENTION

A first object of the present invention is to provide a method of treating or inhibiting the growth of cancerous tumour cells and associated diseases in a mammal by administering an effective amount of a substituted-triazolopyrimidine derivative and pharmaceutically acceptable salts thereof.

A second object of the present invention is to provide a method of treating or inhibiting the growth of cancerous tumour cells and associated diseases in a mammal in need thereof by interacting with tubulin and microtubules by promotion of microtubule polymerization which comprises administering to said mammal an effective amount of a substituted-triazolopyrimidine derivative and pharmaceutically acceptable salts thereof.

A third object of the present invention is to provide a method of treating or inhibiting the growth of cancerous tumour cells and associated diseases in a mammal in need thereof by administering to said mammal an effective amount of a compound of Formula (I):

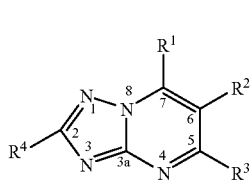

(I)

wherein:

$R^1$ is selected from the group consisting of halogen, an optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, alkoxy of 1 to 12 carbon atoms, optionally substituted aryl of 6, 10 or 14 carbon atoms, —CN, hydroxy, halogen, carbamoyl, carboxy, alkoxycarbonyl of 2 to 12 carbon atoms, heterocyclyl, optionally substituted bicycloalkyl of 5 to 10 carbon atoms, optionally substituted cycloalkyl of 3 to 8 carbon atoms in which one —CH$_2$— may also be replaced by —O—, —S—, or —NR' where R' is H or an alkyl group of 1 to 12 carbon atoms, thiophene, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl of 1 to 12 carbon atoms, —S-cycloalkyl of 3 to 8 carbon atoms, —S-alkenyl of 2 to 12 carbon atoms, —SO$_2$aryl of 6, 10 or 14 carbon atoms, —SO$_2$cycloalkyl of 3 to 8 carbon atoms, —SO$_2$alkyl of 1 to 12 carbon atoms, —O-aryl of 6, 10 or 14 carbon atoms, and the moiety —NR$^a$R$^b$;

$R^a$ is H, optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 8 carbon atoms, in which one —CH$_2$— may also be replaced by —O—, —S—, or —NR' where R' is H or an alkyl group of 1 to 12 carbon atoms, optionally substituted cycloalkenyl of 5 to 10 carbon atoms, in which one —CH$_2$— may also be replaced by —O—, —S—, or —NR' where R' is H or an alkyl group of 1 to 12 carbon atoms, optionally substituted bicycloalkyl of 5 to 10 carbon atoms, optionally substituted tricycloalkyl, haloalkyl of 1 to 10 carbon atoms, aryl of 6, 10 or 14 carbon atoms, heterocyclyl, benzyl, optionally substituted benzyl, cycloalkyl of 3 to 8 carbon atoms or a 3- to 6-membered heterocyclyl ring, optionally ortho-fused with an optionally substituted phenyl ring;

$R^b$ is H, an optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted aryl of 6, 10 or 14 carbon atoms, optionally substituted bicycloalkyl of 5 to 10 carbon atoms, optionally substituted cycloalkyl of 3 to 10 carbon atoms in which one —CH$_2$— may also be replaced by —O—, —S—, or —NR' where R' is H or an alkyl group of 1 to 12 carbon atoms, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl, —S-alkenyl, —SO$_2$aryl of 6, 10 or 14 carbon atoms, —SO$_2$cycloalkyl, —SO$_2$alkyl, —O-aryl of 6, 10 or 14 carbon atoms, heterocyclyl, benzyl, optionally substituted benzyl, cycloalkyl of 3 to 8 carbon atoms or a 3- to 6-membered heterocyclyl ring, optionally ortho-fused with an optionally substituted phenyl ring;

$R^aR^b$ together with the nitrogen atom to which each is attached represent an optionally substituted saturated or unsaturated heterocyclyl ring from 3 to 12 ring atoms in which optionally, at least one —CH$_2$— may optionally be replaced by —O—, —S—, or —NR' where R' is H or an alkyl group of 1 to 12 carbon atoms, said saturated or unsaturated heterocyclyl ring may optionally be aryl or cycloalkyl fused;

$R^2$ is H, optionally substituted alkyl of 1 to 12 carbon atoms, amino, hydroxy, alkylthio of 1 to 12 carbon atoms, cyano, carbamoyl, optionally substituted alkoxy of 1 to 12 carbon atoms, optionally substituted cycloalkyl of 3 to 8 carbon atoms, optionally substituted aryl of 6, 10 or 14 carbon atoms, carboxy, alkoxycarbonyl of 2 to 12 carbon atoms, aryloxy, benzyloxy, thienyl, heterocyclyl or halogen;

$R^3$ is H, halogen, alkyl of 1 to 12 carbon atoms, alkoxy of 1 to 12 carbon atoms, aryloxy, —NR$^c$R$^d$, benzyloxy, aralkyloxy, haloalkoxy of 1 to 12 carbon atoms, alkylthio of 1 to 12 carbon atoms, heterocyclyl, aryl, hydroxy, carbamoyl, carboxy, alkoxycarbonyl of 2 to 12 carbon atoms, cyano, amino, alkylamino of 1 to 12 carbon atoms, dialkylamino of 1 to 12 carbon atoms, or —N$_3$;

$R^c$ is H, amino, optionally substituted alkyl of 1 to 12 carbon atoms, haloalkyl of 1 to 10 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 10 carbon atoms, in which one —CH$_2$— may also be replaced by —O—, —S—, or —NR' where R' is H or an alkyl group of 1 to 12 carbon atoms optionally substituted cycloalkenyl of 5 to 10 carbon atoms, in which one —CH$_2$— may also be replaced by —O—, —S—, or —NR' where R' is H or an alkyl group of 1 to 12 carbon atoms, optionally substituted bicycloalkyl of 5 to 10 carbon atoms, aryl of 6, 10 or 14 carbon atoms, benzyl, optionally substituted benzyl, or heterocyclyl;

$R^d$ is H, amino, optionally substituted alkyl of 1 to 12 carbon atoms, haloalkyl of 1 to 10 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 10 carbon atoms, in which one —CH$_2$— may also be replaced by —O—, —S—, or —NR' where R' is H or an alkyl group of 1 to 12 carbon atoms optionally substituted cycloalkenyl of 5 to 10 carbon atoms, in which one —CH$_2$— may also be replaced by —O—, —S—, or —NR' where R' is H or an alkyl group of 1 to 12 carbon atoms optionally substituted bicycloalkyl of 5 to 10 carbon atoms, aryl of 6, 10 or 14 carbon atoms, benzyl, optionally substituted benzyl, or heterocyclyl;

$R^c R^d$ together with the nitrogen atom to which each is attached represent an optionally substituted heterocyclyl ring from 3 to 8 ring atoms optionally substituted in which one —CH$_2$— may also be replaced by —O—, —S—, or —NR' where R' is H or alkyl of 1 to 12 carbon atoms;

$R^4$ is H, optionally substituted alkyl of 1 to 12 carbon atoms, optionally substituted alkoxy of 1 to 12 carbon atoms, amino, alkyl amino of 1 to 12 carbon atoms, dialkylamino of 1 to 12 carbon atoms, alkylthio of 1 to 12 carbon atoms, halogen, cyano, carboxy, alkoxycarbonyl of 2 to 12 carbon atoms, heterocyclyl, halogen, carbamoyl, optionally substituted aryl of 6, 10 or 14 carbon atoms, or —CF$_3$;

provided that when: a) $R^1$ is diethylamino, $R^3$ is chloro, $R^4$ is hydrogen, $R^2$ is not 4-trifluoromethylphenyl, 3,4-dichlorophenyl, 4-chlorophenyl, 3-chloro-4-methoxyphenyl; b) $R^1$ is diethylamino, $R^3$ is bromo, $R^4$ is hydrogen, $R^2$ is not 4-trifluoromethylphenyl; c) $R^1$ is isopropylamino, $R^3$ is chloro, $R^4$ is hydrogen, $R^2$ is not 2-benzyloxyphenyl or 3,4,5-trimethoxyphenyl; d) $R^1$ is cyclopentylamino, $R^3$ is chloro, $R_4$ is hydrogen, $R^2$ is not 3,4,5-trimethoxyphenyl, 2-napthyl or 2-stilbene; e) $R^1$ is 2-amino-bicyclo(2.2.1.)heptyl, $R^3$ is chloro, $R^4$ is hydrogen, $R^2$ is not 3,4,5-trimethoxyphenyl and f) $R^1$ is diethylamino, $R^3$ is chloro, $R^4$ is hydrogen, $R^2$ is not 4-trifluoromethylphenyl and g) $R^1$ is 1,1,1-trifluoroethoxy, $R^3$ is chloro, $R^4$ is hydrogen, $R^2$ is not 2-chloro-6-fluorophenyl h) $R^1$ is —SO$_2$ethyl or —SO$_2$cyclopentyl, $R^3$ is chloro, $R^4$ is hydrogen, $R^2$ is not 2-chloro-6-fluorophenyl; i) $R^4$ is hydrogen, $R^2$ is 2-chloro-6-fluorophenyl, $R^1$ and $R^3$ are not 1,2,4-triazole; j) $R^1$ is cyclohexyl, $R^4$ is hydrogen, $R^2$ is 2,4,6-trifluorophenyl, and $R^3$ is not —OCH$_2$O$_2$C(CH$_3$)$_3$; k) $R^1$ is 2-thienyl, $R^4$ is ethyl, $R^3$ is hydrogen and $R^2$ is not 2-methoxyphenyl, 4-methoxyphenyl, and 4-trifluorophenyl; i) $R^2$ is phenyl, $R^3$ is chloro, $R^4$ is hydrogen, $R^1$ is not (2E)-,7-dimethyl-2,6-octadienyl or a pharmaceutically acceptable salt thereof.

A fourth object of the present invention is to provide a method of treating or inhibiting the growth of cancerous tumour cells and associated diseases in a mammal in need thereof by interacting with tubulin and microtubules by promotion of microtubule polymerization which comprises administering to said mammal an effective amount of a compound of Formula (I):

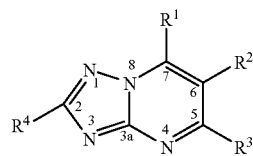

(I)

wherein:

$R^1$ is selected from the group consisting of halogen, an optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, alkoxy of 1 to 12 carbon atoms, optionally substituted aryl of 6, 10 or 14 carbon atoms, —CN, hydroxy, halogen, carbamoyl, carboxy, alkoxycarbonyl of 2 to 12 carbon atoms, heterocyclyl, optionally substituted bicycloalkyl of 5 to 10 carbon atoms, optionally substituted cycloalkyl of 3 to 8 carbon atoms in which one —CH$_2$— may also be replaced by —O—, —S—, or —NR' where R' is H or an alkyl group of 1 to 12 carbon atoms, thiophene, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl of 1 to 12 carbon atoms, —S-cycloalkyl of 3 to 8 carbon atoms, —S-alkenyl of 2 to 12 carbon atoms, —SO$_2$aryl of 6, 10 or 14 carbon atoms, —SO$_2$cycloalkyl of 3 to 8 carbon atoms, —SO$_2$alkyl of 1 to 12 carbon atoms, —O-aryl of 6, 10 or 14 carbon atoms, and the moiety —NR$^a$R$^b$;

$R^a$ is H, optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 8 carbon atoms, in which one —CH$_2$— may also be replaced by —O—, —S—, or —NR' where R' is H or an alkyl group of 1 to 12 carbon atoms, optionally substituted cycloalkenyl of 5 to 10 carbon atoms, in which one —CH$_2$— may also be replaced by —O—, —S—, or —NR' where R' is H or an alkyl group of 1 to 12 carbon atoms, optionally substituted bicycloalkyl of 5 to 10 carbon atoms, optionally substituted tricycloalkyl, haloalkyl of 1 to 10 carbon atoms, aryl of 6, 10 or 14 carbon atoms, heterocyclyl, benzyl, optionally substituted benzyl, cycloalkyl of 3 to 8 carbon atoms or a 3- to 6-membered heterocyclyl ring, optionally ortho-fused with an optionally substituted phenyl ring;

$R^b$ is H, an optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted aryl of 6, 10 or 14 carbon atoms, optionally substituted bicycloalkyl of 5 to 10 carbon atoms, optionally substituted cycloalkyl of 3 to 10 carbon atoms in which one —CH$_2$— may also be replaced by —O—, —S—, or —NR' where R' is H or an alkyl group of 1 to 12 carbon atoms, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl, —S-alkenyl, —SO$_2$aryl of 6, 10 or 14 carbon atoms, —SO$_2$cycloalkyl, —SO$_2$alkyl, —O-aryl of 6, 10 or 14 carbon atoms, heterocyclyl, benzyl, optionally substituted benzyl, cycloalkyl of 3 to 8 carbon atoms or a 3- to 6-membered heterocyclyl ring, optionally ortho-fused with an optionally substituted phenyl ring;

$R^a R^b$ together with the nitrogen atom to which each is attached represent an optionally substituted saturated or unsaturated heterocyclyl ring from 3 to 12 ring atoms in which optionally, at least one —CH$_2$— may optionally be replaced by —O—, —S—, or —NR' where R' is H or an alkyl group of 1 to 12 carbon atoms, said saturated or unsaturated heterocyclyl ring may optionally be aryl or cycloalkyl fused;

$R^2$ is H, optionally substituted alkyl of 1 to 12 carbon atoms, amino, hydroxy, alkylthio of 1 to 12 carbon atoms, cyano, carbamoyl, optionally substituted alkoxy of 1 to 12 carbon atoms, optionally substituted cycloalkyl of 3 to 8 carbon atoms, optionally substituted aryl of 6, 10 or 14 carbon atoms, carboxy, alkoxycarbonyl of 2 to 12 carbon atoms, aryloxy, benzyloxy, thienyl, heterocyclyl or halogen;

$R^3$ is H, halogen, alkyl of 1 to 12 carbon atoms, alkoxy of 1 to 12 carbon atoms, aryloxy, —$NR^cR^d$, benzyloxy, aralkyloxy, haloalkoxy of 1 to 12 carbon atoms, alkylthio of 1 to 12 carbon atoms, heterocyclyl, aryl, hydroxy, carbamoyl, carboxy, alkoxycarbonyl of 2 to 12 carbon atoms, cyano, amino, alkylamino of 1 to 12 carbon atoms, dialkylamino of 1 to 12 carbon atoms, or —$N_3$;

$R^c$ is H, amino, optionally substituted alkyl of 1 to 12 carbon atoms, haloalkyl of 1 to 10 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 10 carbon atoms, in which one —$CH_2$— may also be replaced by —O—, —S—, or —NR' where R' is H or an alkyl group of 1 to 12 carbon atoms optionally substituted cycloalkenyl of 5 to 10 carbon atoms, in which one —$CH_2$— may also be replaced by —O—, —S—, or —NR' where R' is H or an alkyl group of 1 to 12 carbon atoms optionally substituted bicycloalkyl of 5 to 10 carbon atoms, aryl of 6, 10 or 14 carbon atoms, benzyl, optionally substituted benzyl, heterocyclyl;

$R^d$ is H, amino, optionally substituted alkyl of 1 to 12 carbon atoms, haloalkyl of 1 to 10 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 10 carbon atoms, in which one —$CH_2$— may also be replaced by —O—, —S—, or —NR' where R' is H or an alkyl group of 1 to 12 carbon atoms optionally substituted cycloalkenyl of 5 to 10 carbon atoms, in which one —$CH_2$— may also be replaced by —O—, —S—, or —NR' where R' is H or an alkyl group of 1 to 12 carbon atoms optionally substituted bicycloalkyl of 5 to 10 carbon atoms, aryl of 6, 10 or 14 carbon atoms, benzyl, optionally substituted benzyl, or heterocyclyl;

$R^cR^d$ together with the nitrogen atom to which each is attached represent an optionally substituted heterocyclyl ring from 3 to 8 ring atoms optionally substituted in which one —$CH_2$— may also be replaced by —O—, —S—, or —NR' where R' is H or alkyl of 1 to 12 carbon atoms;

$R^4$ is H, optionally substituted alkyl of 1 to 12 carbon atoms, optionally substituted alkoxy of 1 to 12 carbon atoms, amino, alkyl amino of 1 to 12 carbon atoms, dialkylamino of 1 to 12 carbon atoms, alkylthio of 1 to 12 carbon atoms, halogen, cyano, carboxy, alkoxycarbonyl of 2 to 12 carbon atoms, heterocyclyl, halogen, carbamoyl, optionally substituted aryl of 6, 10 or 14 carbon atoms, or —$CF_3$;

provided that when: a) $R^1$ is diethylamino, $R^3$ is chloro, $R^4$ is hydrogen, $R^2$ is not 4-trifluoromethylphenyl, 3,4-dichlorophenyl, 4-chlorophenyl, 3-chloro-4-methoxyphenyl; b) $R^1$ is diethylamino, $R^3$ is bromo, $R^4$ is hydrogen, $R^2$ is not 4-trifluoromethylphenyl; c) $R^1$ is isopropylamino, $R^3$ is chloro, $R^4$ is hydrogen, $R^2$ is not 2-benzyloxyphenyl or 3,4,5-trimethoxyphenyl; d) $R^1$ is cyclopentylamino, $R^3$ is chloro, $R^4$ is hydrogen, $R^2$ is not 3,4,5-trimethoxyphenyl, 2-napthyl or 2-stilbene; e) $R^1$ is 2-amino-bicyclo(2.2.1.)heptyl, $R^3$ is chloro, $R^4$ is hydrogen, $R^2$ is not 3,4,5-trimethoxyphenyl and f) $R^1$ is diethylamino, $R^3$ is chloro, $R^4$ is hydrogen, $R^2$ is not 4-trifluoromethylphenyl and g) $R^1$ is 1,1,1-trifluoroethoxy, $R^3$ is chloro, $R^4$ is hydrogen, $R^2$ is not 2-chloro-6-fluorophenyl h) $R^1$ is —$SO_2$ethyl or —$SO_2$cyclopentyl, $R^3$ is chloro, $R^4$ is hydrogen, $R^2$ is not 2-chloro-6-fluorophenyl; i) $R^4$is hydrogen, $R^2$ is 2-chloro-6-fluorophenyl, $R^1$ and $R^3$ are not 1,2,4-triazole; j) $R^1$ is cyclohexyl, $R^4$ is hydrogen, $R^2$ is 2,4,6trifluorophenyl, and $R^3$ is not —$OCH_2O_2C(CH_3)_3$; k) $R^1$ is 2-thienyl, $R^4$ is ethyl, $R^3$ is hydrogen and $R^2$ is not 2-methoxyphenyl, 4-methoxyphenyl, and 4-trifluorophenyl; l) $R^2$ is phenyl, $R^3$ is chloro, $R^4$ is hydrogen $R^1$ is not (2E)-,7-dimethyl-2,6-octadienyl or a pharmaceutically acceptable salt thereof.

A fifth object of the present invention is to provide a method for the treatment or prevention of multiple drug resistance (MDR) in a mammal in need thereof which method comprises administering to said mammal an effective amount of a substituted triazolopyrimidine derivative or a pharmaceutically acceptable salt thereof. In particular the multiple drug resistance (MDR) is mediated by p-glycoprotein or MXR.

A sixth object of the present invention is to provide a method for the treatment or prevention of multiple drug reistance (MDR) in a mammal in need thereof by administering to said mammal an effective amount of a compound of Formula (I):

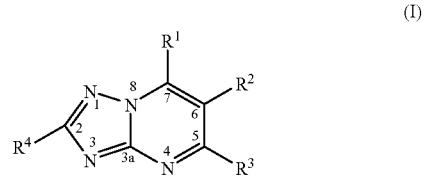

wherein:

$R^1$ is selected from the group consisting of halogen, an optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, alkoxy of 1 to 12 carbon atoms, optionally substituted aryl of 6, 10 or 14 carbon atoms, —CN, hydroxy, halogen, carbamoyl, carboxy, alkoxycarbonyl of 2 to 12 carbon atoms, heterocyclyl, optionally substituted bicycloalkyl of 5 to 10 carbon atoms, optionally substituted cycloalkyl of 3 to 8 carbon atoms in which one —$CH_2$— may also be replaced by —O—, —S—, or —NR' where R' is H or an alkyl group of 1 to 12 carbon atoms, thiophene, optionally substituted cycloalkenyl of 5 to 10 carbon atoms in which one —$CH_2$— may also be replaced by —O—, —S—, or —NR' where R' is H or an alkyl group of 1 to 12 carbon atoms, —S-aryl of 6, 10 or 14 carbon atoms, —S-alkyl of 1 to 12 carbon atoms, —S-cycloalkyl of 3 to 8 carbon atoms, —S-alkenyl of 2 to 12 carbon atoms, —$SO_2$aryl of 6, 10 or 14 carbon atoms, —$SO_2$cycloalkyl of 3 to 8 carbon atoms, —$SO_2$alkyl of 1 to 12 carbon atoms, —O-aryl of 6, 10 or 14 carbon atoms, and the moiety —$NR^aR^b$;

$R^a$ is H, optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 8 carbon atoms, in which one —$CH_2$— may also be replaced by —O—, —S—, or —NR' where R' is H or an alkyl group of 1 to 12 carbon atoms, optionally substituted cycloalkenyl of 5 to 10 carbon atoms, in which one —CH$_2$— may also be replaced by —O—, —S—, or —NR' where R' is H or an alkyl group of 1 to 12 carbon atoms, optionally substituted bicycloalkyl of 5 to 10 carbon atoms, optionally substituted tricycloalkyl, haloalkyl of 1 to 10 carbon atoms, aryl of 6, 10 or 14 carbon atoms, heterocyclyl, benzyl, optionally substituted benzyl, cycloalkyl of 3 to 8 carbon atoms or a 3- to 6-membered heterocyclyl ring, optionally ortho-fused with an optionally substituted phenyl ring;

$R^b$ is H, an optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted aryl of 6, 10 or 14 carbon atoms, optionally substituted bicycloalkyl of 5 to 10 carbon atoms, optionally substituted cycloalkyl of 3 to 10 carbon atoms in which one —CH$_2$— may also be replaced by —O—, —S—, or —NR' where R' is H or an alkyl group of 1 to 12 carbon atoms, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl, —S-alkenyl, —SO$_2$aryl of 6, 10 or 14 carbon atoms, —SO$_2$cycloalkyl, —SO$_2$alkyl, —O-aryl of 6, 10 or 14 carbon atoms, heterocyclyl, benzyl, optionally substituted benzyl, cycloalkyl of 3 to 8 carbon atoms or a 3- to 6-membered heterocyclyl ring, optionally ortho-fused with an optionally substituted phenyl ring;

$R^aR^b$ together with the nitrogen atom to which each is attached represent an optionally substituted saturated or unsaturated heterocyclyl ring from 3 to 12 ring atoms in which optionally, at least one —CH$_2$— may optionally be replaced by —O—, —S—, or —NR' where R' is H or an alkyl group of 1 to 12 carbon atoms, said saturated or unsaturated heterocyclyl ring may optionally be aryl or cycloalkyl fused;

$R^2$ is H, optionally substituted alkyl of 1 to 12 carbon atoms, amino, hydroxy, alkylthio of 1 to 12 carbon atoms, cyano, carbamoyl, optionally substituted alkoxy of 1 to 12 carbon atoms, optionally substituted cycloalkyl of 3 to 8 carbon atoms, optionally substituted aryl of 6, 10 or 14 carbon atoms, carboxy, alkoxycarbonyl of 2 to 12 carbon atoms, aryloxy, benzyloxy, thienyl, heterocyclyl or halogen;

$R^3$ is H, halogen, alkyl of 1 to 12 carbon atoms, alkoxy of 1 to 12 carbon atoms, aryloxy, —NR$^c$R$^d$, benzyloxy, aralkyloxy, haloalkoxy of 1 to 12 carbon atoms, alkylthio of 1 to 12 carbon atoms, heterocyclyl, aryl, hydroxy, carbamoyl, carboxy, alkoxycarbonyl of 2 to 12 carbon atoms, cyano, amino, alkylamino of 1 to 12 carbon atoms, dialkylamino of 1 to 12 carbon atoms, or —N$_3$;

$R^c$ is H, amino, optionally substituted alkyl of 1 to 12 carbon atoms, haloalkyl of 1 to 10 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 10 carbon atoms, in which one —CH$_2$— may also be replaced by —O—, —S—, or —NR' where R' is H or an alkyl group of 1 to 12 carbon atoms optionally substituted cycloalkenyl of 5 to 10 carbon atoms, in which one —CH$_2$— may also be replaced by —O—, —S—, or —NR' where R' is H or an alkyl group of 1 to 12 carbon atoms, optionally substituted bicycloalkyl of 5 to 10 carbon atoms, aryl of 6, 10 or 14 carbon atoms, benzyl, optionally substituted benzyl, or heterocyclyl;

$R^d$ is H, amino, optionally substituted alkyl of 1 to 12 carbon atoms, haloalkyl of 1 to 10 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted cycloalkyl of 3 to 10 carbon atoms, in which one —CH$_2$— may also be replaced by —O—, —S—, or —NR' where R' is H or an alkyl group of 1 to 12 carbon atoms optionally substituted cycloalkenyl of 5 to 10 carbon atoms, in which one —CH$_2$— may also be replaced by —O—, —S—, or —NR' where R' is H or an alkyl group of 1 to 12 carbon atoms optionally substituted bicycloalkyl of 5 to 10 carbon atoms, aryl of 6, 10 or 14 carbon atoms, benzyl, optionally substituted benzyl, or heterocyclyl;

$R^cR^d$ together with the nitrogen atom to which each is attached represent an optionally substituted heterocyclyl ring from 3 to 8 ring atoms optionally substituted in which one —CH$_2$— may also be replaced by —O—, —S—, or —NR' where R' is H or alkyl of 1 to 12 carbon atoms;

$R^4$ is H, optionally substituted alkyl of 1 to 12 carbon atoms, optionally substituted alkoxy of 1 to 12 carbon atoms, amino, alkyl amino of 1 to 12 carbon atoms, dialkylamino of 1 to 12 carbon atoms, alkylthio of 1 to 12 carbon atoms, halogen, cyano, carboxy, alkoxycarbonyl of 2 to 12 carbon atoms, heterocyclyl, halogen, carbamoyl, optionally substituted aryl of 6, 10 or 14 carbon atoms, or —CF$_3$;

provided that when: a) $R^1$ is diethylamino, $R^3$ is chloro, $R^4$ is hydrogen, $R^2$ is not 4-trifluoromethylphenyl, 3,4-dichlorophenyl, 4-chlorophenyl, 3-chloro-4-methoxyphenyl; b) $R^1$ is diethylamino, $R^3$ is bromo, $R^4$ is hydrogen, $R^2$ is not 4-trifluoromethylphenyl; c) $R^1$ is isopropylamino, $R^3$ is chloro, $R^4$ is hydrogen, $R^2$ is not 2-benzyloxyphenyl or 3,4,5-trimethoxyphenyl; d) $R^1$ is cyclopentylamino, $R^3$ is chloro, $R^4$ is hydrogen, $R^2$ is not 3,4,5-trimethoxyphenyl, 2-napthyl or 2-stilbene; e) $R^1$ is 2-amino-bicyclo(2.2.1.)heptyl, $R^3$ is chloro, $R^4$ is hydrogen, $R^2$ is not 3,4,5-trimethoxyphenyl and f) $R^1$ is diethylamino, $R^3$ is chloro, $R^4$ is hydrogen, $R^2$ is not 4-trifluoromethylphenyl and g) $R^1$ is 1,1,1-trifluoroethoxy, $R^3$ is chloro, $R^4$ is hydrogen, $R^2$ is not 2-chloro-6-fluorophenyl h) $R^1$ is —SO$_2$ethyl or —SO$_2$cyclopentyl, $R^3$ is chloro, $R^4$ is hydrogen, $R^2$ is not 2-chloro-6-fluorophenyl; i) $R^4$ is hydrogen, $R^2$ is 2-chloro-6-fluorophenyl, $R^1$ and $R^3$ are not 1,2,4-triazole; j) $R^1$ is cyclohexyl, $R^4$ is hydrogen, $R^2$ is 2,4,6-trifluorophenyl, and $R^3$ is not —OCH$_2$O$_2$C(CH$_3$)$_3$; k) $R^1$ is 2-thienyl, $R^4$ is ethyl, $R^3$ is hydrogen and $R^2$ is not 2-methoxyphenyl, 4-methoxyphenyl, and 4-trifluorophenyl; l) $R^2$ is phenyl, $R^3$ is chloro, $R^4$ is hydrogen, $R^1$ is not (2 E)-,7-dimethyl-2,6-octadienyl or a pharmaceutically acceptable salt thereof.

Among the preferred groups of compounds of Formula (I) including pharmaceutically acceptable salts thereof useful for the methods of this invention are those in the subgroups below wherein the other variables of Formula (I) in the subgroups are as defined above wherein:

a) $R^1$ is selected from the group consisting of an optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted aryl of 6, 10 or 14 carbon atoms, optionally substituted bicycloalkyl of 5 to 10 carbon atoms, optionally substituted cycloalkyl of 3 to 8 carbon atoms in which one —CH$_2$— may also be replaced by —O—, —S—, or —NR' where R' is H or an alkyl group of 1 to 12 carbon atoms, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl of 1 to 12 carbon atoms, —S-alkenyl of 2 to 12 carbon atoms, —SO$_2$aryl of 6, 10 or 14 carbon atoms, —SO$_2$cycloalkyl of 3 to 8 carbon atoms, —SO$_2$alkyl of 1 to 12 carbon atoms, —O-aryl of 6, 10 or 14 carbon atoms, and the moiety —NR$^a$R$^b$;

b) R$^a$ and R$^b$ each independently represent the moiety —C*H(R$^e$)(R$^f$) where R$^e$ and R$^f$ independently represent an optionally halo-substituted alkyl group of 1 to 12 carbon atoms where C* represents the (R) or (S) isomer;

c) R$^2$ is optionally substituted aryl of 6, 10 or 14 carbon atoms, aryloxy, thienyl, benzyloxy, heterocyclyl or halogen;

d) R$^3$ is halogen, alkyl of 1 to 12 carbon atoms, alkoxy of 1 to 12 carbon atoms, aryloxy, —NR$^c$R$^d$, benzyloxy, aralkyloxy, haloalkoxy of 1 to 12 carbon atoms, alkylthio of 1 to 12 carbon atoms, hydroxy, cyano, amino, alkylamino of 1 to 12 carbon atoms, dialkylamino of 1 to 12 carbon atoms, or —N$_3$;

e) R$^4$ is H, optionally substituted alkyl of 1 to 12 carbon atoms, optionally substituted alkoxy of 1 to 12 carbon atoms, amino, alkyl amino of 1 to 12 carbon atoms, dialkylamino of 1 to 12 carbon atoms, —CF$_3$;

Among the additionally preferred groups of compounds of this invention according to general Formula (I) including pharmaceutically acceptable salts thereof useful for the methods of this invention are those in the subgroups below, wherein the other variables of Formula (I) in the subgroups are as defined above wherein:

a) R$^1$ is selected from the group consisting of an optionally substituted alkyl of 1 to 12 carbon atoms, optionally substituted alkenyl of 2 to 12 carbon atoms, optionally substituted alkynyl of 2 to 12 carbon atoms, optionally substituted alkadienyl of 4 to 12 carbon atoms, optionally substituted aryl of 6, 10 or 14 carbon atoms, optionally substituted bicycloalkyl of 5 to 10 carbon atoms, optionally substituted cycloalkyl of 3 to 8 carbon atoms in which one —CH$_2$— may also be replaced by —O—, —S—, or —NR' where R' is H or an alkyl group of 1 to 12 carbon atoms, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl of 1 to 12 carbon atoms, —S-alkenyl of 2 to 12 carbon atoms, —SO$_2$aryl of 6, 10 or 14 carbon atoms, —SO$_2$cycloalkyl of 3 to 8 carbon atoms, —SO$_2$alkyl of 1 to 12 carbon atoms, —O-aryl of 6, 10 or 14 carbon atoms, and the moiety —NR$^a$R$^b$ wherein R$^a$R$^b$ are optionally taken together with the nitrogen to which each is attached;

b) R$^2$ is optionally substituted aryl of 6, 10 or 14 carbon atoms or heterocyclyl;

c) R$^3$ is halogen, alkoxy of 1 to 12 carbon atoms, —NR$^c$R$^d$, haloalkoxy of 1 to 12 carbon atoms, alkylthio of 1 to 12 carbon atoms, cyano, amino, alkylamino of 1 to 12 carbon atoms, dialkylamino of 1 to 12 carbon atoms, or —N$_3$;

d) R$^4$ is H, optionally substituted alkyl of 1 to 12 carbon atoms, amino, alkyl amino of 1 to 12 carbon atoms, dialkylamino of 1 to 12 carbon atoms, —CF$_3$;

Among the more preferred groups of compounds of Formula (I) including pharmaceutically acceptable salts thereof useful for the methods of this invention are those in the subgroups below including the pharmaceutically acceptable salts thereof wherein the other variables of Formula (I) in the subgroups are as defined above wherein:

a) R$^1$ is selected from the group consisting of an optionally substituted alkyl of 1 to 12 carbon atoms, optionally substituted cycloalkyl of 3 to 8 carbon atoms in which one —CH$_2$— may also be replaced by —O—, —S—, or —NR' where R' is H or an alkyl group of 1 to 12 carbon atoms, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl of 1 to 12 carbon atoms, —S-alkenyl of 2 to 12 carbon atoms, —SO$_2$aryl of 6, 10 or 14 carbon atoms, —SO$_2$cycloalkyl of 5 to 10 carbon atoms, —SO$_2$alkyl of 1 to 12 carbon atoms, and the moiety —NR$^a$R$^b$ wherein R$^a$R$^b$ are optionally taken together with the nitrogen to which each is attached;

b) R$^2$ is optionally substituted aryl of 6, 10 or 14 carbon atoms;

c) R$^3$ is halogen, alkoxy of 1 to 12 carbon atoms, —NR$^c$R$^d$, haloalkoxy of 1 to 12 carbon atoms, alkylthio of 1 to 12 carbon atoms, cyano, or —N$_3$;

d) R$^4$ is H;

Among the most preferred groups of compounds of Formula (I) including pharmaceutically acceptable salts thereof useful for the methods of this invention are those in the subgroups below including the pharmaceutically acceptable salts thereof wherein the other variables of Formula (I) in the subgroups are as defined above wherein:

a) R$^1$ is selected from the group consisting of an optionally substituted cycloalkyl of 3 to 8 carbon atoms in which one —CH$_2$— may also be replaced by —O—, —S—, or —NR' where R' is H or an alkyl group of 1 to 12 carbon atoms, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl of 1 to 12 carbon atoms, —S-alkenyl of 2 to 12 carbon atoms, —SO$_2$aryl of 6, 10 or 14 carbon atoms, —SO$_2$cycloalkyl of 3 to 8 carbon atoms, —SO$_2$alkyl of 1 to 12 carbon atoms, and the moiety —NR$^a$R$^b$ wherein R$^a$R$^b$ are optionally taken together with the nitrogen to which each is attached; R$^2$ is optionally substituted phenyl; R$^3$ is halogen, alkoxy of 1 to 12 carbon atoms, —NR$^c$R$^d$, haloalkoxy of 1 to 12 carbon atoms, alkylthio of 1 to 12 carbon atoms, cyano, or —N$_3$; R$^4$ is H;

b) R$^1$ is the moiety —NR$^a$R$^b$ wherein R$^a$R$^b$ are optionally taken together with the nitrogen to which each is attached; R$^2$ is optionally substituted phenyl; R$^3$ is halogen, alkoxy of 1 to 12 carbon atoms, —NR$^c$R$^d$, haloalkoxy of 1 to 12 carbon atoms, alkylthio of 1 to 12 carbon atoms, cyano, or —N$_3$; R$^4$ is H;

c) R$^1$ is the moiety —NR$^a$R$^b$ wherein R$^a$R$^b$ are optionally taken together with the nitrogen to which each is attached; R$^2$ is optionally substituted phenyl; R$^3$ is halogen, alkoxy, —NR$^c$R$^d$, haloalkoxy of 1 to 12 carbon atoms, alkylthio of 1 to 12 carbon atoms, cyano, or —N$_3$;

R$^4$ is H;

R$^a$ is H, optionally substituted alkyl of 1 to 12 carbon atoms, optionally substituted alkenyl of 2 to 12 carbon atoms, optionally substituted alkadienyl of 4 to 12 carbon atoms, optionally substituted cycloalkyl of 3 to 8 carbon atoms, in which one —CH$_2$— may also be replaced by —O—, —S—, or —NR' where R' is H or an alkyl group of 1 to 12 carbon atoms, optionally substituted cycloalkenyl of 5 to 10 carbon atoms, in which one —CH$_2$— may also be replaced by —O—, —S—, or —NR' where R' is H or an alkyl group of 1 to 12 carbon atoms, haloalkyl of 1 to 10 carbon atoms, aryl of 6, 10 or 14 carbon atoms, heterocyclyl, benzyl, optionally substituted benzyl; R$^b$ is H, an optionally substituted alkyl of 1 to 12 carbon atoms, optionally substituted alkenyl of 2 to 12 carbon atoms, optionally substituted alkadienyl of 4 to 12 carbon atoms, optionally substituted aryl of 6, 10 or 14 carbon atoms, optionally substituted cycloalkyl of 3 to 8 carbon atoms in which one —CH$_2$— may also be replaced by —O—, —S—, or —NR' where R' is H or an alkyl group of 1 to 12 carbon atoms, optionally substituted cycloalkenyl of 5 to 10 carbon atoms in which one —CH$_2$— may also be replaced by —O—, —S—, or —NR' where R' is H or an alkyl group of 1 to 12 carbon atoms, —S-aryl of 6, 10 or 14 carbon atoms, —S-alkyl of 1 to 12 carbon atoms, —S-alkenyl of 2 to 12 carbon atoms, —SO$_2$aryl of 6, 10 or 14 carbon atoms, —SO$_2$cycloalkyl of 3 to 8 carbon atoms, —SO$_2$alkyl of 1 to 12 carbon atoms, —O-aryl of 6, 10 or 14 carbon atoms; R$^a$R$^b$ together with the nitrogen atom to which each is attached represent an optionally substituted saturated or unsaturated heterocyclyl ring from 3 to 12 ring atoms in which optionally, at least one —CH$_2$— may also be replaced by —O—, —S—, or —NR' where R' is H or an alkyl group of 2 to 12 carbon atoms, said saturated or unsaturated heterocyclyl ring may optionally be aryl or cycloalkyl fused;

R$^c$ is H, amino, optionally substituted alkyl of 1 to 12 carbon atoms, haloalkyl of 1 to 10 carbon atoms, optionally substituted alkenyl of 2 to 12 carbon atoms, optionally substituted alkadienyl of 4 to 12 carbon atoms, optionally substituted cycloalkyl of 3 to 8 carbon atoms, in which one —CH$_2$— may also be replaced by —O—, —S—, or —NR' where R' is H or an alkyl group of 1 to 12 carbon atoms optionally substituted cycloalkenyl of 5 to 10 carbon atoms, in which one —CH$_2$— may also be replaced by —O—, —S—, or —NR' where R' is H or an alkyl group of 1 to 12 carbon atoms optionally substituted bicycloalkyl of 5 to 10 carbon atoms, aryl of 6, 10 or 14 carbon atoms, benzyl, optionally substituted benzyl, or heterocyclyl;

R$^d$ is H, amino, optionally substituted alkyl of 1 to 12 carbon atoms, haloalkyl of 1 to 10 carbon atoms, optionally substituted alkenyl of 2 to 12 carbon atoms, optionally substituted alkadienyl of 4 to 12 carbon atoms, optionally substituted cycloalkyl of 3 to 10 carbon atoms, in which one —CH$_2$— may also be replaced by —O—, —S—, or —NR' where R' is H or an alkyl group of 1 to 12 carbon atoms optionally substituted cycloalkenyl of 5 to 10 carbon atoms, in which one —CH$_2$— may also be replaced by —O—, —S—, or —NR' where R' is H or an alkyl group of 1 to 12 carbon atoms optionally substituted bicycloalkyl of 5 to 10 carbon atoms, aryl of 6, 10 or 14 carbon atoms, benzyl, optionally substituted benzyl, or heterocyclyl;

R$^c$R$^d$ together with the nitrogen atom to which each is attached represent an optionally substituted heterocyclyl ring from 3 to 8 ring atoms optionally substituted in which one —CH$_2$— may also be replaced by —O—, —S—, or —NR' where R' is H or alkyl of 2 to 20 carbon atoms;

d) R$^1$ is the moiety —NR$^a$R$^b$ wherein R$^a$R$^b$ are optionally taken together with the nitrogen to which each is attached;

R$^2$ is selected from

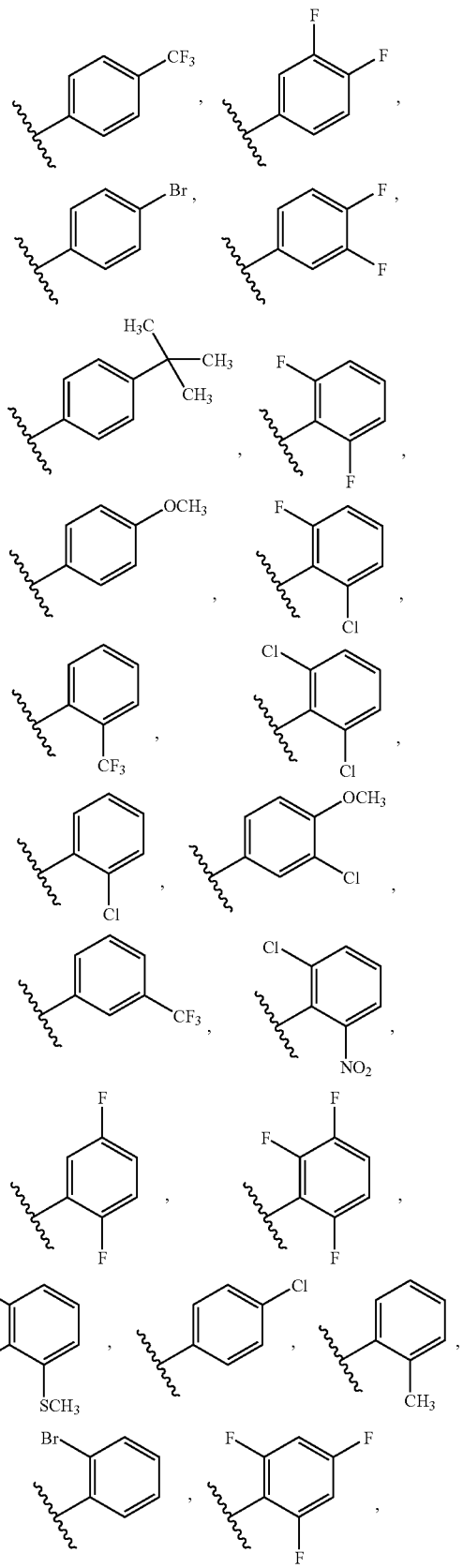

-continued
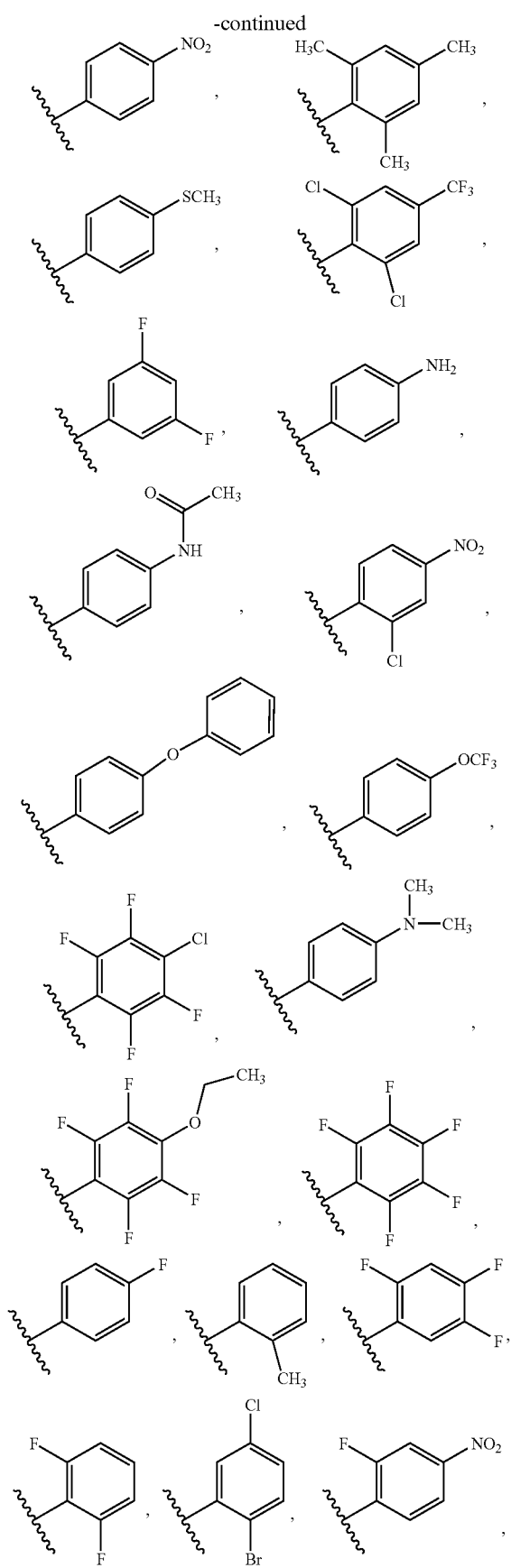
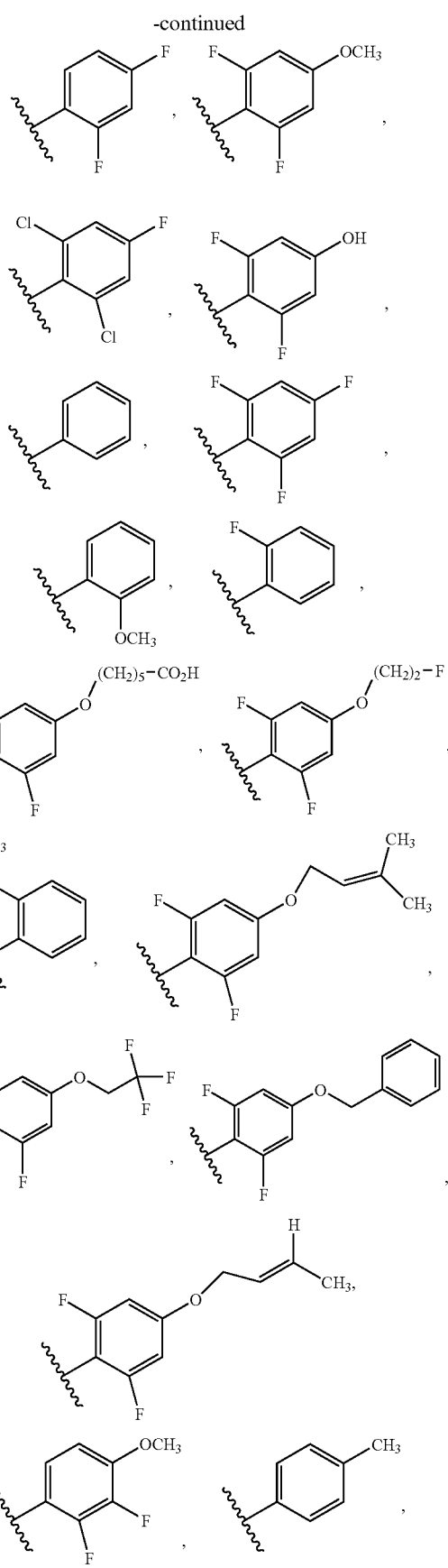

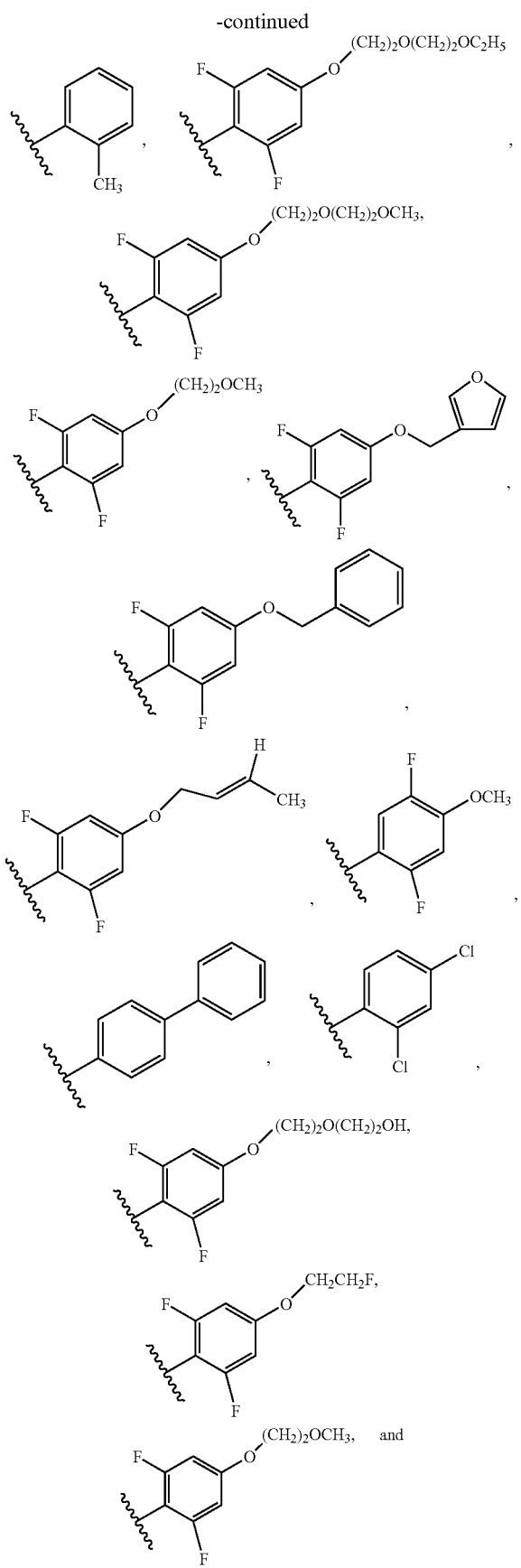
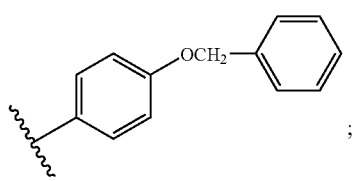
R³ is halogen, alkoxy, —NR^cR^d, haloalkoxy of 1 to 12 carbon atoms, alkylthio of 1 to 12 carbon atoms, cyano, or —N₃;
R⁴ is H;
e) R¹ is the moiety —NR^aR^b wherein R^aR^b are optionally taken together with the nitrogen to which each is attached and wherein R¹ is selected from
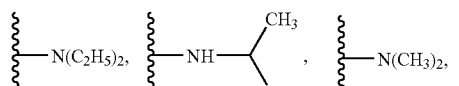
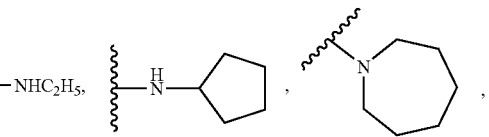
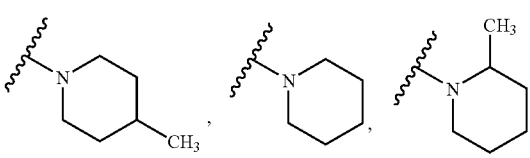
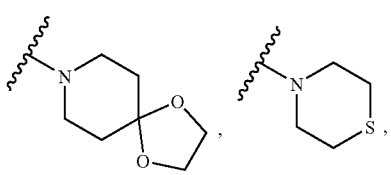
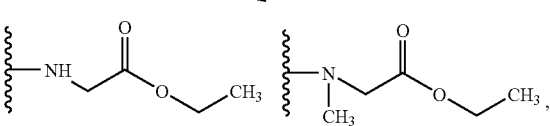
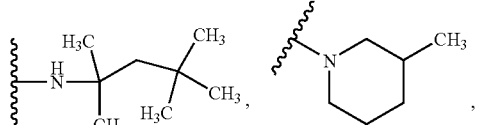
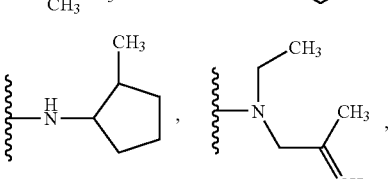
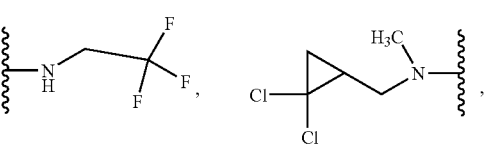

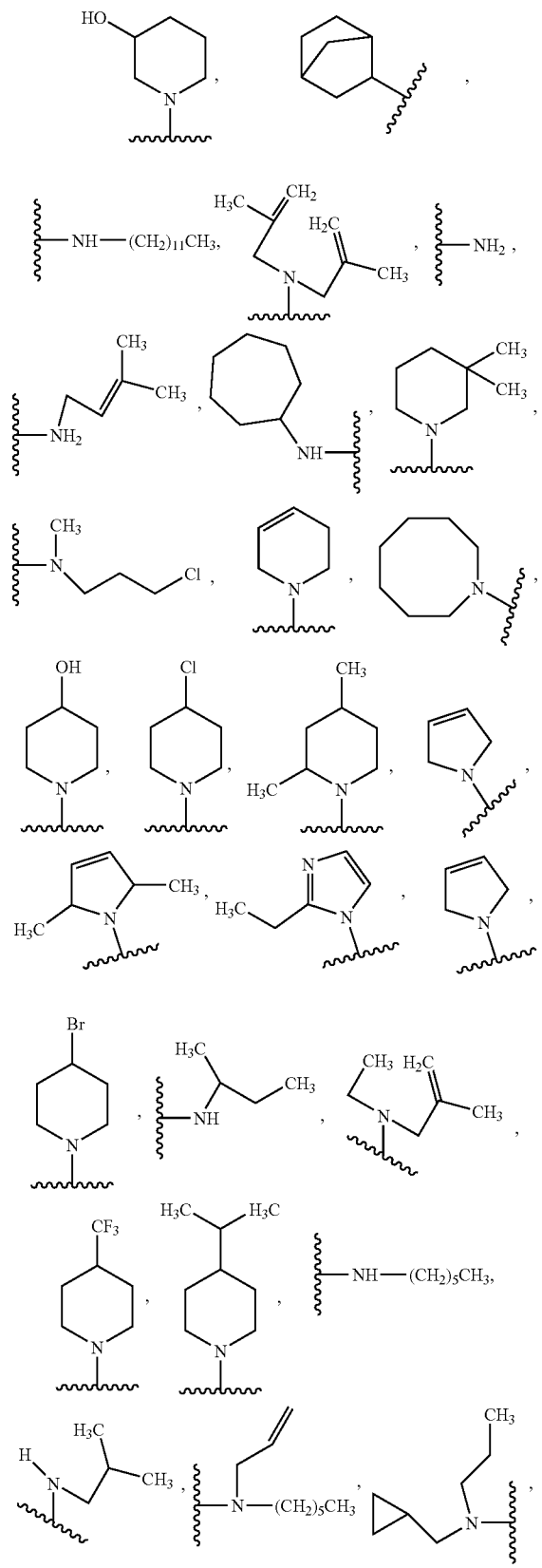
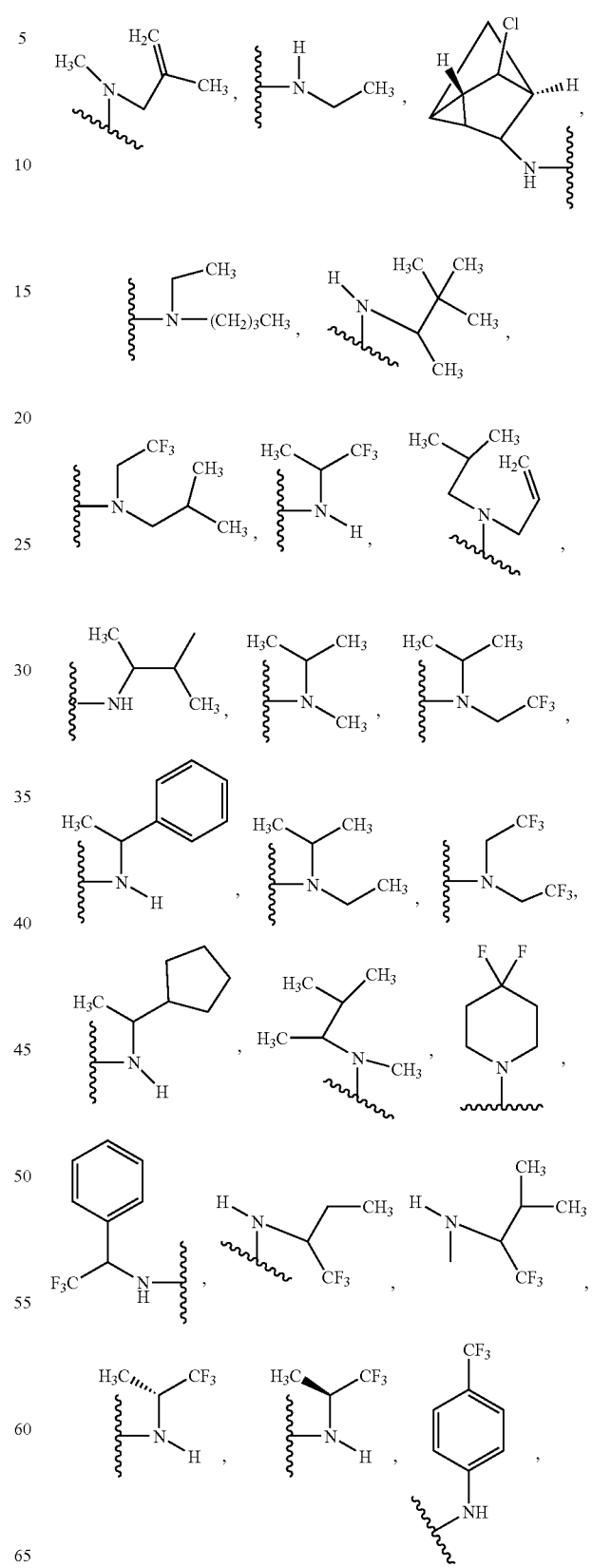

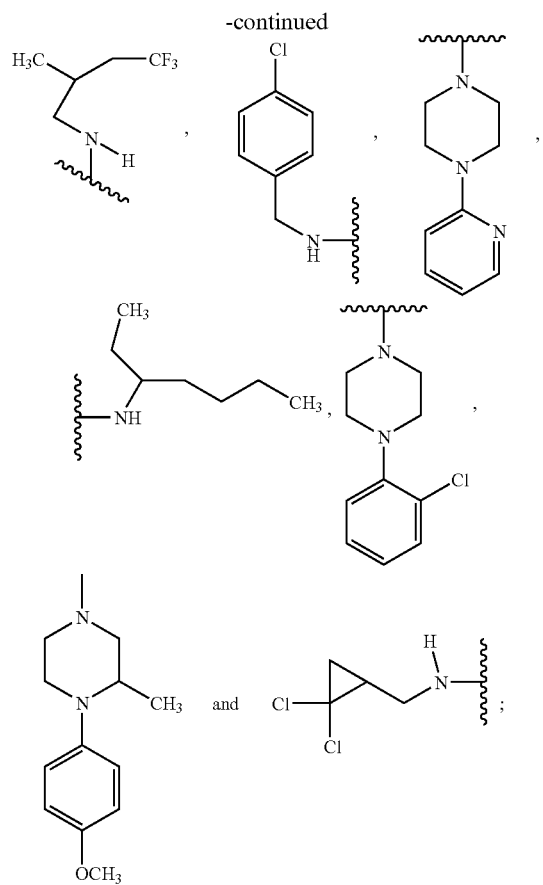
R² is optionally substituted phenyl;
R³ is halogen, alkoxy of 1 to 12 carbon atoms, —NR$^c$R$^d$, haloalkoxy of 1 to 12 carbon atoms, alkylthio of 1 to 12 carbon atoms, cyano, or —N₃;
R⁴ is H;
f) R¹ is the moiety —NR$^a$R$^b$ wherein R$^a$R$^b$ are optionally taken together with the nitrogen to which each is attached and wherein R¹ is selected from
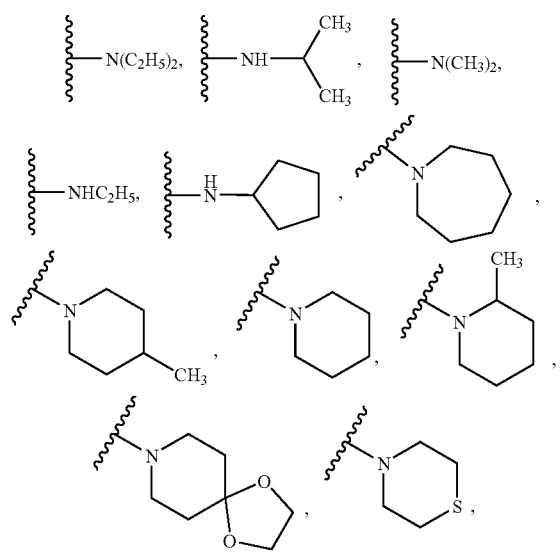

-continued

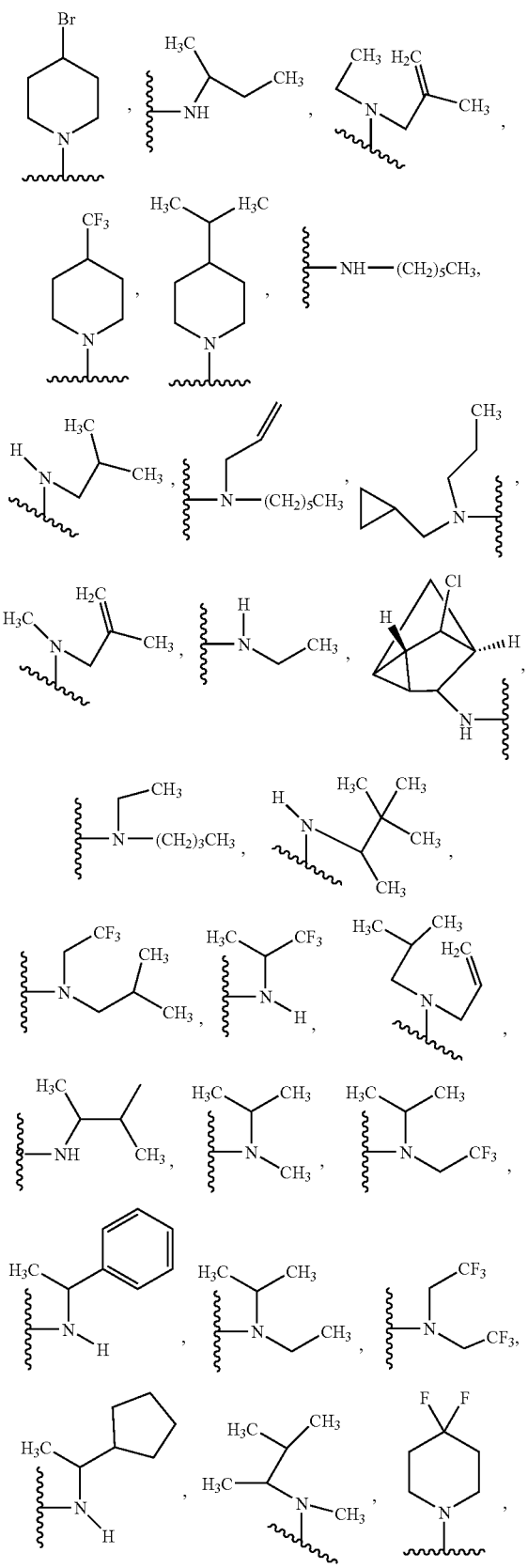
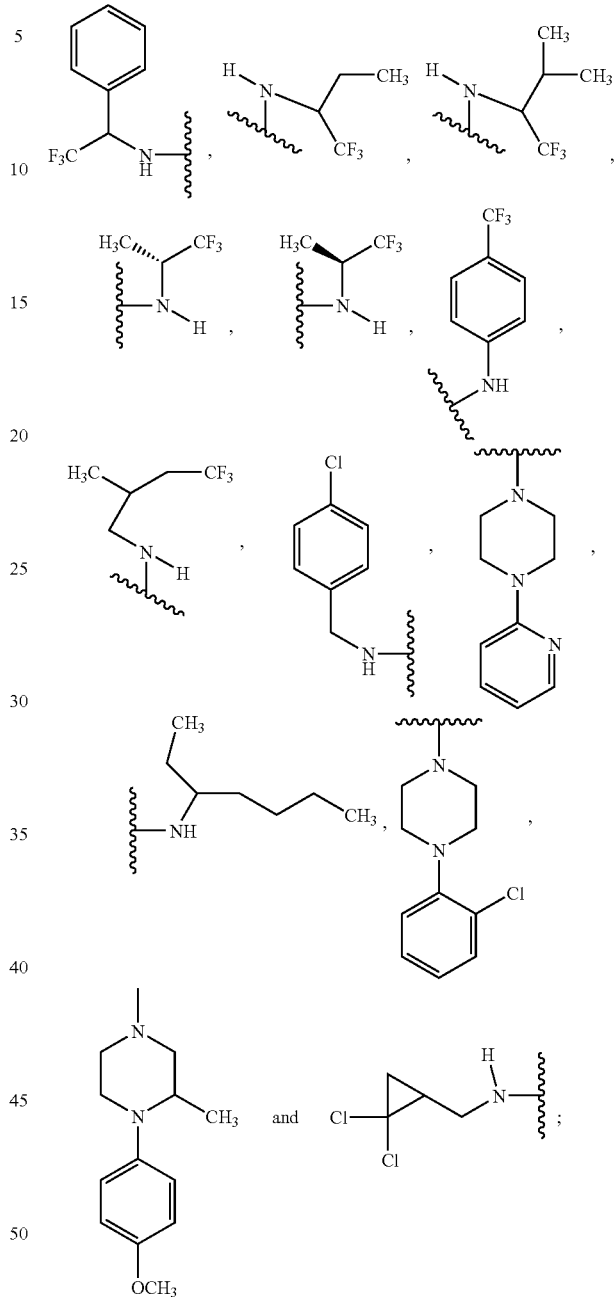

$R^2$ is optionally substituted thienyl;
$R^3$ is halogen, alkoxy of 1 to 12 carbon atoms, $-NR^cR^d$, haloalkoxy of 1 to 12 carbon atoms, alkylthio of 1 to 12 carbon atoms, cyano, or $-N_3$;
$R^4$ is H;

Also, among the most particularly preferred compounds for the methods of this invention according to Formula (I) are the following compounds or a pharmaceutically acceptable salt thereof:

7-(1-azepanyl)-5-chloro-6-phenyl[1,2,4]triazolo[1,5-a]pyrimidine;
5-chloro-6-(2,6-difluorophenyl)-7-(4-methyl-1-piperidinyl)[1,2,4]triazolo[1,5-a]pyrimidine;

5-chloro-6-(4-methoxyphenyl)-7-(1-piperidinyl)[1,2,4]triazolo[1,5-a]pyrimidine;
5-chloro-6-(2-chloro-6-fluorophenyl)-7-(4-methyl-1-piperidinyl)[1,2,4]triazolo[1,5-a]pyrimidine;
7-(1-azepanyl)-5-chloro-6-(2-chloro-6-fluorophenyl)[1,2,4]triazolo[1,5-a]pyrimidine;
5-chloro-6-(2-chloro-6-fluorophenyl)-7-(2-methyl-1-piperidinyl)[1,2,4]triazolo[1,5-a]pyrimidine;
5-chloro-6-(2-chloro-6-fluorophenyl)-7-(4-thiomorpholinyl)[1,2,4]triazolo[1,5-a]pyrimidine;
methyl [[5-chloro-6-(2-chloro-6-fluorophenyl)[1,2,4]triazolo[1,5-a]pyrimidin-7-yl](methyl)amino]acetate;
5-chloro-6-(2-chloro-6-fluorophenyl)-N-(1,1,3,3-tetramethylbutyl)[1,2,4]triazolo[1,5-a]pyrimidin-7-amine;
7-(1-azepanyl)-5-chloro-6-(4-methoxyphenyl)[1,2,4]triazolo[1,5-a]pyrimidine;
7-(1-azepanyl)-6-(4-bromophenyl)-5-chloro[1,2,4]triazolo[1,5-a]pyrimidine;
5-chloro-7-(1-piperidinyl)-6-[2-(trifluoromethyl)phenyl][1,2,4]triazolo[1,5-a]pyrimidine;
6-(4-tert-butylphenyl)-5-chloro-7-(4-methyl-1-piperidinyl)[1,2,4]triazolo[1,5-a]pyrimidine;
5-chloro-6-(4-methoxyphenyl)-7-(4-methyl-1-piperidinyl)[1,2,4]triazolo[1,5-a]pyrimidine;
5-chloro-6-(4-methoxyphenyl)-7-(3-methyl-1-piperidinyl)[1,2,4]triazolo[1,5-a]pyrimidine;
6-(4-bromophenyl)-5-chloro-7-(3-methyl-1-piperidinyl)[1,2,4]triazolo[1,5-a]pyrimidine;
5-chloro-6-(3,4-difluorophenyl)-7-(4-methyl-1-piperidinyl)[1,2,4]triazolo[1,5-a]pyrimidine;
5-chloro-6-(2,6-dichlorophenyl)-7-(2-methyl-1-pyrrolidinyl)[1,2,4]triazolo[1,5-a]pyrimidine;
5-chloro-6-(2-chlorophenyl)-7-(2-methyl-1-pyrrolidinyl)[1,2,4]triazolo[1,5-a]pyrimidine;
7-(1-azepanyl)-5-chloro-6-(3-chloro-4-methoxyphenyl)[1,2,4]triazolo[1,5-a]pyrimidine;
5-chloro-6-(3-chloro-4-methoxyphenyl)-7-(4-methyl-1-piperidinyl)[1,2,4]triazolo[1,5-a]pyrimidine;
5-chloro-6-(3-chloro-4-methoxyphenyl)-7-(2-methyl-1-piperidinyl)[1,2,4]triazolo[1,5-a]pyrimidine;
6-(4-tert-butylphenyl)-5-chloro-7-(2-methyl-1-piperidinyl)[1,2,4]triazolo[1,5-a]pyrimidine;
5-chloro-7-(2-methyl-1-piperidinyl)-6-[3-(trifluoromethyl)phenyl][1,2,4]triazolo[1,5-a]pyrimidine;
Diethyl 2-[6-(2,6-difluorophenyl)-5-ethoxy[1,2,4]triazolo[1,5-a]pyrimidin-7-yl]malonate;
7-(azepanyl)-5-chloro-6-{2-chloro-6-nitrophenyl}[1,2,4]triazolo[1,5-a]pyrimidine;
5-chloro-6-(2-chloro-6-fluorophenyl)-N-ethyl-N-(2-methyl-2-propenyl)[1,2,4]triazolo[1,5-a]pyrimidin-7-amine;
5-chloro-6-(2-chloro-6-fluorophenyl)-N-(2,2,2-trifluoroethyl)[1,2,4]triazolo[1,5-a]pyrimidin-7-amine;
5-chloro-6-(2-chloro-6-fluorophenyl)-N-[(2,2-dichlorocyclopropyl)methyl]-N-methyl[1,2,4]triazolo[1,5-a]pyrimidin-7-amine;
1-[5-chloro-6-(2-chloro-6-fluorophenyl)[1,2,4]triazolo[1,5-a]pyrimidin-7-yl]-3-piperidinol;
N-bicyclo[2.2.1]hept-2-yl-5-chloro-6-(3-chloro-4-methoxyphenyl)[1,2,4]triazolo[1,5-a]pyrimidin-7-amine;
5-chloro-6-(2,5-difluorophenyl)-N-dodecyl[1,2,4]triazolo[1,5-a]pyrimidin-7-amine;
5-chloro-7-(4-methyl-1-piperidinyl)-6-(2,3,6-trifluorophenyl)[1,2,4]triazolo[1,5-a]pyrimidine;
N-[5-chloro-6-(2,3,6-trifluorophenyl)[1,2,4]triazolo[1,5-a]pyrimidin-7-yl]-N-isopropylamine;
5-chloro-N-ethyl-N-(2-methyl-2-propenyl)-6-(2,3,6-trifluorophenyl)[1,2,4]triazolo[1,5-a]pyrimidin-7-amine;
N-allyl-5-chloro-6-(2-chloro-6-fluorophenyl)-N-(2-methyl-2-propenyl)[1,2,4]triazolo[1,5-a]pyrimidin-7-amine;
5-chloro-6-(2-chloro-6-fluorophenyl)[1,2,4]triazolo[1,5-a]pyrimidin-7-amine;
5-chloro-6-(3-chloro-4-methoxyphenyl)-N-cycloheptyl[1,2,4]triazolo[1,5-a]pyrimidin-7-amine;
5-chloro-6-(3-chloro-4-methoxyphenyl)-7-(3,3-dimethyl-1-piperidinyl)[1,2,4]triazolo[1,5-a]pyrimidine;
5-chloro-N-(3-chloropropyl)-N-methyl-6-(2,3,6-trifluorophenyl)[1,2,4]triazolo[1,5-a]pyrimidin-7-amine;
7-(1-azocanyl)-5-chloro-6-(2,3,6-trifluorophenyl)[1,2,4]triazolo[1,5-a]pyrimidine;
5-chloro-6-(2,6-difluorophenyl)-7-(3,6-dihydro-1(2H)-pyridinyl)[1,2,4]triazolo[1,5-a]pyrimidine;
7-(1-azocanyl)-5-chloro-6-(2,6-difluorophenyl)[1,2,4]triazolo[1,5-a]pyrimidine;
5-methoxy-6-(2-chloro-6-fluorophenyl)-7-(4-methyl-1-piperidinyl)[1,2,4]triazolo[1,5-a]pyrimidine;
[5-chloro-6-(2-chloro-6-fluorophenyl)[1,2,4]triazolo[1,5-a]pyrimidin-7yl]methanol;
1-[5-chloro-6-(2,6-difluorophenyl)[1,2,4]triazolo[1,5-a]pyrimidin-7-yl]-4-piperidinol;
5-chloro-7-(4-chloro-1-piperidinyl)-6-(2,6-difluorophenyl)[1,2,4]triazolo[1,5-a]pyrimidine;
5-chloro-7-(4-thiomorpholinyl)-6-(2,3,6-trifluorophenyl)[1,2,4]triazolo[1,5-a]pyrimidine;
5-chloro-6-(2,6-difluorophenyl)-7-(2,4-dimethyl-1-piperidinyl)[1,2,4]triazolo[1,5-a]pyrimidine;
7-(4-methyl-1-piperidinyl)-5-amino-6-(2-chloro-6-fluorophenyl)[1,2,4]triazolo[1,5-a]pyrimidine;
5-chloro-6-(2,6-difluorophenyl)-7-(2,5-dihydro-1H-pyrrol-1-yl)[1,2,4]triazolo[1,5-a]pyrimidine;
5-chloro-6-(2-chloro-6-fluorophenyl)-7-(2,5-dimethyl-2,5-dihydro-1H-pyrrol-1-yl)[1,2,4]triazolo[1,5-a]pyrimidine;
5-chloro-6-(2-chloro-6-fluorophenyl)-7-(2-ethyl-1H-imidazol-1-yl)[1,2,4]triazolo[1,5-a]pyrimidine;
7-(4-bromo-1-piperidinyl)-5-chloro-6-(2-chloro-6-fluorophenyl)[1,2,4]triazolo[1,5-a]pyrimidine;
5-chloro-6-(2-methylphenyl)-7-(4-thiomorpholinyl)[1,2,4]triazolo[1,5-a]pyrimidine;
6-(2-bromophenyl)-N-(sec-butyl)-5-chloro[1,2,4]triazolo[1,5-a]pyrimidin-7-amine;
5-chloro-N-ethyl-6-(4-methoxyphenyl)-N-(2-methyl-2-propenyl)[1,2,4]triazolo[1,5-a]pyrimidin-7-amine;
5-chloro-6-(4-methoxyphenyl)-7-(4-thiomorpholinyl)[1,2,4]triazolo[1,5-a]pyrimidine;
5-chloro-7-(4-chloro-1-piperidinyl)-6-[2-(trifluoromethyl)phenyl][1,2,4]triazolo[1,5-a]pyrimidine;
5-chloro-6-(2-chloro-6-fluorophenyl)-7-[4-(trifluoromethyl)-1-piperidinyl][1,2,4]triazolo[1,5-a]pyrimidine;
7-(4-bromo-1-piperidinyl)-5-chloro-6-(2,6-difluorophenyl)[1,2,4]triazolo[1,5-a]pyrimidine;
7-(4-bromo-1-piperidinyl )-5-chloro-6-(2-chlorophenyl)[1,2,4]triazolo[1,5-a]pyrimidine;
5-chloro-N-ethyl-N-(2-methyl-2-propenyl)-6-(2,4,6-trifluorophenyl)[1,2,4]triazolo[1,5-a]pyrimidin-7-amine;
5-chloro-N-isopropyl-6-(2,4,6-trifluorophenyl)[1,2,4]triazolo[1,5-a]pyrimidin-7-amine;
5-chloro-7-(4-thiomorpholinyl)-6-(2,4,6-trifluorophenyl)[1,2,4]triazolo[1,5-a]pyrimidine;
7-(1-azepanyl)-5-chloro-6-(2,4,6-trifluorophenyl)[1,2,4]triazolo[1,5-a]pyrimidine;
5-chloro-6-(2-chloro-6-fluorophenyl)-7-[2-(1-pyrrolidinyl)-1-cyclopenten-1-yl][1,2,4]triazolo[1,5-a]pyrimidine;
5-chloro-7-(4-isopropyl-1-piperidinyl)-6-(4-methoxyphenyl)[1,2,4]triazolo[1,5-a]pyrimidine;

5-chloro-7-(2,4-dimethyl-1-piperidinyl)-6-(4-methoxyphenyl)[1,2,4]triazolo[1,5-a]pyrimidine;
5-chloro-7-[ethyl (2-methyl -2-propenyl )amino]-6-{4-nitrophenyl}[1,2,4]triazolo[1,5-a]pyrimidine;
7-(1-azepanyl)-5-chloro-6-{4-nitrophenyl}[1,2,4]triazolo[1, 5-a]pyrimidine;
N-bicyclo[2.2. 1]hept-2-yl-5-chloro-6-(2,4,6-trifluorophenyl)[1,2,4]triazolo[1,5-a]pyrimidin-7-amine;
5-chloro-6-(2,6-difluorophenyl)-N-(2,2,2-trifluoroethyl)[1,2,4]triazolo[1,5-a]pyrimidin-7-amine;
5chloro-6-(2-chlorophenyl)-N-(2,2,2-trifluoroethyl)[1,2,4]triazolo[1,5-a]pyrimidin-7-amine;
5-chloro-6-(2-chloro-6-fluorobenzyl)-7-tetrahydro-2-furanyl[1,2,4]triazolo[1,5-a]pyrimidine;
7-(allylsulfanyl)-5-chloro-6-(2-chloro-6-fluorophenyl)[1,2, 4]triazolo[1,5-a]pyrimidine;
5-chloro-N-ethyl-6-mesityl-N-(2-methyl-2-propenyl)[1,2,4]triazolo[1,5-a]pyrimidin-7-amine;
5-chloro-N-ethyl-6-(2-methoxyphenyl)-N-(2-methyl-2-propenyl)[1,2,4]triazolo[1,5-a]pyrimidin-7-amine;
5-chloro-6-(2-chloro-6-fluorophenyl)-N-hexyl[1,2,4]triazolo[1,5-a]pyrimidin-7-amine;
5-chloro-7-(4-methyl-1-piperidinyl)-6-[4-(methylsulfanyl)phenyl][1,2,4]triazolo[1,5-a]pyrimidine;
5-chloro-N-ethyl-N-(2-methyl-2-propenyl)-6-[4-(methylsulfanyl)phenyl][1,2,4]triazolo[1,5-a]pyrimidin-7-amine;
N-(sec-butyl)-5-chloro-6-[4-(methylsulfanyl)phenyl][1,2,4]triazolo[1,5-a]pyrimidin-7-amine;
5-chloro-6-[4-(methylsulfanyl)phenyl]-7-(4-thiomorpholinyl)[1,2,4]triazolo[1,5-a]pyrimidine;
5-chloro-6-[2,6-dichloro-4-(trifluoromethyl)phenyl]-7-(4-methyl-1-piperidinyl)[1,2,4]triazolo[1,5-a]pyrimidine;
7-(1-azepanyl)-5-chloro-6-[2,6-dichloro-4-(trifluoromethyl)phenyl][1,2,4]triazolo[1,5-a]pyrimidine;
5-chloro-6-(2-chloro-6-fluorophenyl)-7-[(2,2,2-trifluoroethyl)sulfanyl][1,2,4]triazolo[1,5-a]pyrimidine;
5-chloro-6-(2-chloro-6-fluorophenyl)-7-(4,4-dimethyl-1-piperidinyl)[1,2,4]triazolo[1,5-a]pyrimidine;
5-chloro-6-[2,6-dichloro-4-(trifluoromethyl)phenyl]-N-ethyl-N-(2-methyl-2-propenyl)[1,2,4]triazolo[1,5-a]pyrimidin-7-amine;
5-chloro-6-[2,6-dichloro-4-(trifluoromethyl)phenyl]-7-(4-thiomorpholinyl)[1,2,4]triazolo[1,5-a]pyrimidine;
5-chloro-6-(3,5-difluorophenyl)-7-(4-methyl-1-piperidinyl)[1,2,4]triazolo[1,5-a]pyrimidine;
5-chloro-6-(2-chloro-6-fluorophenyl)-7-(isopropylsulfanyl)[1,2,4]triazolo[1,5-a]pyrimidine;
5-chloro-6-(2-chloro-6-fluorophenyl)-7-tetrahydro-2-furanyl[1,2,4]triazolo[1,5-a]pyrimidine;
4-[5-chloro-7-(4-methyl-1-piperidinyl)[1,2,4]triazolo[1,5-a]pyrimidin-6-yl]aniline;
N-{4-[5-chloro-7-(4-methyl-1-piperidinyl)[1,2,4]triazolo[1, 5-a]pyrimidin-6-yl]phenyl}acetamide;
[5-chloro-6-(2-chloro-6-fluorophenyl)[1,2,4]triazolo[1,5-a]pyrimidin-7-yl]methyl acetate;
5-chloro-6-(2-chloro-6-fluorophenyl)-7-(chloromethyl)[1,2, 4]triazolo[1,5-a]pyrimidine;
diethyl 2-[6-(2-chloro-6-fluorophenyl)-7-(4-methyl-1-piperidinyl)[1,2,4]triazolo[1,5-a]pyrimidin-5-yl]malonate;
7-(1-azepanylmethyl)-5-chloro-6-(2-chloro-6-fluorophenyl) [1,2,4]triazolo[1,5-a]pyrimidine;
N-allyl-5-chloro-6-(2-chloro-6-fluorophenyl)-N-hexyl[1,2, 4]triazolo[1,5-a]pyrimidin-7-amine;
5-chloro-7-(4-methyl-1-piperidinyl)-6-[4-(trifluoromethoxy)phenyl][1,2,4]triazolo[1,5-a]pyrimidine;
5-chloro-7-(4-methyl-1-piperidinyl)-6-(4-phenoxyphenyl) [1,2,4]triazolo[1,5-a]pyrimidine;

5-chloro-6-(2-chloro-6-fluorophenyl)-N-(cyclopropylmethyl)-N-propyl[1,2,4]triazolo[1,5-a]pyrimidin-7-amine;
5-chloro-7-(2-methyl-1-piperidinyl)-6-(4-phenoxyphenyl) [1,2,4]triazolo[1,5-a]pyrimidine;
5-chloro-6-{2-chloro-4-nitrophenyl}-7-(4-methyl-1-piperidinyl)[1,2,4]triazolo[1,5-a]pyrimidine;
5-chloro-6-(4-chloro-2,3,5,6-tetrafluorophenyl)-N-cyclopentyl[1,2,4]triazolo[1,5-a]pyrimidin-7-amine;
4-[5-chloro-2-methyl-7-(4-methyl-1-piperidinyl)[1,2,4]triazolo[1,5-a]pyrimidin-6-yl]-N,N-dimethylaniline;
6-(2-chloro-6-fluorophenyl)-5-methyl-7-(4-methyl-1-piperidinyl)[1,2,4]triazolo[1,5-a]pyrimidine;
5-chloro-6-(2-chloro-6-fluorophenyl)-7-[2-(1-pyrrolidinyl)-1-cyclohexen-1-yl][1,2,4]triazolo[1,5-a]pyrimidine;
5-chloro-6-(2-chloro-6-fluorophenyl)-7-(methoxymethyl) [1,2,4]triazolo[1,5-a]pyrimidine;
5-chloro-6-{2-chloro-4-nitrophenyl}-7-[ethyl(2-methyl-2-propenyl)amino][1,2,4]triazolo[1,5-a]pyrimidine;
5-bromo-6-(2-chloro-6-fluorophenyl)-7-(isopropylsulfanyl) [1,2,4]triazolo[1,5-a]pyrimidine;
5-chloro-N-cyclopentyl-6-(4-ethoxy-2,3,5,6-tetrafluorophenyl)[1,2,4]triazolo[1,5-a]pyrimidin-7-amine;
5-chloro-N-methyl-N-(2-methyl-2-propenyl)-6-(2,4,6-trifluorophenyl)[1,2,4]triazolo[1,5-a]pyrimidin-7-amine;
4-bromo-1-[5-chloro-6-(2-chloro-6-fluorophenyl)[1,2,4]triazolo[1,5-a]-pyrimidin-7-yl]butyl acetate;
diethyl 2-allyl-2-{[5-chloro-6-(2-chloro-6-fluorophenyl)[1, 2,4]triazolo[1,5-a]pyrimidin-7-yl]oxy}malonate;
6-(2-chloro-6-fluorophenyl)-N-ethyl-5-methyl[1,2,4]triazolo[1,5-a]pyrimidin-7-amine;
N-butyl-5-chloro-N-ethyl-6-(2,3,4,5,6-pentafluorophenyl) [1,2,4]triazolo[1,5-a]pyrimidin-7-amine;
6-(2-chloro-6-fluorophenyl)-5-(difluoromethoxy)-7-(4-methyl-1-piperidinyl)[1,2,4]triazolo[1,5-a]pyrimidine;
5-chloro-6-(2-chloro-6-fluorophenyl)-7-[(4-chlorophenyl) sulfanyl][1,2,4]triazolo[1,5-a]pyrimidine;
5-chloro-6-(2-chloro-6-fluorophenyl)-7-[(2-methoxyphenyl)sulfanyl][1,2,4]triazolo[1,5-a]pyrimidine;
5-chloro-6-(2-chloro-6-fluorophenyl)-N-(1,2,2-trimethylpropyl)[1,2,4]triazolo[1,5-a]pyrimidin-7-amine;
5-chloro-6-(2,3,4,5,6-pentafluorophenyl)-N-(1,2,2-trimethylpropyl)[1,2,4]triazolo[1,5-a]pyrimidin-7-amine;
5-chloro-6-(2,4,6-trifluorophenyl)-N-(1,2,2-trimethylpropyl)[1,2,4]triazolo[1,5-a]pyrimidin-7-amine;
5-chloro-6-(4-fluorophenyl)-N-(1,2,2-trimethylpropyl)[1,2, 4]triazolo[1,5-a]pyrimidin-7-amine;
5,7-bis(4-methyl-1-piperidinyl)-6-(2,4,6-trifluorophenyl)[1, 2,4]triazolo[1,5-a]pyrimidine;
5-chloro-6-(2-methylphenyl)-N-(1,2,2-trimethylpropyl)[1, 2,4]triazolo[1,5-a]pyrimidin-7-amine;
5-chloro-6-(2,4,5-trifluorophenyl)-N-(1,2,2-trimethylpropyl)[1,2,4]triazolo[1,5-a]pyrimidin-7-amine;
6-(2-bromophenyl)-5-chloro-N-(1,2,2-trimethylpropyl)[1,2, 4]triazolo[1,5-a]pyrimidin-7-amine;
5-chloro-N-isobutyl-N-(2,2,2-trifluoroethyl)-6-(2,4,6-trifluorophenyl)[1,2,4]triazolo[1,5-a]pyrimidin-7-amine;
5-chloro-N-isobutyl-6-(2-methylphenyl)-N-(2,2,2-trifluoroethyl)[1,2,4]triazolo[1,5-a]pyrimidin-7-amine;
5-chloro-6-(2-chloro-6-fluorophenyl)-N-(2,2,2-trifluoro-1-methylethyl)[1,2,4]triazolo[1,5-a]pyrimidin-7-amine;
5-chloro-6-(2,6-difluorophenyl)-N-(2,2,2-trifluoro-1-methylethyl)[1,2,4]triazolo[1,5-a]pyrimidin-7-amine;
5-chloro-N-(2,2,2-trifluoro-1-methylethyl)-6-(2,4,6-trifluorophenyl)[1,2,4]triazolo[1,5-a]pyrimidin-7-amine;
N-allyl-5-chloro-N-isobutyl-6-(2,4,6-trifluorophenyl)[1,2, 4]triazolo[1,5-a]pyrimidin-7-amine;

5-chloro-N-(1,2-dimethylpropyl)-6-(2,4,6-trifluorophenyl)[1,2,4]triazolo[1,5-a]pyrimidin-7-amine;
5-chloro-N-isopropyl-N-methyl-6-(2,4,6-trifluorophenyl)[1,2,4]triazolo[1,5-a]pyrimidin-7-amine;
5-chloro-N-isopropyl-N-(2,2,2-trifluoroethyl)-6-(2,4,6-trifluorophenyl)[1,2,4]triazolo[1,5-a]pyrimidin-7-amine;
7-butyl-5-chloro-6-(2,4,6-trifluorophenyl)[1,2,4]triazolo[1,5-a]pyrimidine;
5-chloro-N-(1-phenylethyl)-6-(2,4,6-trifluorophenyl)[1,2,4]triazolo[1,5-a]pyrimidin-7-amine;
5-chloro-6-(2-chlorophenyl)-N-(2,2,2-trifluoro-1-methylethyl)[1,2,4]triazolo[1,5-a]pyrimidin-7-amine;
5-chloro-N-ethyl-N-isobutyl-6-(2,4,6-trifluorophenyl)[1,2,4]triazolo[1,5-a]pyrimidin-7-amine;
5-chloro-6-(2-chloro-6-fluorophenyl)-7-hexyl[1,2,4]triazolo[1,5-a]pyrimidine;
5-chloro-6-(2-methylphenyl)-N,N-bis(2,2,2-trifluoroethyl)[1,2,4]triazolo[1,5-a]pyrimidin-7-amine;
5-chloro-N-cyclopentyl-N-methyl-6-(2,3,4,5,6-pentafluorophenyl)[1,2,4]triazolo[1,5-a]pyrimidin-7-amine;
7-butyl-5-chloro-6-(2,6-difluorophenyl)[1,2,4]triazolo[1,5-a]pyrimidine;
5-chloro-N-(1,2-dimethylpropyl)-N-methyl-6-(2,3,4,5,6-pentafluorophenyl)[1,2,4]triazolo[1,5-a]pyrimidin-7-amine;
5-chloro-6-(2-chloro-6-fluorophenyl)-7-phenyl[1,2,4]triazolo[1,5-a]pyrimidine;
5-chloro-6-(2-chloro-6-fluorophenyl)-7-(2-methylpropanyl)[1,2,4]triazolo[1,5-a]pyrimidine;
5-chloro-6-(2-chloro-6-fluorophenyl)-7-pentyl[1,2,4]triazolo[1,5-a]pyrimidine;
5-chloro-N-(1,2-dimethylpropyl)-N-methyl-6-(2,4,6-trifluorophenyl)[1,2,4]triazolo[1,5-a]pyrimidin-7-amine;
5-chloro-6-(2-chloro-6-fluorophenyl)-7-cyclohexyl[1,2,4]triazolo[1,5-a]pyrimidine;
5-chloro-6-(2-bromo-5-chlorophenyl)-N-(2,2,2-trifluoro-1-methylethyl)[1,2,4]triazolo[1,5-a]pyrimidin-7-amine;
5-chloro-6-(2-chloro-6-fluorophenyl)-7-(3,3,3-trifluoropropyl)[1,2,4]triazolo[1,5-a]pyrimidine;
5-chloro-6-(2-chloro-6-fluorophenyl)-7-(3-methylphenyl)[1,2,4]triazolo[1,5-a]pyrimidine;
[5-chloro-6-(2,4,6-trifluorophenyl)-[1,2,4]triazolo[1,5-a]pyrimidin-7-yl]-(1-p-tolyl-ethyl)-amine;
5-chloro-6-(2,4,6-trifluoro-phenyl)-7-cyclohexyl[1,2,4]triazolo[1,5-a]pyrimidine;
5-chloro-7-cyclohexyl-6-(2,3,4,5,6-pentafluorophenyl)[1,2,4]triazolo[1,5-a]pyrimidine;
5-chloro-6-(2-chloro-6-fluorophenyl)-7-(4,4-difluoro-1-piperidinyl)[1,2,4]triazolo[1,5-a]pyrimidine;
7-(bicyclo[2.2.1]hept-2-ylamino)-5-chloro-6-{2-fluoro-4-nitrophenyl}[1,2,4]triazolo[1,5-a]pyrimidine;
5-chloro-6-{2-fluoro-4-nitrophenyl}-7-(4-methyl-1-piperidinyl)[1,2,4]triazolo[1-a]pyrimidine;
5-(methylsulfanyl)-6-(2-chloro-6-fluorophenyl)-7-cyclohexyl[1,2,4]triazolo[1,5-a]pyrimidine;
[5-chloro-6-(2,4,6-trifluorophenyl)[1,2,4]triazolo[1,5-a]pyrimidin-7-yl] (2,2,2-trifluoro-1-phenylethyl)-amine;
5-chloro-N-[1-(trifluoromethyl)propyl]-6-(2,4,6-trifluorophenyl)[1,2,4]triazolo[1,5-a]pyrimidin-7-amine;
5-bromo-6-(2-chloro-6-fluorophenyl)-7-cyclohexyl[1,2,4]triazolo[1,5-a]pyrimidine;
6-(2-chloro-6-fluorophenyl)-7-cyclohexyl[1,2,4]triazolo[1,5-a]pyrimidin-5-amine;
[5-chloro-6-(2,4,6-trifluorophenyl)[1,2,4]triazolo[1,5-a]pyrimidin-7-yl]-(2-methyl-1-trifluoromethyl-propyl)amine;
5-chloro-7-(3-cyclohexen-1-yl)-6-(2,4,6-trifluorophenyl)[1,2,4]triazolo[1,5-a]pyrimidine;
5-chloro-7-(1-cyclohexen-1-yl)-6-(2,4,6-trifluorophenyl)[1,2,4]triazolo[1,5-a]pyrimidine;
5-chloro-N-[(1R)-2,2,2-trifluoro-1-methylethyl]-6-(2,4,6-trifluorophenyl)[1,2,4]triazolo[1,5-a]pyrimidin-7-amine;
5-chloro-N-[(1S)-2,2,2,-trifluoro-1-methylethyl]-6-(2,4,6,-trifluorophenyl)[1,2,4]triazolo[1,5-a]pyrimidin-7-amine;
6-(2,4-difluorophenyl)-5-chloro-N-(2,2,2-trifluoro-1-methylethyl)[1,2,4]triazolo[1,5-a]pyrimidin-7-amine;
5-chloro-6-(2,6-difluoro-4-methoxyphenyl)-7-(4-methyl-1-piperidinyl)[1,2,4]triazolo[1,5-a]pyrimidine;
5-chloro-6-(2,6-difluoro-4-methoxyphenyl)-N-(2,2,2-trifluoro-1-methylethyl)[1,2,4]triazolo[1,5-a]pyrimidin-7-amine;
5-chloro-7-cyclohexyl-6-(2,6-difluoro-4-methoxyphenyl)[1,2,4]triazolo[1,5-a]pyrimidine;
5-chloro-6-(2,6-difluoro-4-methoxyphenyl)-N-[(1S)-2,2,2-trifluoro-1-methylethyl][1,2,4]triazolo[1,5-a]pyrimidin-7-amine;
7-cyclohexyl-6-(2,6-difluoro-4-methoxyphenyl)-5-methoxy[1,2,4]triazolo[1,5-a]pyrimidine;
5-chloro-7-(4-fluorocyclohexyl )-6-(2,4,6-trifluorophenyl)[1,2,4]triazolo[1,5-a]pyrimidine;
5-chloro-6-(2,6-dichloro-4-fluorophenyl)-7-(3,3,3-trifluoropropyl)[1,2,4]triazolo[1,5-a]pyrimidin-7-amine;
N-(sec-butyl)-5-chloro-6-(2,6-dichloro-4-fluorophenyl)[1,2,4]triazolo[1,5-a]pyrimidin-7-amine;
4-{5-chloro-7-[(2,2,2-trifluoro-1-methylethyl)amino][1,2,4]triazolo[1,5-a]pyrimidin-6-yl}-3,6-difluorophenol;
5-chloro-7-(3-cyclohexen-1-yl)-6-(2,6-difluoro-4-methoxyphenyl)[1,2,4]triazolo[1,5-a]pyrimidine;
5-chloro-6-(2,6-difluoro-4-methoxyphenyl)[1,2,4]triazolo[1,5-a]pyrimidin-7-amine;
5-chloro-N-cyclopentyl-6-(2,6-difluoro-4-methoxyphenyl)[1,2,4]triazolo[1,5-a]pyrimidin-7-amine;
5-chloro-6-(2,6-difluoro-4-methoxyphenyl)-7-(3,6-dihydro-1(2H)-pyridinyl)[1,2,4]triazolo[1,5-a]pyrimidine;
5-chloro-6-(2,6-difluoro-4-methoxyphenyl)-7-(4-thiomorpholinyl)[1,2,4]triazolo[1,5-a]pyrimidine;
7-(1-azepanyl)-5-chloro-6-(2,6-difluoro-4-methoxyphenyl)[1,2,4]triazolo[1,5-a]pyrimidine;
5-chloro-6-(2,6-difluoro-4-methoxyphenyl)-N-(1,2,2-trimethylpropyl)[1,2,4]triazolo[1,5-a]pyrimidin-7-amine;
5-chloro-6-(2,6-difluoro-4-methoxyphenyl)-N-ethyl-N-(2-methyl-2-propenyl)[1,2,4]triazolo[1,5-a]pyrimidin-7-amine;
5-chloro-6-(2,6-difluoro-4-methoxyphenyl)-7-(4-fluorocyclohexyl)[1,2,4]triazolo[1,5-a]pyrimidine;
6-(4-{5-chloro-7-[(2,2,2-trifluoro-1-methylethyl)amino][1,2,4]triazolo[1,5-a]pyrimidin-6-yl}-3,5-difluorophenoxy) hexanoic acid;
2,6-difluoro-4-(2-fluoroethoxy)phenyl]-N-(2,2,2-trifluoro-1-methylethyl)[1,2,4]triazolo[1,5-a]pyrimidin-7-amine;
5-chloro-N-isopropyl-6-{2-[(trifluoromethyl)sulfanyl]phenyl}[1,2,4]triazolo[1,5-a]pyrimidin-7-amine;
5-chloro-N-[4-(trifluoromethyl)phenyl]-6-(2,4,6-trifluorophenyl)[1,2,4]triazolo[1,5-a]pyrimidin-7-amine;
5-chloro-N-(4,4,4-trifluoro-2-methylbutyl)-6-(2,4,6-trifluorophenyl)[1,2,4]triazolo[1,5-a]pyrimidin-7-amine;
5-chloro-6-(2,6-difluoro-4-methoxyphenyl)-7-(3-methyl-3-butenyl)[1,2,4]triazolo[1,5-a]pyrimidine;
5-chloro-6-(2,6-difluoro-4-methoxyphenyl)-7-isobutyl[1,2,4]triazolo[1,5-a]pyrimidine;
7-cyclopentyl-6-(2,6-difluoro-4-methoxyphenyl)-5-methoxy[1,2,4]triazolo[1,5-a]pyrimidine;
5-chloro-6-(2-thienyl)-N-[(1R)-2,2,2-trifluoro-1-methylethyl[1,2,4]triazolo[1,5-a]pyrimidin-7-amine;

4-[5-chloro-7-(2,2,2-trifluoro-1-methyl-ethylamino)[1,2,4]triazolo[1,5-a]pyrimidin-6-yl]-3,5-difluoro-phenol;
{5-chloro-6-[2,6-difluoro-4-(2,2,2-trifluoro-ethoxy)-phenyl]-[1,2,4]triazolo[1,5-a]pyrimidin-7-yl}-(2,2,2-trifluoro-1-methyl-ethyl)amine;
5-chloro-6-(2,6-difluoro-4-methoxyphenyl)-N-(2,2,2-trifluoro-1-methylethyl)[1,2,4]triazolo[1,5-a]pyrimidin-7-amine;
(5-chloro-6-{4-[2-(2-ethoxyethoxy)-ethoxy]-2,6-difluorophenyl}[1,2,4]triazolo[1,5-a]pyrimidin-7-yl-)-(2,2,2-trifluoro-1-methylethyl)amine;
(5-chloro-6-{2,6-difluoro-4-[2-(2-methoxy-ethoxy)ethoxy]-phenyl}-[1,2,4]triazolo[1,5-a]pyrimidin-7-yl-)-(2,2,2-trifluoro-1-methylethyl)amine;
{5-chloro-6-[2,6-difluoro-4-(furan-3-ylmethoxy)phenyl][1,2,4]triazolo[1,5-a]pyrimidin-7-yl}-N-(2,2,2-trifluoro-1-methylethyl)amine;
5-chloro-6-(2,5-difluoro-4-methoxyphenyl)-N-(1,2,2-trimethylpropyl)[1,2,4]triazolo[1,5-a]pyrimidin-7-amine;
7-cyclohexyl-6-[2,6-difluoro-4-(2-methoxyethoxy)phenyl]-5-methoxy[1,2,4]triazolo[1,5-a]pyrimidine;
5-chloro-6-(2-fluoro-4-methoxy-6-chlorophenyl)-N-(2,2,2-trifluoro-1-methylethyl)[1,2,4]triazolo[1,5-a]pyrimidin-7-amine;
5-chloro-6-[2,6-difluoro-4-(2-fluoroethoxy)phenyl]-N-ethyl-N-(2-methyl-2-propenyl)[1,2,4]triazolo[1,5-a]pyrimidin-7-amine;
2-[2-(4-{5-chloro-7-[(2,2,2-trifluoro-1-methylethyl)amino][1,2,4]triazolo[1,5-a]pyrimidin-6-yl}-3,5-difluorophenoxy)ethoxy]ethanol;
5-chloro-6-(2,3-difluoro-4-methoxyphenyl)-N-(2,2,2-trifluoro-1-methylethyl)[1,2,4]triazolo[1,5-a]pyrimidin-7-amine;
5-chloro-6-{4-(2-fluoroethoxy)-2,6-difluorphenyl}-N-(2,2,2-trifluoro-1-methylethyl)[1,2,4]triazolo[1,5-a]pyrimidin-7-amine;
5-chloro-N-(4-chlorobenzyl)-6-(2-chloro-6-fluorophenyl)[1,2,4]triazolo[1,5-a]pyrimidin-7-amine;
5-chloro-6-(2-chloro-6-fluorophenyl)-7-[4-(2-pyridinyl)-1-piperazinyl][1,2,4]triazolo[1,5-a]pyrimidine;
5-chloro-6-(2-chloro-6-fluorophenyl)-N-(1-ethylpentyl)[1,2,4]triazolo[1,5-a]pyrimidin-7-amine;
5-chloro-6-(2-chloro-6-fluorophenyl)-7-[4-(2-chlorophenyl)-1-piperazinyl][1,2,4]triazolo[1,5-a]pyrimidine;
5-chloro-6-(2-chloro-6-fluorophenyl)-7-[4-(4-methoxyphenyl)-3-methyl-1-piperazinyl][1,2,4]triazolo[1,5-a]pyrimidine;
5-chloro-N-cyclopentyl-6-(2-chloro-6-fluorophenyl)[1,2,4]triazolo[1,5-a]pyrimidin-7-amine;
5-chloro-7-phenoxy-6-(4-methoxy-phenyl)[1,2,4]triazolo[1,5-a]pyrimidine;
5-chloro-N-cyclopentyl-6-(4-methylphenyl)[1,2,4]triazolo[1,5-a]pyrimidin-7-amine;
5,7-diphenoxy-6-(4-methoxyphenyl)[1,2,4]triazolo[1,5-a]pyrimidine;
5-chloro-N-cyclopentyl-6-(2-chlorophenyl)[1,2,4]triazolo[1,5-a]pyrimidin-7-amine;
5-chloro-N,N-diethyl-6-[4-methoxyphenyl][1,2,4]triazolo[1,5-a]pyrimidin-7-amine;
5-chloro-N,N-diethyl-6-[2,4-dichlorophenyl][1,2,4]triazolo[1,5-a]pyrimidin-7-amine;
N-bicyclo[2.2.1]hept-2-yl-5-chloro-6-(2,4-dichlorophenyl)[1,2,4]triazolo[1,5-a]pyrimidin-7-amine;
5-chloro-6-(2-chloro-6-fluorophenyl)-7-(1,4-dioxa-8-azaspiro[4.5]dec-8-yl)[1,2,4]triazolo[1,5-a]pyrimidine;
5-cyano-7-(4-methyl-1-piperidinyl)-6-(2-chloro-5-fluorophenyl)[1,2,4]triazolo[1,5-a]pyrimidine;
5-(methylsulfanyl)-7-(4-methyl-1-piperidinyl)-6-(2-chloro-6-fluorophenyl)[1,2,4]triazolo[1,5-a]pyrimidine;
5-(methylsulfanyl)-7-(4-methyl-1-piperidinyl)-6-(2-chloro-5-(methylsulfanyl)phenyl)[1,2,4]triazolo[1,5-a]pyrimidine;
5-chloro-7-(1,4-dioxa-8-azaspiro[4.5]dec-8-yl)-6-(4-methoxyphenyl)[1,2,4]triazolo[1,5-a]pyrimidine;
5-chloro-N-ethyl-N-(2-methyl-2-propenyl)-6-(4-(methylsulfanyl)phenyl)[1,2,4]triazolo[1,5-a]pyrimidin-7-amine;
2-methyl-6,7-di-(4-methoxyphenyl)[1,2,4]triazolo[1,5-a]pyrimidine;
2-methyl-6-phenyl-7-(4-chlorophenyl)[1,2,4]triazolo[1,5-a]pyrimidine;
2-trifluoromethyl-6-phenyl-7-(4-methoxyphenyl)[1,2,4]triazolo[1,5-a]pyrimidine;
5,7-diphenoxy-6-(2-methylpropyl)[1,2,4]triazolo[1,5-a]pyrimidine;
5-chloro-6-(3,4-difluorophenyl)-N-(isopropyl)[1,2,4]triazolo[1,5-a]pyrimidin-7-amine;
5-bromo-6-(4-bromophenyl)-7-dimethylamino[1,2,4]triazolo[1,5-a]pyrimidine;
5-bromo-6-(4-trifluoromethylphenyl)-7-dimethylamino[1,2,4]triazolo[1,5-a]pyrimidine;
5-chloro-6-(3,4-difluorophenyl)-7-dimethylamino[1,2,4]triazolo[1,5-a]pyrimidine;
5-chloro-6-(4-trifluoromethylphenyl)-N-(ethyl)[1,2,4]triazolo[1,5-a]pyrimidin-7-amine;
7-(1-azepanyl)-5-chloro-6-(4-tert-butylphenyl )[1,2,4]triazolo[1,5-a]pyrimidine;
ethyl {[5-chloro-6-(2-chloro-6-fluorophenyl)[1,2,4]triazolo[1,5-a]pyrimidin-7-yl]amino}acetate;
diethyl 5-chloro-6-(2,6-difluorophenyl)[1,2,4]triazolo[1,5-a]pyrimidin-7-malonate;
5-chloro-6-(2,5-difluorophenyl)-N-(3-methyl-2-butenyl)[1,2,4]triazolo[1,5-a]pyrimidin-7-amine;
[5-chloro-6-(2-chloro-6-fluorophenyl)-[1,2,4]triazolo[1,5-a]pyrimidin-7-yl]acetic -acid methyl ester;
5-chloro-6-(2,6-difluorophenyl)-7-(2-ethyl-1H-imidazol-1-yl)[1,2,4]triazolo[-1,5a]pyrimidine;
5-chloro-N,N-diethyl-6-[4-(methylsulfanyl)phenyl][1,2,4]triazolo[1,5-a]pyrimidin-7-amine;
ethyl [6-(2-chloro-6-fluorophenyl)-7-(4-methyl-1-piperidinyl)-[1,2,4]triazolo[1,5-a]pyrimidin-5-yl]acetate;
5-chloro-N-ethyl-N-(2-methyl-2-propenyl)-6-(4-phenoxyphenyl)[1,2,4]triazolo[1,5-a]pyrimidin-7-amine;
dimethyl 2-[5-chloro-6-(2-chloro-6-fluorophenyl)[1,2,4]triazolo[1,5-a]pyrimidin-7yl]malonate;
diethyl 2-{[5-chloro-6-(2-chloro-6-fluorophenyl)[1,2,4]triazolo[1,5-a]pyrimidin-7-yl]oxy}-2-isobutylmalonate;
2-[5-chloro-6-(2-chloro-6-fluorophenyl)[1,2,4]triazolo[1,5-a]pyrimidin-7-yl]-1,3-cyclohexanedione;
2-[5-chloro-6-(2-chloro-6-fluorophenyl)[1,2,4]triazolo[1,5-a]pyrimidin-7-yl]cyclohexanone;
5-chloro-7-(3-nitro-4-methylanilino)-6-(2,4,6-trifluorophenyl) -[1,2,4]triazolo[1,5-a]pyrimidine;
7-cyclohexyl-6-[2,6-difluoro-4-(2-methoxyethoxy)phenyl] 5-(2-methoxyethoxy)[1,2,4]triazolo[1,5-a]pyrimidine;
7-(3-bromophenyl)-2-ethyl-6-(4-methoxyphenyl)[1,2,4]triazolo[1,5-a]pyrimidine;
7-(3-bromophenyl)-6-(3-chlorophenyl)-2-ethyl[1,2,4]triazolo[1,5-a]pyrimidine;
7-(4-bromophenyl)-2-ethyl-6-[4-(trifluoromethyl)phenyl][1,2,4]triazolo[1,5-a]pyrimidine;
5-chloro-6-(2-chloro-6-fluorophenyl)-N-(3,4,5-trimethoxybenzyl)[1,2,4]triazolo[1,5-a]pyrimidin-7-amine;
7-(2-benzyl-4,5-dihydro-1H-imidazol-1-yl)-5-chloro-6-(2-chloro-6-fluorophenyl)[1,2,4]triazolo[1,5-a]pyrimidine;

N-4-[5-chloro-6-(2-chloro-6-fluorophenyl)[1,2,4]triazolo[1,5-a]pyrimidin-7-yl-N,N-1-diethyl-1,4-pentanediamine;
5-chloro-N-(3-methyl-2-butenyl)-6-phenyl[1,2,4]triazolo[1,5-a]pyrimidin-7-amine;
5-dimethylamino-6-phenyl-N-cyclopentyl[1,2,4]triazolo[1,5-a]pyrimidin-7-amine;
5-chloro-7-[(2-furylmethyl)sulfanyl]-6-(4-methoxyphenyl)[1,2,4]triazolo[1,5-a]pyrimidine;
6-[1,1'-biphenyl]-4-yl-5-chloro-N-cyclopentyl[1,2,4]triazolo[1,5-a]pyrimidin-7-amine;
6-[4-(benzyloxy)phenyl]-5-chloro-N-isopropyl[1,2,4]triazolo[1,5-a]pyrimidin-7-amine;
5-chloro-N-[(2,2-dichlorocyclopropyl)methyl]-6-(3,4,5-trimethoxyphenyl)[1,2,4]triazolo[1,5-a]pyrimidin-7-amine;
N-cyclopentyl-6-(2-fluorophenyl )-5-hydrazino[1,2,4]triazolo[1,5-a]pyrimidin-7-amine;
5-chloro-N-ethyl-6-(2-methylphenyl)[1,2,4]triazolo[1,5-a]pyrimidin-7-amine;
6-(4-tert-butyl phenyl)-5-chloro-N-isopropyl[1,2,4]triazolo[1,5-a]pyrimidin-7-amine;
5-chloro-6-[2,6-difluoro-4-[(3-methyl-2-butenyl)oxy]phenyl]-N-(2,2,2-trifluoro-1-methylethyl)-I[1,2,4]triazolo[1,5-a]pyrimidin-7-amine;
5-chloro-6-[2,6-difluoro-4-(1-propenyloxy)phenyl]-N-(2,2,2-trifluoro-1-methylethyl)-I[1,2,4]triazolo[1,5-a]pyrimidin-7-amine;
5-chloro-N-(tricyclo[2.2.1.0$^{2,6}$]hept-1-yl)-6-(2,4,6-trifluorophenyl)1,2,4]triazolo[1,5-a]pyrimidin-7-amine;
5-azido-7-cyclohexyl-6-(2-fluoro-6-chlorophenyl) [1,2,4]triazolo[1,5-a]pyrimidine;
5-azido-6-[2-chloro-6-fluorophenyl]-7-(4-methyl-1-piperidinyl)[1,2,4]triazolo[1,5-a]pyrimidine;
2,5-dichloro-7-(4-methyl-1-piperidinyl)-6-[2-chloro-6-fluorophenyl][1,2,4]triazolo[1,5-a]pyrimidine.

It is understood that the definition of compounds of Formula (I), when $R^1$, $R^2$, $R^3$, $R^4$, $R^a$, $R^b$, $R^c$, $R^d$, or R' contain asymmetric carbons, encompass all possible stereoisomers and mixtures thereof which possess the activity discussed below. In particular, the definition encompasses racemic modifications and any optical isomers, (R) and (S), which possess the indicated activity. Optical isomers may be obtained in pure form by standard separation techniques or enantiomer specific synthesis. It is understood that this invention encompasses all crystalline forms of compounds of Formula (I).

The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where $R^1$, $R^2$, $R^3$, $R^4$, $R^a$, $R^b$, $R^c$, $R^d$, or R' contains a carboxyl group, salts of the compounds in this invention may be formed with bases such as alkali metals (Na, K, Li) or alkaline earth metals (Ca or Mg).

For the compounds defined above and referred to herein, unless otherwise noted, the following terms are defined.

The term halogen atom may denote a bromine, iodine, chlorine or fluorine atom, and is especially a bromine, chlorine or fluorine atom.

The terms alkyl, alkenyl, alkynyl, alkadienyl as used herein with respect to a radical or moiety refer to a straight or branched chain radical or moiety. As a rule, such radicals have up to 12, in particular up to 6 carbon atoms. Suitably an alkyl moiety has from 1 to 6 carbon atoms, preferably from 1 to 3 carbon atoms. A preferred alkyl moiety is an ethyl or especially a methyl group. Suitably an alkenyl moiety has from 2 to 12 carbon atoms. A preferred alkenyl moiety has from 2 to 6 carbon atoms. Most preferred is allyl or especially a 2-methylallyl group. Any of the alkyl, alkenyl, alkynyl, alkadienyl groups as used herein with respect to the radical or moiety may optionally be substituted with one or more of substituents which include for example, halogen atoms, nitro, cyano, thiocyanato, cyanato, hydroxyl, alkyl, haloalkyl, alkoxy, haloalkoxy, amino, alkylamino, dialkylamino, formyl, aryl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, especially furyl, and cycloalkyl, especially cyclopropyl, groups. Typically, 0-3 substituents may be present.

Cycloalkyl or cycloalkenyl as used herein with respect to a radical or moiety refer to a cycloalkyl or cycloalkenyl group having 3 to 8 carbon atoms preferably 3 to 6 carbon atoms or a cycloalkenyl group having 5 to 8 carbon atoms, preferably 5 to 7 carbon atoms, in particular cyclopentyl, cyclohexyl or cyclohexenyl being optionally substituted by one or more of substituents which include for example, halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, especially furyl, and cycloalkyl, especially cyclopropyl, groups. Typically, 0-3 substituents may be present. Optionally, —CH$_2$— group of the cycloalkyl or cycloalkenyl radical or moiety may optionally be replaced with —O—, —S— or —NR' where R' is H or an alkyl group of 2 to 12 carbon atoms.

A bicycloalkyl group may contain from 5 to 10 carbon atoms.

Aryl as used herein with respect to the radical or moiety refers to an aryl group having 6, 10 or 14 carbon atoms, preferably 6 to 10 carbon atoms, in particular, phenyl, or naphthyl group being optionally substituted by one or more independently selected substituents which include, halogen atoms, nitro, cyano, alkenyl, thiocyanato, cyanato, hydroxyl, alkyl, haloalkyl, alkoxy, alkenyloxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, and cycloalkyl, groups. Typically, 0-5 substituents may be present.

Aralkyl as used herein means an aryl-alkyl group in which the aryl and alkyl group are previously defined. Exemplary aralkyl groups include benzyl and phenethyl.

Aralkyloxy as used herein refers to an aryl-alkyl-O— group in which the alkyl group and aryl group are previously described.

Phenyl as used herein refers to a 6-membered aromatic ring.

Heterocyclyl group may be a single ring, a bicyclic ring system or a system of annelated or spiro-fused rings as a saturated or unsaturated moiety or radical having 3 to 12 ring atoms with 5 to 8 ring atoms preferred with 5 or 6 ring atoms more preferred selected from carbon, oxygen, sulfur and nitrogen, one or more, typically one or two, of which being oxygen, nitrogen or sulfur, being optionally substituted by one or more of substituents which include for example, halogen atoms, preferably fluorine, nitro, cyano, thiocyanato, cyanato, hydroxyl, alkyl of 1 to 12 carbon atoms, preferably 1 to 6 carbon atoms, haloalkyl, preferably haloalkyl of 1 to 6 carbon atoms, alkoxy, alkoxy of 1 to 12 carbon atoms, preferably alkoxy of 1 to 6 carbon atoms, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, especially furyl, and cycloalkyl, especially cyclopropyl, groups. Typically, 0-3 substituents may be present. Optionally substituted heterocyclyl groups include pyrrolodinyl, pyrrazolidinyl, piperidinyl, piperazinyl or morpholin-4-yl, pyridinyl, 2,3-dehydropiperid-3-yl, tetrahydropyranyl, tetrahydrofuranyl or tetrahydrothienyl, N-methyl-2,3-dehydropiperid-3-yl. pyrimidinyl, pyrrolidinyl, furyl, pyranyl, morpholinyl, tetrahydropyridine, thienyl, pyrrolidinyl, piperidyl, dihydropiperidyl, dihydropyridinyl, thiazanyl, morpholinyl, thiazinyl, azepanyl, azocanyl and dioxa-aza-spiro-decyl.

When any of the foregoing substituents are designated as being optionally substituted, the substituent groups which are optionally present may be any one or more of substituents which include for example, halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, especially furyl, and cycloalkyl, especially cyclopropyl, groups. Typically, 0-3 substituents may be present. When any of the foregoing substituents represents or contains an alkyl substituent group, this may be linear or branched and may contain up to 12, preferably up to 6, and especially up to 4, carbon atoms. When any of the foregoing substituents represents or contains an aryl or cycloalkyl moiety, the aryl or cycloalkyl moiety may itself be substituted by one or more halogen atoms, nitro, cyano, alkyl, haloalkyl, alkoxy or haloalkoxy groups. In the case of cycloalkyl and heterocyclyl groups, optional substituents also include groups which together with two adjacent carbon atoms of the cycloalkyl or heterocyclyl group form a saturated or unsaturated hydrocarbyl ring. In other words, a saturated or unsaturated hydrocarbyl ring may be optionally fused with the cycloalkyl or heterocyclyl group.

When any of the foregoing substituents represents or contains an aryl or cycloalkyl moiety, the aryl or cycloalkyl moiety may itself be substituted by one or more halogen atoms, nitro, cyano, alkyl, haloalkyl, alkoxy or haloalkoxy groups. In the case of cycloalkyl and heterocyclyl groups, optional substituents also include groups which together with two adjacent carbon atoms of the cycloalkyl or heterocyclyl group form a saturated or unsaturated hydrocarbyl ring. In other words, a saturated or unsaturated hydrocarbyl ring may be optionally fused with the cycloalkyl or heterocyclyl group.

Optionally substituted moieties may be unsubstituted or have from one up to the maximal possible number of substituents. Typically, 0 to 3 substituents are present.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier. As used in accordance with this invention, the term providing an effective amount of a compound means either directly administering such compound, or administering a prodrug derivative, or analog which will form an effective amount of the compound within the body.

DESCRIPTION OF THE INVENTION

Compounds of this invention are prepared according to the procedures described in U.S. Pat. Nos. 5,593,996; 5,756,509; 5,948,783; 5,981,534; 5,612,345; 5,994,360; 6,020,338; 5,985,883; 5,854,252; 5,808,066; 5,817,663; 5,955,252; 5,965,561; 5,986,135; and 5,750,766 which are hereby incorporated herein by reference.

Representative compounds of this invention were evaluated in several standard pharmacological test procedures that showed that the compounds of this invention possess significant activity as promoters of microtubule polymerization and are antineoplastic agents. Based on the activity shown in the standard pharmacological test procedures, the compounds of this invention are therefore useful as anticancer agents. Associated cancers are selected from the group consisting of breast, colon, lung, prostate, melanoma, epidermal, leukemia, kidney, bladder, mouth, larynx, esophagus, stomach, ovary, pancreas, liver, skin and brain. In particular the compounds of this invention possess an effect similar to Paclitaxel. The test procedures used and results obtained are shown below.

Cytotoxicity Standard Pharmacological Test
Procedure Using MTS as Detection Reagent This standard pharmacological test procedure identifies representative examples of substituted triazolopyrimidine compounds of the invention, which further includes compounds of Formula (I), which kill various human cancer cell lines. The test is based on the conversion by viable cells, but not by dead cells, of the tetrazolium salt, MTS, into a water-soluble colored formazan which is detected by spectrophotometry. The test procedure was used to identify the most potent compounds within a series of related structures which were known or suspected to have a microtubule mechanism of action. The most potent compounds were then taken forward into other test procedures which specifically analyzed effects on microtubules.

Part 1. Cytotoxicity with HeLa Cells

In the first cytotoxicity test, representative compounds of the invention were tested with the HeLa human cervical carcinoma cell line at a single concentration. HeLa cells (ATCC CCL2.2) were routinely maintained by twice-weekly subculture in fresh medium. Medium was RPMI-1640 with L-glutamine, supplemented with 10% heat-inactivated fetal calf serum, 100 units/ml penicillin, and 100 µg/ml streptomycin.

For assay, HeLa cells were harvested by trypsinization, washed, counted and distributed to wells of 96-well flat-bottom microtiter plates at 1000 cells per well in 100 µl of medium. The plates were incubated at 37° in humidified 5% $CO_2$ in air for about 24 hr.

On day 2, compounds for test were diluted and added to wells. Compounds were dissolved in dimethyl sulfoxide (DMSO) at 10 mg/ml. These solutions were diluted into medium to give solutions of 20 µg/ml, and then 100 µl was added in duplicate to wells already containing cells, to give final drug concentrations of 10 µg/ml and a final DMSO concentration of 0.1%. Each plate also contained the following controls: cells with no drug (uninhibited cell growth=maximal MTS response=control response); cells plus 100 nM paclitaxel (all cells killed=minimal MTS response); and medium only (MTS reagent control). The plates were returned to the incubator for three days.

After three days of culture with test compounds (day 5 overall), the MTS assay was done on all wells of the plates. Twenty µl of the combined MTS/PMS reagent (Promega "CellTiter 96 Aqueous Non-Radioactive Cell Proliferation Assay," catalog no. G5421; see Technical Bulletin No. 169, Revised September 1996) were added to each well with a repeating pipettor, and the plates were returned to the 37° incubator for 2 hr before recording the absorbance of each well at 490 nm using an ELISA plate reader.

The absorbance values of the duplicate sample wells were averaged and expressed as a percentage of the average value of the control wells. Percentages less than 100 indicated that the test compounds had exerted a cytotoxic effect on the cells. The results of this pharmacological test procedure are displayed in Table 1.

TABLE 1

Evaluation of Representative Compounds of the Invention in the MTS Cytotoxicity Standard Pharmacological Test Procedure with HeLa Cells

| Ex No. | Percent of Control at 10 ug/ml |
|---|---|
| 1 | −1.6 |
| 2 | 10.4 |
| 4 | 2.9 |
| 5 | −0.8 |
| 6 | −0.4 |
| 7 | 0.6 |
| 8 | 2 |
| 9 | 8.1 |
| 12 | 0.3 |
| 19 | −1.3 |
| 24 | 3.7 |
| 27 | 2.2 |
| 28 | 3.4 |
| 30 | −0.4 |
| 32 | 20.3 |
| 33 | −1.3 |
| 35 | 17.6 |
| 37 | −1.6 |
| 38 | 0.2 |
| 39 | 10.6 |
| 41 | 7.1 |
| 42 | −0.1 |
| 43 | 5.8 |
| 47 | 0 |
| 48 | 13.9 |
| 49 | 12 |
| 54 | −0.1 |
| 59 | 0.9 |
| 60 | 4.9 |
| 61 | −1.2 |
| 62 | −0.7 |
| 63 | 10.6 |
| 64 | −2 |
| 65 | −0.6 |
| 66 | −0.7 |
| 70 | 1.4 |
| 72 | −1.8 |
| 73 | 15.6 |
| 79 | 7.1 |
| 82 | −1.5 |
| 87 | −0.2 |
| 99 | 1.8 |
| 102 | 1.1 |
| 103 | −0.7 |
| 105 | 0 |
| 113 | −0.3 |
| 116 | −1.3 |
| 117 | −0.1 |
| 121 | −0.8 |
| 122 | 2.1 |
| 123 | −2.2 |
| 124 | −1.6 |
| 127 | −0.9 |
| 128 | −0.3 |
| 130 | 5.4 |
| 132 | 3.4 |
| 133 | 10.7 |
| 135 | −1.1 |
| 140 | −0.9 |
| 141 | 10.8 |
| 143 | 92.8 |
| 144 | 2.3 |
| 145 | 16.2 |
| 146 | 16.1 |
| 149 | 7.8 |
| 150 | 3.4 |
| 151 | 9.6 |
| 157 | −2.7 |
| 158 | −0.4 |
| 159 | −1 |
| 160 | 1.1 |
| 163 | 27.2 |
| 167 | −2.5 |
| 168 | 8.7 |
| 169 | 23.8 |
| 170 | 22.6 |
| 172 | −0.9 |
| 173 | −0.6 |
| 174 | 0.6 |
| 175 | 1.9 |
| 176 | −0.6 |
| 177 | 8.5 |
| 180 | −0.3 |
| 181 | −1.5 |
| 182 | −1.7 |
| 183 | −0.1 |
| 184 | 1.3 |
| 185 | 1.5 |
| 186 | 1 |
| 187 | −1.4 |
| 188 | 8.8 |
| 189 | 2.2 |
| 213 | 10.2 |
| 216 | 5.8 |
| 217 | −0.5 |
| 225 | −1 |

Part 2. Cytotoxicity with COLO 205 Cells

In the second cytotoxicity standard pharmacological test procedure, representative compounds of the invention were tested with the COLO 205 human colon adenocarcinoma cell line at six concentrations, in order to determine $IC_{50}$ values. COLO 205 cells (ATCC CCL 222) were routinely maintained by thrice-weekly subculture in fresh medium. Medium was RPMI-1640 with L-glutamine, supplemented with 10% heat-inactivated fetal calf serum, 20 mM HEPES, 100 units/ml penicillin, and 100 µg/ml streptomycin.

For the test procedure, COLO 205 cells were harvested by trypsinization, washed, counted and distributed to wells of 96-well flat-bottom microtiter plates at 1000 cells per well in 100 µl of medium. In addition, one row of wells on an additional plate received cells as above ("time 0" plate). All plates were incubated at 37° in humidified 5% $CO_2$ in air for about 24 hr.

On day 2, compounds for test were diluted and added to wells. Compounds were dissolved in DMSO at 10 mg/ml. For each compound, six serial 3-fold dilutions were prepared in medium. The highest drug concentration with cells was 5 µg/ml and the highest DMSO concentration was 0.05%. Drugs were added in duplicate to wells in 100 μl volume. Each plate also contained the following controls: cells with no drug (uninhibited cell growth=maximal MTS response); cells plus 100 nM paclitaxel (all cells killed=minimal MTS response); and medium only (MTS reagent control). The plates were returned to the incubator for three days.

At the time of drug addition to the experimental plates, the MTS assay was run on the "time 0" plate. This produced the "time 0 MTS value" which was related to the number of viable cells per well at the time of drug addition. The MTS values of the wells of the experimental plates were lower than, higher than, or the same as the time 0 value, depending on whether a drug killed the cells, did not inhibit cell growth, or was cytostatic, respectively.

After three days of culture with test compounds (day 5 overall), the MTS assay was done on all wells of the experimental plates. The results for each plate were calculated separately, using its own controls. The absorbance values of the duplicate sample wells were averaged and divided by the average of the "time 0" values. The average of the control wells without drug, divided by the average "time 0" value, gave the maximal relative increase in MTS color yield due to cell growth during the final three days of culture. The average of the control wells with paclitaxel, divided by the "time 0" value, gave the minimal relative color yield for cells that were completely killed. The six values for each compound were plotted against concentration, and the concentration that produced a relative color yield half way between the maximum and minimum was taken as the $IC_{50}$ value. The most potent compounds had the lowest $IC_{50}$ values. Test results of representative compounds of the invention are displayed in Table 2.

In addition, some compounds of the invention were tested in duplicate at 25 and 50 μg/ml with COLO 205 cells in the MTS cytotoxicity pharmacological test procedure. Results were expressed as a percent of the average value of the control wells. Percentages less than 100 indicated that the test compounds had exerted a cytotoxic effect on the cells. These test results are also displayed in Table 2.

TABLE 2

Evaluation of Representative Compounds of the Invention in the MTS Cytotoxicity Standard Pharmacological Test Procedure with COLO 205 Cells

| Ex No. | IC50 (μg/ml) | n | % of Control At 25 μg/ml | 50 μg/ml |
|---|---|---|---|---|
| 1 | 0.84 | | | |
| 2 | 0.092 | | | |
| 3 | 0.82 | | | |
| 4 | 0.082 | | | |
| 5 | 0.057 | | | |
| 6 | 0.16 | | | |
| 7 | 0.12 | | | |
| 8 | 3.3 | | | |
| 9 | 0.86 | | | |
| 10 | 0.35 | | | |
| 11 | 2.5 | | | |
| 12 | 0.32 | 2 | | |
| 13 | 4.3 | | | |
| 14 | 0.22 | | | |
| 15 | 1.2 | | | |
| 16 | 4.8 | | | |
| 17 | 0.91 | | | |
| 18 | 0.33 | | | |
| 19 | 0.25 | | | |
| 20 | 1 | | | |
| 21 | 2.8 | | | |
| 22 | 4.6 | | | |
| 23 | 3.7 | | | |
| 24 | >5 | | | |
| 25 | >5 a | | | |
| 26 | 0.33 | | | |
| 27 | 0.033 | | | |
| 28 | 0.08 | | | |
| 29 | 0.29 | | | |
| 30 | 0.31 | 2 | | |
| 31 | 2.8 | | | |
| 32 | >5 | | | |
| 33 | 0.062 | | | |
| 34 | 0.44 | | | |
| 35 | 0.026 | 3 | | |
| 36 | 0.1 | | | |
| 37 | >5 | | | |
| 38 | 2.5 | | | |
| 39 | 2.2 | | | |
| 40 | 0.31 | | | |
| 41 | 0.062 | | | |
| 42 | 0.33 | | | |
| 43 | 0.084 | | | |
| 44 | 0.64 | | | |
| 45 | 4.8 | | | |
| 46 | 0.31 | | | |
| 47 | 0.11 | | | |
| 48 | 0.13 | | | |
| 49 | 0.15 | | | |
| 50 | 2.1 | | | |
| 51 | 0.86 | | | |
| 52 | 0.7 | | | |
| 53 | 1.3 | | | |
| 54 | 0.094 | | | |
| 55 | 0.59 | | | |
| 56 | 0.86 | | | |
| 57 | 0.64 | | | |
| 58 | 1 | | | |
| 59 | 0.18 | | | |
| 60 | 0.19 | | | |
| 61 | 0.095 | | | |
| 62 | 0.13 | | | |
| 63 | 0.16 | | | |
| 64 | 0.68 | 2 | | |
| 65 | 0.18 | | | |
| 66 | 0.11 | | | |
| 67 | 0.34 | | | |
| 68 | 1.7 | 2 | | |
| 69 | 0.36 | | | |
| 70 | 0.22 | | | |
| 71 | 0.87 | 2 | | |
| 72 | 0.22 | | | |
| 73 | 0.13 | | | |
| 74 | 0.31 | | | |
| 75 | 4.3 | | | |
| 76 | 0.37 | 2 | | |
| 77 | 0.66 | 2 | | |
| 78 | 2.4 | | | |
| 79 | 0.27 | | | |
| 80 | 2.6 | 2 | | |
| 81 | 2.5 | 2 | | |
| 82 | 0.038 | | | |
| 83 | 3 | 2 | | |
| 84 | 2.8 | | | |
| 85 | 2.8 | 2 | | |
| 86 | 0.26 | 2 | | |
| 87 | 0.24 | | | |
| 88 | 2.8 | 2 | | |
| 89 | 2.9 | 2 | | |
| 90 | 1 | | | |
| 91 | 0.39 | 2 | | |
| 92 | 1.8 | | | |

TABLE 2-continued

Evaluation of Representative Compounds of the Invention in the MTS Cytotoxicity Standard Pharmacological Test Procedure with COLO 205 Cells

| Ex No. | IC50 (μg/ml) | n | % of Control At 25 μg/ml | % of Control At 50 μg/ml |
|---|---|---|---|---|
| 93 | 2.7 | 2 | | |
| 94 | 3.5 | 2 | | |
| 95 | 3.8 | | | |
| 96 | 0.79 | 2 | | |
| 97 | >5 a | | | |
| 98 | 2 | 2 | | |
| 99 | 0.064 | | | |
| 100 | >5 a | | | |
| 101 | 4.4 | | | |
| 102 | 2.3 | | | |
| 103 | 0.27 | | | |
| 104 | 0.25 | 2 | | |
| 105 | 0.12 | 2 | | |
| 106 | >5 a | | | |
| 107 | 0.11 | 2 | | |
| 108 | 0.63 | 2 | | |
| 109 | 3.5 | | | |
| 110 | 0.32 | 2 | | |
| 111 | 0.39 | 2 | | |
| 112 | 0.34 | | | |
| 113 | 0.91 | | | |
| 114 | 3.7 | | | |
| 115 | >5 a | | | |
| 116 | >5 | | | |
| 117 | 0.26 | | | |
| 118 | 1.2 | 2 | | |
| 119 | 0.75 | 2 | | |
| 120 | 1.4 | 2 | | |
| 121 | 2.7 | | | |
| 122 | 0.73 | | | |
| 123 | >5 | | | |
| 124 | 0.12 | | | |
| 125 | 4.7 | 2 | | |
| 126 | 0.14 | | | |
| 127 | 0.056 | | | |
| 128 | 2.6 | | | |
| 129 | 0.31 | 2 | | |
| 130 | 0.91 | | | |
| 131 | 0.1 | 2 | | |
| 132 | 0.084 | | | |
| 133 | 0.092 | 2 | | |
| 134 | 0.33 | 2 | | |
| 135 | 0.16 | | | |
| 136 | 0.55 | 2 | | |
| 137 | 1.2 | | | |
| 138 | 0.34 | 2 | | |
| 139 | 0.96 | | | |
| 140 | 0.075 | | | |
| 141 | 0.28 | | | |
| 142 | 0.29 | 2 | | |
| 143 | 0.097 | | | |
| 144 | 0.084 | | | |
| 145 | 2.5 | | | |
| 146 | 0.099 | | | |
| 147 | 1.2 | 2 | | |
| 148 | 0.36 | | | |
| 149 | 0.056 | | | |
| 150 | 0.28 | | | |
| 151 | 0.099 | | | |
| 152 | 1 | | | |
| 153 | 0.42 | | | |
| 154 | 1.2 | | | |
| 155 | 1.1 | | | |
| 156 | 0.11 | | | |
| 157 | >5 | | | |
| 158 | 0.19 | | | |
| 159 | 0.38 | | | |
| 160 | 0.27 | | | |
| 161 | 2.6 | | | |
| 162 | 0.78 | | | |
| 163 | 0.27 | | | |
| 164 | 0.17 | | | |
| 165 | 0.96 | | | |
| 166 | 0.32 | | | |
| 167 | 0.1 | | | |
| 168 | 0.11 | | | |
| 169 | 0.31 | 4 | | |
| 170 | 0.074 | 11 | | |
| 171 | 0.29 | | | |
| 172 | 0.3 | | | |
| 173 | 0.3 | | | |
| 174 | 0.13 | | | |
| 175 | 0.038 | 3 | | |
| 176 | 0.1 | | | |
| 177 | 0.13 | | | |
| 178 | 0.099 | 3 | | |
| 179 | 0.35 | | | |
| 180 | 0.81 | | | |
| 181 | 0.043 | | | |
| 182 | 1.3 | | | |
| 183 | 0.078 | | | |
| 184 | 0.25 | | | |
| 185 | 0.04 | | | |
| 186 | 0.034 | | | |
| 187 | 0.035 | | | |
| 188 | 0.012 | 2 | | |
| 189 | 0.055 | | | |
| 190 | 0.33 | | | |
| 191 | 0.032 | | | |
| 192 | >5 a | | | |
| 193 | 0.95 | | | |
| 194 | 0.58 | | | |
| 195 | 0.1 | | | |
| 196 | 0.15 | | | |
| 197 | 0.3 | | | |
| 198 | 0.091 | 3 | | |
| 199 | 0.38 | | | |
| 200 | 0.27 | | | |
| 201 | 0.39 | | | |
| 202 | 0.25 | | | |
| 203 | 0.17 | | | |
| 204 | 0.12 | | | |
| 205 | 0.036 | | | |
| 206 | 0.12 | | | |
| 207 | 0.035 | | | |
| 208 | 0.014 | 2 | | |
| 209 | 0.11 | | | |
| 210 | 0.31 | | | |
| 211 | 0.049 | 3 | | |
| 212 | 0.88 | | | |
| 213 | 0.47 | | | |
| 214 | 0.79 | | | |
| 215 | 3.5 | | | |
| 216 | 0.63 | | | |
| 217 | 0.2 | | | |
| 218 | >5 a | | | |
| 219 | 0.89 | | | |
| 220 | 4.9 | | | |
| 221 | 2.8 | | | |
| 222 | 5 | 2 | | |
| 223 | 2.1 | | | |
| 224 | 0.3 | | | |
| 225 | 0.086 | | | |
| 226 | 0.095 | | | |
| 227 | 4.3 | | | |
| 228 | >5 a | | | |
| 229 | 0.95 | 2 | | |
| 230 | 2.5 | | | |
| 231 | | | 44.3 | 6.6 |
| 232 | | | 67.5 | 15.0 |
| 233 | | | 27.3 | 20.4 |
| 234 | | | 5.6 | −4.5 |

TABLE 2-continued

Evaluation of Representative Compounds of the Invention in the MTS Cytotoxicity Standard Pharmacological Test Procedure with COLO 205 Cells

| Ex No. | IC50 (µg/ml) | n | % of Control At 25 µg/ml | % of Control At 50 µg/ml |
|---|---|---|---|---|
| 235 | | | 80.6 | 14.7 |
| 236 | | | 28.4 | 10.9 |
| 237 | | | 24.1 | −3.5 |
| 238 | | | 100.4 | 41.5 |
| 239 | | | 58.8 | 25.5 |
| 240 | | | −0.9 | −4.0 |
| 241 | | | 2.3 | 2.4 |
| 242 | | | 13.1 | −4.8 |
| 243 | | | 12.7 | −3.0 |
| 244 | | | 9.2 | 21.0 |
| 245 | | | 100.3 | 72.5 |
| 246 | | | 4.0 | −4.8 |
| 247 | | | 63.6 | 46.4 |
| 248 | | | 15.5 | −3.9 |
| 249 | | | 47.4 | 20.3 |
| 250 | | | 16.4 | 4.6 |
| 251 | | | 103.9 | 28.1 |
| 252 | | | 94.8 | 69.6 |
| 253 | | | 120.0 | 74.1 |
| 254 | | | 39.6 | 15.6 |
| 255 | | | 58.3 | 86.1 |
| 256 | | | 20.2 | 14.8 |
| 257 | | | 27.3 | −3.5 |
| 258 | | | 74.6 | 44.1 |
| 259 | | | 32.6 | 0.7 |
| 260 | | | 87.8 | 53.5 |
| 261 | | | 7.4 | −3.9 |
| 262 | | | 23.7 | −5.1 |
| 263 | | | −1.5 | 2.0 |
| 264 | | | 34.5 | −4.2 |
| 265 | | | 8.1 | −1.6 |
| 266 | | | 84.9 | 72.4 |
| 267 | | | 17.8 | 32.1 |
| 268 | | | −0.8 | 4.2 |
| 269 | | | 3.5 | 11.9 |
| 270 | 0.095 | | | |
| 271 | 0.32 | | | |
| 272 | 0.91 | | | |
| 273 | 1 | | | |
| 274 | 1.9 | | | |
| 275 | 0.13 | | | |

Notes to Table 2:
1. n = number of independent assays (n = 1 unless stated otherwise)
2. a means that at 5 µg/ml the inhibition was between 30 and 50%

TABLE 3

Evaluation of Representative Compounds of the Invention and Standard Cytotoxic Agents in the MTS Cytotoxicity Standard Pharmacological Test Procedure with Four Human Cancer Cell Lines

| Example | IC$_{50}$ (nM) H157 | U87MG | PC-3 MM2 | DLD1 |
|---|---|---|---|---|
| 35 | 31 | 390 | 220 | 105 |
| 169 | | >1000 | >1000 | |
| 170 | 310 | 200 | 140 | 560 |
| 175 | | 180 | 240 | 215 |
| 178 | | 480 | 550 | |
| 186 | 38 | | | |
| 187 | 86 | | | |
| 188 | 16 | 48 | 73 | 48 |
| 198 | | 640 | 580 | |
| 205 | 83 | | | |
| 208 | 10 | 120 | 140 | 69 |
| 211 | | 370 | 400 | |

TABLE 3-continued

Evaluation of Representative Compounds of the Invention and Standard Cytotoxic Agents in the MTS Cytotoxicity Standard Pharmacological Test Procedure with Four Human Cancer Cell Lines

| Example | IC$_{50}$ (nM) H157 | U87MG | PC-3 MM2 | DLD1 |
|---|---|---|---|---|
| Camptothecin | 10 | | | |
| Colchicine | 13 | 6.5 | 10 | 25 |
| Doxorubicin | 17 | | | 170 |
| Mitoxantrone | 13 | | | |
| Nocodazole | 33 | 34 | 43 | 40 |
| Paclitaxel | | | 0.17 | 1.4 |
| Vincristine | 0.28 | | 0.30 | 3.0 |

Part 4. Cytotoxicity with KB Cells and Drug-Resistant Lines Derived from KB

The cytotoxicity standard pharmacological test procedure with MTS detection was applied to representative compounds of the invention with the KB human epidermoid carcinoma cell line and two multidrug resistant lines derived from it. These derived lines were colchicine-resistant KB 8.5, which expresses a moderate level of the multidrug transporter P-glycoprotein, and vinblastine-resistant KB VI, which expresses a high level of P-glycoprotein. The purpose of these experiments was to determine if the compounds were able to overcome drug resistance mediated by P-glycoprotein. If the IC$_{50}$'s of the compounds are essentially the same on all three lines, then the compounds are not substrates of P-glycoprotein. If on the other hand, the compounds have much higher IC$_{50}$'s on KB 8.5 and KB VI compared to KB (as do paclitaxel, vincristine, and many other standard anti-cancer drugs) then they would be substrates of P-glycoprotein.

The procedure of the cytotoxicity test and the method of data calculation were the same as described above in Part 2 with COLO 205 cells. The results are displayed in Table 4. The results show that the compounds of this invention have essentially the same IC$_{50}$'s on all three cell lines, indicating that they would not be subject to multidrug resistance mediated by P-glycoprotein.

TABLE 4

Evaluation of Representative Compounds of the Invention and Standard Cytotoxic Agents in the MTS Cytotoxicity Standard Pharmacological Test Procedure with Human Cancer Cell Lines that Overexpress the P-glycoprotein Transporter

| Example | IC$_{50}$ (nM) KB | KB 8.5 | KB VI | Relative Resistance KB | KB 8.5 | KB VI |
|---|---|---|---|---|---|---|
| 35 | 19 | 31 | 16 | 1 | 1.6 | 0.8 |
| 186 | 30 | 48 | 33 | 1 | 1.6 | 1.1 |
| 187 | 45 | 76 | 56 | 1 | 1.7 | 1.2 |
| 188 | 10 | 18 | 11 | 1 | 1.8 | 1.1 |
| Taxol | <0.03 | 19 | 3,325 | 1 | >630 | >111,000 |
| Vincristine | <0.06 | 29 | 3,150 | 1 | >480 | >52,500 |
| Colchicine | 7.2 | 51 | 1,330 | 1 | 7.1 | 185 |
| Nocodazole | 21 | 24 | 33 | 1 | 1.1 | 1.6 |
| Doxorubicin | 34 | 101 | 4,400 | 1 | 3.0 | 130 |

Part 5. Cytotoxicity with S1 Cells and a Drug-Resistant Line Derived from S1

The cytotoxicity standard pharmacological test procedure with MTS detection was applied to representative compounds of the invention with the S1 human colon carcinoma cell line and a multidrug resistant line derived from it. The derived line was mitoxantrone-resistant S1-M1, which expresses the multidrug transporter MXR. The purpose of these experiments was to determine representative compounds of the invention able to overcome drug resistance mediated by MXR. If the $IC_{50}$'s of the compounds are essentially the same on both lines, then the compounds are not substrates of MXR. If on the other hand, the compounds have much higher $IC_{50}$'s on S1-M1 compared to S1 (as do many standard anti-cancer drugs) then they would be substrates of MXR.

The procedure of the cytotoxicity test and the method of data calculation were the same as described above in Part 2 with COLO 205 cells. The results are displayed in Table 5. The results show that the compounds of this invention have essentially the same $IC_{50}$'s on both cell lines, indicating that they would not be subject to multidrug resistance mediated by MXR.

TABLE 5

Evaluation of Representative Compounds of the Invention and Standard Cytotoxic Agents in the MTS Cytotoxicity Pharmacological Test Procedure with a Human Cancer Cell Line that Overexpresses the MXR Transporter Protein

| Example | $IC_{50}$ (nM) | | Relative Resistance | |
|---|---|---|---|---|
| | S1 | S1-M1 | S1 | S1-M1 |
| 35 | 73 | 94 | 1 | 1.3 |
| 186 | 99 | 102 | 1 | 1.0 |
| 187 | 99 | 124 | 1 | 1.3 |
| 188 | 33 | 74 | 1 | 2.2 |
| Colchicine | 11 | 47 | 1 | 4.3 |
| Nocodazole | 43 | 146 | 1 | 3.4 |
| Doxorubicin | 19 | 10,700 | 1 | 565 |
| Mitoxantrone | <4 | >10,000 | 1 | >2,500 |
| Camptothecin | 6.8 | 21 | 1 | 3.1 |

Inhibition of Cellular Prolieration Standard Pharmacological Test Procedure Using Sulforhodamine B as Detection Reagent This standard pharmacological test procedure measures the ability of compounds to inhibit cellular proliferation. Sulforhodamine B staining was used to estimate total cellular protein in each culture after exposure to compounds. A decrease in staining compared to untreated control cultures indicated an inhibition of proliferation.

Two cell lines were used in these experiments: Reh human acute lymphocytic leukemia, and CCRF-CEM human acute lymphoblastic leukemia, both obtained from ATCC. Two types of experiments were done on each of the two cell lines. In the first, cells were cultured with Example 170 at several concentrations for either 24 or 72 hr, and the effect on cellular proliferation was determined. In the second, cells were cultured with Example 170 at several concentrations for 24 hr, the compound was removed and replaced with fresh medium without compound, culture was continued for another 48 hr, and the effect on cellular proliferation was determined. This second experiment determined the ability of cells to recover from the damage inflicted by compound during the first 24 hr of culture. At the end of the incubation periods, cells were fixed with trichloroacetic acid and stained with sulforhodamine B using the in vitro Toxicology Assay Kit (Sigma). Actinomycin D was used as a positive control in all experiments. Bound dye was measured spectrophotometrically at 565 nm with a reference wavelength of 690 nm. Cultures were done in 96-well assay plates with five replicates of each concentration. The absorbance values of the replicates were averaged and expressed as a percent of the vehicle control. Each experiment was repeated once, and the percent of control for a given concentration in each experiment were averaged to calculate the results displayed in Table 6.

The results showed that Example 170 inhibited the proliferation of both cell lines, with a greater effect observed after 72 hr compared with 24 hr. In addition, the recovery experiment showed that neither cell line could recover from the toxicity induced by 24 hr of culture with Example 170.

An additional experiment was done with HL-60 human promyelocytic leukemia in which the inhibition of cellular proliferation by several concentrations of Example 170 were determined after 24 or 72 hrs of culture using the Sulforhodamine B test procedure as described above. Concentrations of Example 170 ranged from 0.005-100 µg/ml. The calculated $EC_{50}$ value at 24 hr was 2.3 µg/ml, and the $EC_{50}$ value at 72 hr was 0.1 µg/ml.

TABLE 6

Evaluation of Example 170 in the Sulforhodamine B Standard Pharmacological Test Procedure with Two Human Leukemia Cell Lines

| | Percent of Control | | | | | |
|---|---|---|---|---|---|---|
| | Reh Cells | | | CCRF-CEM Cells | | |
| Conc. (µg/ml) | 24 hr. Treatment | 72 hr Treatment | 24 hr Treatment 48 hr Recovery | 24 hr Treatment | 72 hr Treatment | 24 hr Treatment 48 hr Recovery |
| 0.005 | 120.15 | 88.57 | 105.29 | 104.86 | 94.88 | 152.66 |
| 0.01 | 110.83 | 89.43 | 103.98 | 111.05 | 88.98 | 143.58 |
| 0.05 | 81.50 | 71.31 | 81.23 | 67.31 | 19.73 | 57.05 |
| 0.1 | 68.67 | 65.87 | 84.68 | 65.48 | 24.04 | 38.99 |
| 0.5 | 67.70 | 66.24 | 74.13 | 65.72 | 11.59 | 50.17 |
| 1 | 83.94 | 52.91 | 66.81 | 51.41 | 20.74 | 29.42 |
| 5 | 66.21 | 41.86 | 61.34 | 30.04 | 22.24 | 28.90 |
| 10 | 71.46 | 44.70 | 34.10 | 42.05 | 8.17 | 18.19 |
| 50 | 55.07 | 35.40 | 36.36 | 47.10 | 24.84 | 27.16 |
| 100 | 84.35 | 51.62 | 35.76 | 113.70 | 54.07 | 39.47 |
| 0.2* | 66.99 | 50.54 | 39.75 | 52.44 | 45.71 | 20.26 |

*Actinomycin-D

Cell Cycle Analysis Standard Phamacological Test Procedure

This standard pharmacological test procedure measures the percentages of cells in a population that are in the G1, S and G2/M phases of the cell cycle. It utilizes staining of fixed cells with propidium iodide and analysis of these cells by flow cytometry. The procedure also gives an estimate of apoptosis induction caused by drug treatment by measurement of the appearance of particles with sub-G1 amounts of DNA. Microtubule-active drugs characteristically arrest cells in the G2/M phase of the cell cycle because of disruption of the function of the microtubules that comprise the mitotic spindle.

HeLa cells were maintained in RPMI-1640 medium with L-glutamine, supplemented with 10% heat-inactivated fetal calf serum, 100 units/ml penicillin, and 100 µg/ml streptomycin. For assay, cells were harvested by trypsinization, washed, counted and distributed to wells of a 6-well plate at 50,000 cells per well in 3 ml of medium. Cells were cultured overnight at 37° in humidified 5% $CO_2$ in air.

On day 2, compounds for test were diluted and added to wells at the final concentrations given in the tables. Twenty hours after drug addition, cells from each well were harvested, fixed with cold 80% ethanol, treated with 100 μg/ml RNAse and stained with propidium iodide before analysis by flow cytometry. The percentages of total cells in G1, S, G2/M, and apoptosis (sub-G1 population) were estimated from the fluorescence histograms, and compared with those determined using untreated control cells in the same assay.

Table 7 displays results for representative compounds of this invention tested at a low concentration and at a five-fold higher concentration. Table 8 displays results of a second experiment in which representative compounds were tested at six concentration levels each. In both experiments the compounds caused a profound increase in the percentage of cells in the G2/M phase of the cell cycle and induced substantial apoptosis.

TABLE 7

Evaluation of Representative Compounds of the Invention in the Cell Cycle Analysis Standard Pharmacological Test Procedure with HeLa Cells

| Example | Conc. (μg/mL) | Apop | G1 | S | G2/M |
|---|---|---|---|---|---|
| None | — | 3 | 64 | 18 | 16 |
|  | — | 2 | 63 | 18 | 17 |
| 1 | 0.84 | 8 | 3 | 10 | 79 |
|  | 4.2 | 13 | 7 | 12 | 68 |
| 5 | 0.057 | 44 | 10 | 22 | 25 |
|  | 0.285 | 9 | 1 | 5 | 85 |
| 7 | 0.12 | 8 | 2 | 6 | 84 |
|  | 0.6 | 9 | 3 | 8 | 81 |
| 9 | 0.86 | 10 | 2 | 7 | 81 |
|  | 4.3 | 16 | 28 | 21 | 35 |
| 12 | 0.27 | 46 | 10 | 18 | 26 |
|  | 1.35 | 7 | 1 | 7 | 85 |
| 27 | 0.033 | 28 | 4 | 13 | 55 |
|  | 0.165 | 8 | 1 | 5 | 86 |
| 35 | 0.022 | 28 | 5 | 14 | 54 |
|  | 0.11 | — | — | — | — |
| 39 | 2.19 | 26 | 4 | 15 | 55 |
|  | 10.95 | 19 | 17 | 20 | 45 |
| 41 | 0.062 | 9 | 58 | 20 | 13 |
|  | 0.31 | 34 | 18 | 17 | 30 |
| 42 | 0.33 | 47 | 14 | 20 | 19 |
|  | 1.65 | 6 | 1 | 10 | 83 |
| 47 | 0.11 | 8 | 2 | 8 | 83 |
|  | 0.55 | 7 | 1 | 10 | 81 |
| 59 | 0.18 | 43 | 8 | 24 | 26 |
|  | 0.9 | 8 | 2 | 6 | 84 |
| 61 | 0.08 | 7 | 1 | 9 | 83 |
|  | 0.4 | 7 | 2 | 8 | 83 |
| 105 | 0.08 | 12 | 3 | 11 | 74 |
|  | 0.4 | 6 | 2 | 8 | 84 |
| 127 | 0.08 | 8 | 2 | 12 | 79 |
|  | 0.4 | 6 | 3 | 6 | 84 |
| 151 | 0.08 | 15 | 4 | 14 | 67 |
|  | 0.4 | 9 | 6 | 8 | 76 |
| 186 | 0.08 | 7 | 2 | 8 | 82 |
|  | 0.4 | 7 | 2 | 10 | 80 |
| 187 | 0.08 | 6 | 4 | 9 | 81 |
|  | 0.4 | 7 | 2 | 9 | 81 |
| 188 | 0.08 | 9 | 2 | 8 | 81 |
|  | 0.4 | 9 | 2 | 10 | 78 |

Note to Table 6: Apop = Apoptosis

TABLE 8

Evaluation of Representative Compounds of the Invention in the Cell Cycle Analysis Standard Pharmacological Test Procedure with HeLa Cells

| Example | Conc. (μg/mL) | Apop | G1 | S | G2/M |
|---|---|---|---|---|---|
| None | — | 4 | 55 | 23 | 18 |
|  | — | 3 | 49 | 25 | 20 |
|  | — | 1 | 56 | 20 | 20 |
| 35 | 0.001 | 1 | 57 | 22 | 20 |
|  | 0.003 | 1 | 58 | 22 | 18 |
|  | 0.01 | 2 | 57 | 20 | 21 |
|  | 0.03 | 29 | 20 | 25 | 25 |
|  | 0.1 | 26 | 9 | 13 | 50 |
|  | 0.3 | 4 | 4 | 3 | 89 |
| 133 | 0.01 | 4 | 54 | 19 | 23 |
|  | 0.03 | 28 | 25 | 21 | 25 |
|  | 0.1 | 34 | 9 | 26 | 29 |
|  | 0.3 | 15 | 5 | 8 | 73 |
|  | 1 | 3 | 4 | 3 | 90 |
|  | 3 | 3 | 4 | 3 | 89 |
| 169 | 0.01 | 2 | 51 | 23 | 24 |
|  | 0.03 | 14 | 41 | 21 | 24 |
|  | 0.1 | 33 | 17 | 23 | 25 |
|  | 0.3 | 34 | 8 | 24 | 32 |
|  | 1 | 3 | 5 | 3 | 88 |
|  | 3 | 4 | 5 | 2 | 88 |
| 170 | 0.01 | 13 | 42 | 21 | 24 |
|  | 0.03 | 33 | 17 | 20 | 28 |
|  | 0.1 | 27 | 3 | 18 | 50 |
|  | 0.3 | 5 | 5 | 4 | 85 |
|  | 1 | 3 | 4 | 4 | 88 |
|  | 3 | 3 | 4 | 4 | 88 |
| 188 | 0.001 | 1 | 55 | 21 | 23 |
|  | 0.003 | 2 | 56 | 18 | 23 |
|  | 0.01 | 18 | 35 | 19 | 27 |
|  | 0.03 | 27 | 7 | 14 | 52 |
|  | 0.1 | 4 | 4 | 3 | 88 |
|  | 0.3 | 3 | 3 | 3 | 90 |
| 208 | 0.001 | 2 | 59 | 20 | 20 |
|  | 0.003 | 2 | 57 | 20 | 21 |
|  | 0.01 | 14 | 43 | 20 | 23 |
|  | 0.03 | 33 | 8 | 21 | 36 |
|  | 0.1 | 3 | 2 | 3 | 90 |
|  | 0.3 | 3 | 3 | 2 | 91 |

Note to Table 7: Apop = Apoptosis

Tubulin Polymerization Standard Pharmacological Test Procedure Using Highly Purified Tubulin This standard pharmacological test procedure determines the activity of representative compounds of this invention in promoting the polymerization of α/β tubulin heterodimers. The tubulin preparation used was over 99% pure so that any effects of test compounds on polymerization must be due to direct binding of the test compounds to tubulin protein. It is well known that in this assay paclitaxel promotes polymerization compared to the control reaction without drug, and that vincristine and colchicine inhibit polymerization. Highly purified tubulin does not exhibit substantial spontaneous polymerization at protein concentrations between 1 and 2 mg/ml. Therefore an agent such as glycerol is added to the reactions to lower the critical concentration for polymerization and yield a higher spontaneous control polymerization. In some experiments described below, either glycerol or guanosine 5'-triphosphate (the energy source of polymerization) was left out of the reaction mixtures in order to better compare the effects of paclitaxel and representative compounds of this invention.

Part 1. Polymerization of Purified Tubulin in the Presence of Guanosine 5'-triphosphate and Glycerol Bovine brain tubulin, purchased from Cytoskeleton, Inc., was greater than 99% pure by polyacrylamide gel electrophoresis. The protein was dissolved at 1.5 mg/ml in ice-cold GPEM buffer (80 mM piperazine-N,N'-bis[2-ethanesulfonic acid], pH 6.9, 1 mM ethylene glycol-bis(β-aminoethyl ether)-N,N,N',N'-tetraacetic acid, 1 mM magnesium chloride, 1 mM guanosine 5'-triphosphate, GTP) containing 10% (w/w) glycerol. The solution was centrifuged at top speed in an Eppendorf model 5415C microfuge for 10 min at 4° immediately before use. The tubulin solution was added to wells of a ½ area 96-well plate (Costar No. 3696) already containing the compounds of interest. Each compound was assayed at three concentrations as indicated. Final volume per well was 110 μl. Each sample was done in duplicate, and the control reaction, which received drug solvent only, was done in quadruplicate. The highest concentration of DMSO in any reaction was 1%. The plate was put in a Molecular Devices SpectraMax plate reader thermostated at 35° and the absorbance of each well at 340 nm was determined every minute for 60 minutes. The absorbance at time 0 for each well was subtracted from each of the subsequent absorbance readings for that well, and then the duplicates were averaged.

The results of this standard pharmacological test procedure with representative compounds of this invention and with standard microtubule-active drugs are displayed in Tables 9 to 14. Compounds that enhanced the rate and/or extent of purified tubulin polymerization compared to the control (as does paclitaxel) were judged to be promoters of polymerization; compounds that reduced the rate or extent of polymerization (e.g., vincristine, colchicine) were judged to be inhibitors.

TABLE 9

Evaluation of Examples 35 and 188 in the Tubulin Polymerization Standard Pharmacological Test Procedure $\Delta A_{340}$

| Time | Example 35 | | | Example 188 | | | |
|---|---|---|---|---|---|---|---|
| (min) | 10 μM | 1 μM | 0.1 μM | 10 μM | 1 μM | 0.1 μM | Control |
| 0 | 0 | 0 | 0 | 0 | 0 | 0 | 0 |
| 5 | 0.0434 | 0.0003 | 0.0004 | 0.0179 | −0.0007 | −0.0006 | −0.0009 |
| 10 | 0.0972 | 0.0015 | 0.0010 | 0.0469 | 0.0001 | −0.0005 | −0.0008 |
| 15 | 0.1219 | 0.0028 | 0.0012 | 0.0667 | 0.0016 | −0.0001 | 0.0001 |
| 20 | 0.1316 | 0.0058 | 0.0024 | 0.0813 | 0.0040 | 0.0009 | 0.0019 |
| 25 | 0.1364 | 0.0079 | 0.0041 | 0.0919 | 0.0063 | 0.0026 | 0.0051 |
| 30 | 0.1387 | 0.0106 | 0.0061 | 0.0988 | 0.0110 | 0.0052 | 0.0087 |
| 35 | 0.1397 | 0.0139 | 0.0079 | 0.1032 | 0.0141 | 0.0079 | 0.0132 |
| 40 | 0.1401 | 0.0177 | 0.0099 | 0.1064 | 0.0179 | 0.0119 | 0.0198 |
| 45 | 0.1392 | 0.0232 | 0.0133 | 0.1100 | 0.0229 | 0.0142 | 0.0221 |
| 50 | 0.1396 | 0.0278 | 0.0167 | 0.1149 | 0.0288 | 0.0203 | 0.0245 |
| 55 | 0.1399 | 0.0311 | 0.0193 | 0.1165 | 0.0337 | 0.0262 | 0.0282 |
| 60 | 0.1398 | 0.0350 | 0.0224 | 0.1176 | 0.0372 | 0.0304 | 0.0340 |

TABLE 10

Evaluation of Example 170 and Paclitaxel in the Tubulin Polymerization Standard Pharmacological Test Procedure $\Delta A_{340}$

| Time | Example 170 | | | Paclitaxel | | | |
|---|---|---|---|---|---|---|---|
| (min) | 10 μM | 1 μM | 0.1 μM | 10 μM | 1 μM | 0.1 μM | Control |
| 0 | 0 | 0 | 0 | 0 | 0 | 0 | 0 |
| 5 | 0.0103 | −0.0001 | −0.0005 | 0.0136 | 0.0044 | −0.0012 | −0.0009 |
| 10 | 0.0555 | 0.0008 | −0.0010 | 0.0416 | 0.0167 | −0.0010 | −0.0008 |
| 15 | 0.0923 | 0.0028 | −0.0005 | 0.0704 | 0.0336 | 0.0001 | 0.0001 |
| 20 | 0.1100 | 0.0056 | 0.0002 | 0.0931 | 0.0500 | 0.0025 | 0.0019 |
| 25 | 0.1199 | 0.0093 | 0.0018 | 0.1075 | 0.0638 | 0.0060 | 0.0051 |
| 30 | 0.1257 | 0.0143 | 0.0041 | 0.1162 | 0.0748 | 0.0100 | 0.0087 |
| 35 | 0.1289 | 0.0198 | 0.0053 | 0.1216 | 0.0835 | 0.0123 | 0.0132 |
| 40 | 0.1330 | 0.0246 | 0.0088 | 0.1245 | 0.0903 | 0.0168 | 0.0198 |
| 45 | 0.1353 | 0.0291 | 0.0124 | 0.1269 | 0.0957 | 0.0229 | 0.0221 |
| 50 | 0.1353 | 0.0338 | 0.0155 | 0.1279 | 0.0997 | 0.0257 | 0.0245 |
| 55 | 0.1363 | 0.0380 | 0.0192 | 0.1279 | 0.1027 | 0.0293 | 0.0282 |
| 60 | 0.1364 | 0.0419 | 0.0241 | 0.1282 | 0.1053 | 0.0314 | 0.0340 |

TABLE 11

Evaluation of Examples 169 and 175 in the Tubulin Polymerization Standard Pharmacological Test Procedure $\Delta A_{340}$

| Time | Example 169 | | | Example 175 | | | |
|---|---|---|---|---|---|---|---|
| (min) | 10 μM | 1 μM | 0.1 μM | 10 μM | 1 μM | 0.1 μM | Control |
| 0 | 0 | 0 | 0 | 0 | 0 | 0 | 0 |
| 5 | 0.0239 | 0.0005 | −0.0014 | 0.0073 | 0.0001 | −0.0012 | −0.0012 |
| 10 | 0.1172 | 0.0011 | −0.0009 | 0.0199 | 0.0014 | −0.0005 | −0.0011 |
| 15 | 0.1435 | 0.0024 | 0.0001 | 0.0309 | 0.0037 | 0.0011 | 0.0000 |
| 20 | 0.1509 | 0.0045 | 0.0020 | 0.0399 | 0.0067 | 0.0025 | 0.0024 |
| 25 | 0.1532 | 0.0073 | 0.0042 | 0.0488 | 0.0102 | 0.0057 | 0.0051 |
| 30 | 0.1548 | 0.0106 | 0.0057 | 0.0566 | 0.0160 | 0.0088 | 0.0108 |
| 35 | 0.1554 | 0.0154 | 0.0105 | 0.0638 | 0.0217 | 0.0116 | 0.0157 |
| 40 | 0.1555 | 0.0197 | 0.0136 | 0.0704 | 0.0294 | 0.0177 | 0.0203 |
| 45 | 0.1552 | 0.0246 | 0.0186 | 0.0761 | 0.0349 | 0.0233 | 0.0246 |
| 50 | 0.1545 | 0.0331 | 0.0234 | 0.0817 | 0.0416 | 0.0261 | 0.0329 |
| 55 | 0.1561 | 0.0414 | 0.0282 | 0.0872 | 0.0450 | 0.0309 | 0.0369 |
| 60 | 0.1552 | 0.0456 | 0.0322 | 0.0919 | 0.0485 | 0.0373 | 0.0392 |

TABLE 12

Evaluation of Example 178 and Paclitaxel in the Tubulin Polymerization Standard Pharmacological Test Procedure $\Delta A_{340}$

| Time | Example 178 | | | Paclitaxel | | | |
|---|---|---|---|---|---|---|---|
| (min) | 10 μM | 1 μM | 0.1 μM | 10 μM | 1 μM | 0.1 μM | Control |
| 0 | 0 | 0 | 0 | 0 | 0 | 0 | 0 |
| 5 | 0.0182 | −0.0029 | −0.0001 | 0.0200 | 0.0024 | −0.0008 | −0.0012 |
| 10 | 0.0304 | −0.0021 | 0.0000 | 0.0587 | 0.0144 | 0.0005 | −0.0011 |
| 15 | 0.0448 | −0.0007 | 0.0002 | 0.0939 | 0.0315 | 0.0031 | 0.0000 |
| 20 | 0.0602 | 0.0006 | 0.0009 | 0.1199 | 0.0484 | 0.0070 | 0.0024 |
| 25 | 0.0770 | 0.0039 | 0.0030 | 0.1369 | 0.0626 | 0.0103 | 0.0051 |
| 30 | 0.0951 | 0.0064 | 0.0055 | 0.1470 | 0.0746 | 0.0159 | 0.0108 |
| 35 | 0.1099 | 0.0110 | 0.0080 | 0.1522 | 0.0838 | 0.0197 | 0.0157 |
| 40 | 0.1250 | 0.0152 | 0.0134 | 0.1557 | 0.0913 | 0.0256 | 0.0203 |
| 45 | 0.1360 | 0.0202 | 0.0216 | 0.1583 | 0.0969 | 0.0304 | 0.0246 |
| 50 | 0.1424 | 0.0242 | 0.0218 | 0.1584 | 0.1014 | 0.0336 | 0.0329 |
| 55 | 0.1488 | 0.0273 | 0.0229 | 0.1588 | 0.1050 | 0.0368 | 0.0369 |
| 60 | 0.1538 | 0.0316 | 0.0299 | 0.1586 | 0.1076 | 0.0399 | 0.0392 |

TABLE 13

Evaluation of Examples 198 and 211 and Paclitaxel in the Tubulin Polymerization Standard Pharmacological Test Procedure

| | Example 198 | | | Example 211 | | | Paclitaxel | | | |
|---|---|---|---|---|---|---|---|---|---|---|
| * | 10 µM | 1 µM | 0.1 µM | 10 µM | 1 µM | 0.1 µM | 10 µM | 1 µM | 0.1 µM | ** |
| 0 | 0 | 0 | 0 | 0 | 0 | 0 | 0 | 0 | 0 | 0 |
| 5 | 0.0011 | 0.0001 | 0.0021 | −0.0008 | −0.0019 | −0.0001 | 0.0145 | 0.0037 | −0.0014 | −0.0012 |
| 10 | 0.0025 | 0.0006 | 0.0053 | −0.0006 | −0.0017 | 0.0014 | 0.0496 | 0.0173 | 0.0032 | −0.0014 |
| 15 | 0.0057 | 0.0017 | 0.0096 | 0.0009 | 0.0000 | 0.0043 | 0.0857 | 0.0381 | 0.0056 | −0.0001 |
| 20 | 0.0117 | 0.0046 | 0.0143 | 0.0029 | 0.0027 | 0.0080 | 0.1119 | 0.0572 | 0.0098 | 0.0031 |
| 25 | 0.0206 | 0.0071 | 0.0200 | 0.0055 | 0.0060 | 0.0129 | 0.1280 | 0.0731 | 0.0160 | 0.0077 |
| 30 | 0.0303 | 0.0106 | 0.0239 | 0.0085 | 0.0107 | 0.0173 | 0.1370 | 0.0860 | 0.0217 | 0.0124 |
| 35 | 0.0407 | 0.0153 | 0.0292 | 0.0121 | 0.0138 | 0.0228 | 0.1427 | 0.0961 | 0.0289 | 0.0193 |
| 40 | 0.0489 | 0.0214 | 0.0367 | 0.0165 | 0.0195 | 0.0287 | 0.1462 | 0.1041 | 0.0360 | 0.0223 |
| 45 | 0.0572 | 0.0258 | 0.0393 | 0.0211 | 0.0251 | 0.0321 | 0.1483 | 0.1102 | 0.0431 | 0.0288 |
| 50 | 0.0661 | 0.0320 | 0.0495 | 0.0263 | 0.0279 | 0.0397 | 0.1495 | 0.1148 | 0.0488 | 0.0345 |
| 55 | 0.0729 | 0.0360 | 0.0556 | 0.0320 | 0.0339 | 0.0458 | 0.1505 | 0.1185 | 0.0544 | 0.0389 |
| 60 | 0.0763 | 0.0413 | 0.0607 | 0.0383 | 0.0393 | 0.0512 | 0.1508 | 0.1211 | 0.0596 | 0.0440 |

Column heading: $\Delta A_{340}$

* Time (min)
** Control

TABLE 14

Evaluation of Vincristine, Colchicine, and Paclitaxel in the Tubulin Polymerization Standard Pharmacological Test Procedure

| | Vincristine | | | Colchicine | | | Paclitaxel | | | |
|---|---|---|---|---|---|---|---|---|---|---|
| * | 10 µM | 1 µM | 0.1 µM | 10 µM | 1 µM | 0.1 µM | 10 µM | 1 µM | 0.1 µM | ** |
| 0 | 0 | 0 | 0 | 0 | 0 | 0 | 0 | 0 | 0 | 0 |
| 5 | −0.0011 | −0.0008 | 0.0016 | 0.0005 | −0.0003 | −0.0011 | 0.0104 | 0.0023 | −0.0008 | −0.0016 |
| 10 | 0.0001 | −0.0007 | 0.0012 | 0.0011 | 0.0000 | −0.0012 | 0.0372 | 0.0128 | 0.0020 | −0.0013 |
| 15 | −0.0001 | −0.0007 | 0.0018 | 0.0006 | 0.0002 | −0.0008 | 0.0658 | 0.0288 | 0.0084 | 0.0007 |
| 20 | −0.0006 | −0.0001 | 0.0031 | −0.0001 | 0.0009 | 0.0003 | 0.0885 | 0.0434 | 0.0107 | 0.0027 |
| 25 | −0.0012 | 0.0003 | 0.0044 | −0.0003 | 0.0019 | 0.0024 | 0.1040 | 0.0568 | 0.0160 | 0.0054 |
| 30 | −0.0015 | 0.0012 | 0.0074 | −0.0008 | 0.0029 | 0.0058 | 0.1149 | 0.0682 | 0.0251 | 0.0103 |
| 35 | −0.0018 | 0.0019 | 0.0119 | −0.0008 | 0.0039 | 0.0086 | 0.1218 | 0.0779 | 0.0321 | 0.0181 |
| 40 | −0.0017 | 0.0029 | 0.0154 | −0.0012 | 0.0044 | 0.0119 | 0.1261 | 0.0857 | 0.0366 | 0.0232 |
| 45 | −0.0020 | 0.0041 | 0.0189 | −0.0016 | 0.0057 | 0.0159 | 0.1299 | 0.0920 | 0.0423 | 0.0272 |
| 50 | −0.0025 | 0.0057 | 0.0253 | −0.0020 | 0.0067 | 0.0209 | 0.1313 | 0.0975 | 0.0480 | 0.0300 |
| 55 | −0.0026 | 0.0067 | 0.0298 | −0.0020 | 0.0079 | 0.0243 | 0.1325 | 0.1015 | 0.0517 | 0.0362 |
| 60 | −0.0026 | 0.0079 | 0.0322 | −0.0021 | 0.0090 | 0.0274 | 0.1335 | 0.1049 | 0.0550 | 0.0399 |

Column heading: $\Delta A_{340}$

* Time (min)
** Control

Part 2. Polymerization of Purified Tubulin in the Absence of Either Guanosine 5'-triphosphate or Glycerol This standard pharmacological test procedure measures the ability of a representative example of the invention to induce polymerization of purified tubulin in the absence of glycerol or guanosine 5'-triphosphate (GTP). All other conditions and data calculation were as given above in Part 1.

In the first experiment, the polymerization reaction mixture did not contain glycerol. In the absence of glycerol, highly purified tubulin undergoes very little spontaneous polymerization but paclitaxel is known to induce polymerization under these conditions. The data displayed in Table 15 show that Example 170 also induced polymerization in the absence of glycerol.

In the second experiment, GTP was absent from the reaction mixture. Normal tubulin polymerization requires energy released from GTP hydrolysis to drive subunit assembly, but paclitaxel is able to induce polymer formation even in the absence of GTP. The data displayed in Table 16 show that Example 170 also induced polymerization in the absence of GTP.

The results of both these experiments are consistent with the conclusion that Example 170 has a paclitaxel-like mechanism of action on tubulin polymerization.

TABLE 15

Evaluation of Example 170 and Paclitaxel in the Tubulin Polymerization Standard Pharmacological Test Procedure in the absence of glycerol

| | Example 170 | | Paclitaxel | | |
|---|---|---|---|---|---|
| Time (min) | 10 µM | 1 µM | 10 µM | 1 µM | Control |
| 0 | 0 | 0 | 0 | 0 | 0 |
| 5 | 0.0019 | 0.0005 | 0.0056 | 0.0014 | 0.0002 |
| 10 | 0.0049 | 0.0014 | 0.0279 | 0.0091 | 0.0007 |

Column heading: $\Delta A_{340}$

TABLE 15-continued

Evaluation of Example 170 and Paclitaxel in the Tubulin Polymerization Standard Pharmacological Test Procedure in the absence of glycerol

| | $\Delta A_{340}$ | | | | |
|---|---|---|---|---|---|
| | Example 170 | | Paclitaxel | | |
| Time (min) | 10 µM | 1 µM | 10 µM | 1 µM | Control |
| 15 | 0.0095 | 0.0024 | 0.0546 | 0.0198 | 0.0011 |
| 20 | 0.0153 | 0.0039 | 0.0801 | 0.0310 | 0.0018 |
| 25 | 0.0215 | 0.0054 | 0.1016 | 0.0412 | 0.0024 |
| 30 | 0.0280 | 0.0074 | 0.1188 | 0.0500 | 0.0033 |
| 35 | 0.0347 | 0.0097 | 0.1070 | 0.0576 | 0.0043 |
| 40 | 0.0422 | 0.0121 | 0.1142 | 0.0638 | 0.0048 |
| 45 | 0.0504 | 0.0149 | 0.1192 | 0.0691 | 0.0058 |
| 50 | 0.0595 | 0.0188 | 0.1238 | 0.0737 | 0.0069 |
| 55 | 0.0687 | 0.0222 | 0.1262 | 0.0773 | 0.0077 |
| 60 | 0.0783 | 0.0264 | 0.1293 | 0.0805 | 0.0094 |

TABLE 16

Evaluation of Example 170 and Paclitaxel in the Tubulin Polymerization Standard Pharmacological Test Procedure in the absence of GTP

| | $\Delta A_{340}$ | | | | |
|---|---|---|---|---|---|
| | Example 170 | | Paclitaxel | | |
| Time (min) | 20 µM | 5 µM | 20 µM | 5 µM | Control |
| 0 | 0 | 0 | 0 | 0 | 0 |
| 5 | 0.0364 | 0.0000 | 0.0204 | 0.0032 | −0.0010 |
| 10 | 0.0582 | 0.0009 | 0.0592 | 0.0160 | −0.0004 |
| 15 | 0.0735 | 0.0028 | 0.0933 | 0.0305 | 0.0019 |
| 20 | 0.0830 | 0.0046 | 0.1159 | 0.0445 | 0.0035 |
| 25 | 0.0921 | 0.0078 | 0.1288 | 0.0570 | 0.0078 |
| 30 | 0.1022 | 0.0107 | 0.1365 | 0.0674 | 0.0121 |
| 35 | 0.1086 | 0.0142 | 0.1409 | 0.0764 | 0.0167 |
| 40 | 0.1125 | 0.0180 | 0.1435 | 0.0843 | 0.0198 |
| 45 | 0.1192 | 0.0220 | 0.1449 | 0.0908 | 0.0241 |
| 50 | 0.1225 | 0.0265 | 0.1457 | 0.0962 | 0.0276 |
| 55 | 0.1264 | 0.0310 | 0.1456 | 0.1008 | 0.0333 |
| 60 | 0.1277 | 0.0357 | 0.1455 | 0.1046 | 0.0387 |

Immunofluorescence Standard Test Procedure for Analysis of Effects of Compounds on Morphology of Mitotic Spindle Microtubules in Cells Compounds that bind to tubulin or microtubules typically have profound and characteristic effects on the structure of the microtubules which comprise the mitotic spindle of dividing cells. Compounds such as vincristine and colchicine that inhibit normal tubulin polymerization cause a severe disruption and even disappearance of spindle microtubules. On the other hand, compounds such as paclitaxel that promote tubulin polymerization and stabilize microtubules cause the appearance of dense tubulin bundles or aggregates. These effects of compounds can be visualized by immunofluorescent staining of fixed cells.

PC-3 MM2 human prostate carcinoma cells were plated at $5 \times 10^4$ cells/chamber in 8-chamber microscope slides that had been treated with poly-D-lysine (Biocoat 8-well CultureSlide, Becton Dickinson). The cells were allowed to attach and grow for 24 hr before addition of compounds at the indicated concentrations. After an additional 18-20 hr of culture with compounds, cells were fixed directly on the slides with methanol at minus 20°, rehydrated in phosphate-buffered saline, and stained with a mouse monoclonal antibody to α-tubulin (clone DM 1A, Sigma) followed by F(ab')$_2$ fragments of goat anti-mouse IgG, FITC conjugate (Jackson Immunoresearch). Cells were also stained with Hoescht 33258 to visualize DNA. Cells were viewed with a Zeiss fluorescence microscope under epi-illumination, and digital images were captured with a MTI Model DC330 video camera using Optimas V software. Images were processed using Corel PhotoPaint.

As displayed in Table 17, representative compounds or this invention produced marked bundling or aggregation of spindle microtubules in dividing cells. The patterns of microtubule bundling were similar to that produced by paclitaxel. When tested at equi-potent concentrations (i.e., at a concentration of each compound equal to eight times its $IC_{50}$ value in the 3-day MTS cytotoxicity assay), paclitaxel produced predominantly bipolar structures in which the microtubules appeared to be shortened and condensed. The compounds of this invention typically produced two, three, or four dense, circular bundles with intense fluorescence. The microtubule disrupting agents, vincristine and colchicine, produced patterns that were quite distinct from the compounds described here. These results are consistent with the conclusion that the compounds of this invention promote tubulin polymerization, as does paclitaxel.

TABLE 17

Evaluation of Representative Compounds of this Invention on Morphology of Mitotic Spindle Microtubutes in PC-3 MM2 Cells Determined by the Immunofluorescence Standard Pharmacological Test Procedure

| Ex. | Concentration (µM) | Appearance of Mitotic Spindle Microtubules |
|---|---|---|
| 35 | 0.54 | Less tightly condensed, greater variety of abnormal structures, including "tangled spaghetti" |
| 169 | 6.41 | Dense, compact, highly fluorescent bundles, roughly circular in shape, 2-4 per cell |
| 170 | 1.74 | Dense, compact, highly fluorescent bundles, roughly circular in shape, 2-4 per cell |
| 175 | 0.74 | Dense, compact, highly fluorescent bundles, roughly circular in shape, 2-4 per cell |
| 178 | 1.91 | Rigid spikes emanating from a central core: "sea urchin" appearance |
| 188 | 0.24 | Dense, compact, highly fluorescent bundles, roughly circular in shape, 2-4 per cell |
| 198 | 2.10 | Dense, compact, highly fluorescent bundles, roughly circular in shape, 2-4 per cell |
| 208 | 0.26 | Dense, compact, highly fluorescent bundles, roughly circular in shape, up to 8 per cell |
| 211 | 0.89 | Dense, compact, highly fluorescent bundles, roughly circular in shape, 2-4 per cell |
| Paclitaxel | 0.016 | Dense, compact, highly fluorescent bundles, typically bipolar |
| Vincristine | 0.008 | Multiple abnormal structures, many resembling partially disrupted spindles |
| Colchicine | 0.064 | Almost completely depolymerized microtubules, sometimes with multiple small flecks of brighter fluorescence |

Standard Pharmacological Test Procedure of Antitumor Activity in Athymic Mice Bearing Human Tumor Xenografts The tumors used were H157 human non-small cell lung carcinoma, U87MG human glioblastoma, LOX human melanoma, and DLD1 human colon adenocarcinoma. Cells were cultured in RPMI-1640 medium with L-glutamine, supplemented with 10% heat-inactivated fetal calf serum, 100 units/ml penicillin and 100 µg/ml streptomycin. Cells were injected subcutaneously into the flank of outbred nu/nu mice. About 5 days later tumors were staged and those around 100 mg were selected for use. Tumor weights were calculated from measurements of length in two dimensions.

Compounds for test were prepared in Klucel and administered to mice by intraperitoneal injection (0.5 ml volume) or by oral gavage (0.2 ml volume). Typically, the compounds of this invention were given twice per day for 14 days at the doses indicated in the tables. Each experimental group contained 10 animals unless otherwise indicated. The control group (also 10 animals) received Klucel only. Tumor weights were estimated every 3 to 5 days in most experiments (every 7 days in one experiment).

Individual experiments are displayed in Tables 18-28.

TABLE 18

Evaluation of Example 170 on Growth of Human H157 Non-small Cell Lung Carcinoma in Athymic Mice: Comparison of Intraperitoneal and Oral Dosing

| Treatment | Parameter | Day 0 | Day 7 | Day 10 | Day 14 | Day 16 | Day 18 | Day 21 |
|---|---|---|---|---|---|---|---|---|
| Klucel | MTW | 121 | 509 | 756 | 1298 | 1583 | 1752 | 2879 |
| Ex. 170 | MTW | 128 | 221 | 287 | 567 | 755 | 1163 | 2467 |
| 25 mg/kg | T/C | 1.05 | 0.43 | 0.38 | 0.44 | 0.48 | 0.66 | 0.86 |
| bid, ip | p | | 0.001 | 0.001 | 0.001 | 0.009 | 0.062 | 0.282 |
| Ex. 170 | MTW | 125 | 191 | 235 | 489 | 591 | 816 | 1835 |
| 25 mg/kg | T/C | 1.03 | 0.37 | 0.31 | 0.38 | 0.37 | 0.47 | 0.64 |
| bid, po | p | | 0.0005 | 0.0003 | 0.0003 | 0.0025 | 0.0065 | 0.052 |

Notes:
1. MTW = mean tumor weight = mean weight of tumors in all animals of the group. Each group had 10 animals.
2. Animals were staged on day 0 and dosed on days 1-14.
3. T/C = MTW of treated animals on day n/MTW of control animals on day n.
4. p = p value, Student's T-test.
5. No deaths in experimental groups.

TABLE 19

Evaluation of Example 170 on Growth of Human H157 Non-small Cell Lung Carcinoma in Athymic Mice: Comparison of Oral Dosing at Three Levels

| Treatment | Parameter | Day 0 | Day 4 | Day 8 | Day 12 | Day 14 | Day 17 |
|---|---|---|---|---|---|---|---|
| Klucel | MTW | 117 | 270 | 549 | 1066 | 1632 | 2314 |
| Ex. 170 | MTW | 127 | 142 | 194 | 428 | 602 | 839 |
| 25 mg/kg | T/C | 1.08 | 0.53 | 0.35 | 0.40 | 0.37 | 0.36 |
| bid, po | p | | 0.002 | 0.001 | 0.003 | 0.001 | 0.001 |
| Ex. 170 | MTW | 126 | 188 | 275 | 464 | 748 | 965 |
| 12.5 mg/kg | T/C | 1.08 | 0.70 | 0.50 | 0.44 | 0.46 | 0.42 |
| bid, po | p | | 0.018 | 0.005 | 0.004 | 0.004 | 0.002 |
| Ex. 170 | MTW | 121 | 221 | 377 | 643 | 1030 | 1147 |
| 6.3 mg/kg | T/C | 1.03 | 0.82 | 0.69 | 0.60 | 0.63 | 0.50 |
| bid, po | p | | 0.130 | 0.044 | 0.023 | 0.024 | 0.003 |

Notes:
1. MTW = mean tumor weight = mean weight of tumors in all animals of the group. Each group had 10 animals.
2. Animals were staged on day 0 and dosed on days 1-14.
3. T/C = MTW of treated animals on day n/MTW of control animals on day n.
4. p = p value, Student's T-test.
5. One death each in 25 and 12.5 groups.

TABLE 20

Evaluation of Example 170 on Growth of Human H157 Non-small Cell Lung Carcinoma in Athymic Mice: Comparison of Oral Dosing Once or Twice Per Day

| Treatment | Parameter | Day 0 | Day 4 | Day 9 | Day 12 | Day 14 | Day 18 |
|---|---|---|---|---|---|---|---|
| Klucel | MTW | 111 | 334 | 577 | 1037 | 2237 | 3782 |
| Ex. 170 | MTW | 126 | 219 | 287 | 431 | 766 | 1550 |
| 25 mg/kg | T/C | 1.14 | 0.65 | 0.50 | 0.42 | 0.34 | 0.41 |
| qd, po | p | | 0.03 | 0.01 | 0.0006 | 0.0006 | 0.005 |
| Ex. 170 | MTW | 115 | 123 | 158 | 176 | 413 | 817 |

TABLE 20-continued

Evaluation of Example 170 on Growth of Human H157 Non-small Cell Lung Carcinoma in Athymic Mice: Comparison of Oral Dosing Once or Twice Per Day

| Treatment | Parameter | Day 0 | Day 4 | Day 9 | Day 12 | Day 14 | Day 18 |
|---|---|---|---|---|---|---|---|
| 25 mg/kg bid, po | T/C | 1.04 | 0.37 | 0.27 | 0.17 | 0.18 | 0.22 |
| | p | | 4E−05 | 5E−05 | 2E−06 | 9E−06 | 2.5E−05 |

Notes:
1. MTW = mean tumor weight = mean weight of tumors in all animals of the group. Each group had 10 animals.
2. Animals were staged on day 0 and dosed on days 1-14.
3. T/C = MTW of treated animals on day n/MTW of control animals on day n.
4. p = p value, Student's T-test.
5. No deaths in experimental groups.

TABLE 21

Evaluation of Example 170, Example 169, and Example 133 on Growth of Human H157 Non-small Cell Lung Carcinoma in Athymic Mice:

| Treatment | Parameter | Day 0 | Day 5 | Day 7 | Day 10 | Day 14 | Day 17 |
|---|---|---|---|---|---|---|---|
| Klucel | MTW | 119 | 300 | 425 | 638 | 1385 | 1940 |
| Ex. 170 | MTW | 136 | 215 | 253 | 345 | 540 | 1203 |
| 25 mg/kg bid, ip | T/C | 1.14 | 0.72 | 0.60 | 0.54 | 0.39 | 0.62 |
| | p | | 0.07 | 0.05 | 0.07 | 0.03 | 0.10 |
| Ex. 169 | MTW | 136 | 277 | 425 | 716 | 1641 | 1869 |
| 25 mg/kg bid, ip | T/C | 1.14 | 0.92 | 1.00 | 1.12 | 1.18 | 0.96 |
| Ex. 133 | MTW | 139 | 262 | 367 | 558 | 1103 | 1888 |
| 25 mg/kg bid, ip | T/C | 1.17 | 0.87 | 0.86 | 0.87 | 0.80 | 0.97 |

Notes:
1. MTW = mean tumor weight = mean weight of tumors in all animals of the group. Each group had 10 animals.
2. Animals were staged on day 0 and dosed on days 1-14.
3. T/C = MTW of treated animals on day n/MTW of control animals on day n.
4. p = p value, Student's T-test.
5. One death in Example 170 group.

TABLE 22

Evaluation of Example 170 and Example 208 on Growth of Human H157 Non-small Cell Lung Carcinoma in Athymic Mice

| Treatment | Parameter | Day 0 | Day 3 | Day 7 | Day 10 | Day 14 | Day 17 | Day 21 |
|---|---|---|---|---|---|---|---|---|
| Klucel | MTW | 138 | 213 | 580 | 1028 | 1948 | 3041 | 3453 |
| Ex. 170 | MTW | 159 | 123 | 162 | 236 | 391 | 562 | 1335 |
| 50 mg/kg bid, then qd, ip | T/C | 1.15 | 0.58 | 0.28 | 0.23 | 0.20 | 0.18 | 0.39 |
| | p | | 0.002 | 0.0005 | 0.001 | 0.001 | 0.0005 | 0.006 |
| Ex. 208 50 mg/kg bid, then qd, ip | MTW | 158 | 187 | 287 | 367 | See note 5 | See note 5 | See note 5 |

Notes:
1. MTW = mean tumor weight = mean weight of tumors in all animals of the group. Each group had 10 animals.
2. Animals were staged on day 0 and dosed on days 1-14. Dosing was bid days 1-6, then qd days 7-14.
3. T/C = MTW of treated animals on day n/MTW of control animals on day n.
4. p = p value, Student's T-test.
5. Dosing of Example 208 was stopped after 10 days because of toxicity.
6. 1 death in Example 170 group.

TABLE 23

Evaluation of Example 35 on Growth of Human H157 Non-small Cell Lung Carcinoma in Athymic Mice

| Treatment | Parameter | Day 0 | Day 6 | Day 10 | Day 14 | Day 18 | Day 21 | Day 25 |
|---|---|---|---|---|---|---|---|---|
| Klucel | MTW | 87 | 255 | 334 | 721 | 1212 | 1148 | 2076 |
| Ex. 35 | MTW | 91 | 305 | 514 | 1372 | 2192 | 2296 | 2154 |
| 50 mg/kg | T/C | 1.05 | 1.20 | 1.54 | 1.90 | 1.81 | 2.00 | 1.04 |
| bid, ip | p | | | | | | | |

Notes:
1. MTW = mean tumor weight = mean weight of tumors in all animals of the group. Each group had 10 animals.
2. Animals were staged on day 0 and dosed on days 1-14
3. T/C = MTW of treated animals on day n/MTW of control animals on day n.
4. p = p value, Student's T-test.
5. No deaths in experimental group.

TABLE 24

Evaluation of Example 188 on Growth of Human H157 Non-small Cell Lung Carcinoma in Athymic Mice

| Treatment | Parameter | Day 0 | Day 4 | Day 7 | Day 10 |
|---|---|---|---|---|---|
| Klucel | MTW | 139 | 325 | 516 | 942 |
| Ex. 188 | MTW | 154 | 385 | 560 | 1037 |
| 50 mg/kg | T/C | 1.11 | 1.18 | 1.08 | 1.10 |
| bid, ip | p | | 0.15 | 0.33 | 0.31 |

Notes:
1. MTW = mean tumor weight = mean weight of tumors in all animals of the group. Each group had 10 animals.
2. Animals were staged on day 0 and dosed on days 1-10.
3. T/C = MTW of treated animals on day n/MTW of control animals on day n.
4. p = p value, Student's T-test.
5. Dosing of Example 188 was stopped after 10 days because of toxicity.

TABLE 25

Evaluation of Example 170 on Growth of Human U87MG Glioblastoma in Athymic Mice: Comparison of Intraperitoneal Dosing at Three Levels

| Treatment | Parameter | Day 0 | Day 4 | Day 7 | Day 10 | Day 14 | Day 17 | Day 19 |
|---|---|---|---|---|---|---|---|---|
| Klucel | MTW | 160 | 258 | 406 | 504 | 1025 | 1656 | 2257 |
| Ex. 170 | MTW | 156 | 134 | 145 | 111 | 144 | 200 | 296 |
| 25 mg/kg | T/C | 0.98 | 0.52 | 0.36 | 0.22 | 0.14 | 0.12 | 0.13 |
| bid, ip | p | | 2E–07 | 8.8E–07 | 1.5E–08 | 6.9E–09 | 3.3E–09 | 2.8E–06 |
| Ex. 170 | MTW | 156 | 190 | 232 | 314 | 664 | 1155 | 1896 |
| 10 mg/kg | T/C | 0.98 | 0.74 | 0.57 | 0.62 | 0.65 | 0.70 | 0.84 |
| bid, ip | p | | 0.0010 | 0.0001 | 0.0005 | 0.0027 | 0.0084 | 0.174 |
| Ex. 170 | MTW | 161 | 213 | 320 | 414 | 849 | 1631 | 2567 |
| 5 mg/kg | T/C | 1.01 | 0.83 | 0.79 | 0.82 | 0.83 | 0.99 | 1.14 |
| bid, ip | p | | 0.028 | 0.052 | 0.100 | 0.157 | 0.462 | 0.259 |

Notes:
1. MTW = mean tumor weight = mean weight of tumors in all animals of the group. Each group had 10 animals.
2. Animals were staged on day 0 and dosed on days 1-14.
3. T/C = MTW of treated animals on day n/MTW of control animals on day n.
4. p = p value, Student's T-test.
5. No deaths in experimental groups.

TABLE 26

Evaluation of Representative Compounds of this Invention on Growth of Human U87MG Glioblastoma in Athymic Mice

| Treatment | Parameter | Day 0 | Day 3 | Day 7 | Day 9 |
|---|---|---|---|---|---|
| Klucel | MTW | 128 | 213 | 363 | 537 |
| Ex. 170 | MTW | 128 | 138 | 120 | 112 |
| 25 mg/kg | T/C | 1.00 | 0.65 | 0.33 | 0.21 |
| bid, ip | | | | | |
| Ex. 211 | MTW | 130 | 171 | 266 | 374 |
| 25 mg/kg | T/C | 1.02 | 0.80 | 0.73 | 0.70 |
| bid, ip | | | | | |
| Ex. 198 | MTW | 127 | 198 | 305 | 559 |
| 25 mg/kg | T/C | 0.99 | 0.93 | 0.84 | 1.04 |
| bid, ip | | | | | |
| Ex. 178 | MTW | 124 | 112 | See note 4 | See note 4 |
| 25 mg/kg | T/C | 0.97 | 0.53 | | |
| bid, ip | | | | | |

TABLE 26-continued

Evaluation of Representative Compounds of this Invention on Growth of Human U87MG Glioblastoma in Athymic Mice

| Treatment | Parameter | Day 0 | Day 3 | Day 7 | Day 9 |
|---|---|---|---|---|---|
| Ex. 175 | MTW | 138 | 176 | 239 | 433 |
| 25 mg/kg bid, ip | T/C | 1.08 | 0.83 | 0.66 | 0.81 |
| Ex. 35 | MTW | 135 | 180 | 226 | 427 |
| 25 mg/kg bid, ip | T/C | 1.05 | 0.85 | 0.62 | 0.80 |
| Ex. 169 | MTW | 136 | 187 | 254 | 464 |
| 25 mg/kg bid, ip | T/C | 1.06 | 0.88 | 0.70 | 0.86 |

Notes:
1. MTW = mean tumor weight = mean weight of tumors in all animals of the group. Each group had 10 animals.
2. Animals were staged on day 0 and dosed on days 1-9.
3. T/C = MTW of treated animals on day n/MTW of control animals on day n.
4. Dosing of Example 178 was stopped after 4 days because of toxicity.

TABLE 27

Evaluation of Example 170 on Growth of Human LOX Melanoma in Athymic Mice: Comparison of Intraperitoneal and Oral Dosing

| Treatment | Parameter | Day 0 | Day 7 | Day 14 |
|---|---|---|---|---|
| Klucel | RTG | 1 | 11.51 | 40.53 |
| Ex. 170 | RTG | 1 | 4.91 | 14.77 |
| 25 mg/kg | T/C | 1 | 0.43 | 0.36 |
| bid, ip | p | | 0.05 | 0.08 |
| Ex. 170 | RTG | 1 | 8.06 | 35.55 |
| 10 mg/kg | T/C | | 0.70 | 0.88 |
| bid, ip | p | | 0.38 | 0.53 |
| Ex. 170 | RTG | 1 | 10.17 | 40.49 |
| 25 mg/kg | T/C | | 0.88 | 1.00 |
| bid, po | p | | 0.61 | 0.53 |

Notes:
1. RTG = relative tumor growth = mean tumor weight on day n/mean tumor weight of same group on day 0. 10 animals in control group, 5 in CL 376894 groups.
2. Animals were staged on day 0 and dosed on days 1-14.
3. T/C = RTG of treated animals on day n/RTG of control animals on day n.
4. p = p value, Student's T-test.
5. No deaths in experimental groups.

TABLE 28

Evaluation of Example 170 on Growth of Human DLD1 Colon Carcinoma in Athymic Mice: Comparison of Intraperitoneal and Oral Dosing

| Treatment | Parameter | Day 0 | Day 7 | Day 14 | Day 21 |
|---|---|---|---|---|---|
| Klucel | RTG | 1 | 3.17 | 9.62 | 18.11 |
| Ex. 170 | RTG | 1 | 3.60 | 8.08 | 14.58 |
| 25 mg/kg | T/C | | 1.14 | 0.84 | 0.81 |
| bid, ip | p | | 0.87 | 0.20 | 0.31 |
| Ex. 170 | RTG | 1 | 3.95 | 9.64 | 17.32 |
| 25 mg/kg | T/C | | 1.25 | 1.00 | 0.96 |
| bid, po | p | | 0.96 | 0.56 | 0.48 |

Notes:
1. RTG = relative tumor growth = mean tumor weight on day n/mean tumor weight of same group on day 0. Each group had 10 animals.
2. Animals were staged on day 0 and dosed on days 1-14.
3. T/C = RTG of treated animals on day n/RTG of control animals on day n.
4. p = p value, Student's T-test.
5. No deaths in experimental groups.

Based on the results of these standard pharmacological test procedures, the compounds of this invention are useful as agents for treating, inhibiting or controlling the growth of cancerous tumor cells and associated diseases in a mammal in need thereof by interacting with tubulin and microtubules and promotion of microtubule polymerization. The compounds of the invention are also useful for the treatment or prevention of multiple drug resistant (MDR). The effective dosage of active ingredient employed may vary depending on the particular compound employed, the mode of administration and severity of the condition being treated. However, in general satisfactory results are obtained when the compounds of the invention are administered in amounts ranging from about 0.10 to about 100 mg/kg of body weight per day. A preferred regimen for optimum results would be from about 1 mg to about 20 mg/kg of body weight per day and such dosage units are employed that a total of from about 70 mg to about 1400 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes. The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

The following examples are representative compounds of this invention which are useful as promoters of microtubule polymerization and as anticancer agents.

EXAMPLE 1

7-(1-azepanyl)-5-chloro-6-phenyl[1,2,4]triazolo[1,5-a]pyrimidine

EXAMPLE 2

5-chloro-6-(2,6-difluorophenyl)-7-(4-methyl-1-piperidinyl)[1,2,4]triazolo[1,5-a]pyrimidine

EXAMPLE 3

5-chloro-6-(4-methoxyphenyl)-7-(1-piperidinyl)[1,2,4]triazolo[1,5-a]pyrimidine

EXAMPLE 4

5-chloro-6-(2-chloro-6-fluorophenyl)-7-(4-methyl-1-piperidinyl)[1,2,4]triazolo[1,5-a]pyrimidine

EXAMPLE 5

7-(1-azepanyl)-5-chloro-6-(2-chloro-6-fluorophenyl)[1,2,4]triazolo[1,5-a]pyrimidine

EXAMPLE 6

5-chloro-6-(2-chloro-6-fluorophenyl)-7-(2-methyl-1-piperidinyl)[1,2,4]triazolo[1,5-a]pyrimidine

EXAMPLE 7

5-chloro-6-(2-chloro-6-fluorophenyl)-7-(4-thiomorpholinyl)[1,2,4]triazolo[1,5-a]pyrimidine

EXAMPLE 8 methyl [[5-chloro-6-(2-chloro-6-fluorophenyl)[1,2,4]triazolo[1,5-a]pyrimidin-7-yl](methyl)amino]acetate

EXAMPLE 9

5-chloro-6-(2-chloro-6-fluorophenyl)-N-(1,1,3,3-tetramethylbutyl)[1,2,4]triazolo[1,5-a]pyrimidin-7-amine

EXAMPLE 10

7-(1-azepanyl)-5-chloro-6-(4-methoxyphenyl)[1,2,4]triazolo[1,5-a]pyrimidine

EXAMPLE 11

7-(1-azepanyl)-6-(4-bromophenyl)-5-chloro[1,2,4]triazolo[1,5-a]pyrimidine

EXAMPLE 12

5-chloro-7-(1-piperidinyl)-6-[2-(trifluoromethyl)phenyl][1,2,4]triazolo[1,5-a]pyrimidine

EXAMPLE 13

6-(4-tert-butylphenyl)-5-chloro-7-(4-methyl-1-piperidinyl)[1,2,4]triazolo[1,5-a]pyrimidine

EXAMPLE 14

5-chloro-6-(4-methoxyphenyl)-7-(4-methyl-1-piperidinyl)[1,2,4]triazolo[1,5-a]pyrimidine

EXAMPLE 15

5-chloro-6-(4-methoxyphenyl)-7-(3-methyl-1-piperidinyl)[1,2,4]triazolo[1,5-a]pyrimidine

EXAMPLE 16

6-(4-bromophenyl)-5-chloro-7-(3-methyl-1-piperidinyl)[1,2,4]triazolo[1,5-a]pyrimidine

EXAMPLE 17

5-chloro-6-(3,4-difluorophenyl)-7-(4-methyl-1-piperidinyl)[1,2,4]triazolo[1,5-a]pyrimidine

EXAMPLE 18

5-chloro-6-(2,6-dichlorophenyl)-7-(2-methyl-1-pyrrolidinyl)[1,2,4]triazolo[1,5-a]pyrimidine

EXAMPLE 19

5-chloro-6-(2-chlorophenyl)-7-(2-methyl-1-pyrrolidinyl)[1,2,4]triazolo[1,5-a]pyrimidine

EXAMPLE 20

7-(1-azepanyl)-5-chloro-6-(3-chloro-4-methoxyphenyl)[1,2,4]triazolo[1,5-a]pyrimidine

EXAMPLE 21

5-chloro-6-(3-chloro-4-methoxyphenyl)-7-(4-methyl-1-piperidinyl)[1,2,4]triazolo[1,5-a]pyrimidine

EXAMPLE 22

5-chloro-6-(3-chloro-4-methoxyphenyl)-7-(2-methyl-1-piperidinyl)[1,2,4]triazolo[1,5-a]pyrimidine

EXAMPLE 23

6-(4-tert-butylphenyl)-5-chloro-7-(2-methyl-1-piperidinyl)[1,2,4]triazolo[1,5-a]pyrimidine

EXAMPLE 24

5-chloro-7-(2-methyl-1-piperidinyl)-6-[3-(trifluoromethyl)phenyl][1,2,4]triazolo[1,5-a]pyrimidine

EXAMPLE 25

Diethyl 2-[6-(2,6-difluorophenyl)-5-ethoxy[1,2,4]triazolo[1,5-a]pyrimidin-7-yl]malonate

EXAMPLE 26

7-(azepanyl)-5-chloro-6-{2-chloro-6-nitrophenyl}[1,2,4]triazolo[1,5-a]pyrimidine

EXAMPLE 27

5-chloro-6-(2-chloro-6-fluorophenyl)-N-ethyl-N-(2-methyl-2-propenyl)[1,2,4]triazolo[1,5-a]pyrimidin-7-amine

EXAMPLE 28

5-chloro-6-(2-chloro-6-fluorophenyl)-N-(2,2,2-trifluoroethyl)[1,2,4]triazolo[1,5-a]pyrimidin-7-amine

EXAMPLE 29

5-chloro-6-(2-chloro-6-fluorophenyl)-N-[(2,2-dichlorocyclopropyl)methyl]-N-methyl[1,2,4]triazolo[1,5-a]pyrimidin-7-amine

EXAMPLE 30

1-[5-chloro-6-(2-chloro-6-fluorophenyl)[1,2,4]triazolo[1,5-a]pyrimidin-7-yl]-3-piperidinol

EXAMPLE 31

N-bicyclo[2,2,1]hept-2-yl-5-chloro-6-(3-chloro-4-methoxyphenyl)[1,2,4]triazolo[1,5-a]pyrimidin-7-amine

EXAMPLE 32

5-chloro-6-(2,5-difluorophenyl)-N-dodecyl[1,2,4]triazolo[1,5-a]pyrimidin-7-amine

EXAMPLE 33

5-chloro-7-(4-methyl-1-piperidinyl)-6-(2,3,6-trifluorophenyl)[1,2,4]triazolo[1,5-a]pyrimidine

EXAMPLE 34

N-[5-chloro-6-(2,3,6-trifluorophenyl)[1,2,4]triazolo[1,5-a]pyrimidin-7-yl]-N-isopropylamine

EXAMPLE 35

5-chloro-N-ethyl-N-(2-methyl-2-propenyl)-6-(2,3,6-trifluorophenyl)[1,2,4]triazolo[1,5-a]pyrimidin-7-amine

EXAMPLE 36

N-allyl-5-chloro-6-(2-chloro-6-fluorophenyl)-N-(2-methyl-2-propenyl)[1,2,4]triazolo[1,5-a]pyrimidin-7-amine

EXAMPLE 37

5-chloro-6-(2-chloro-6-fluorophenyl)[1,2,4]triazolo[1,5-a]pyrimidin-7-amine

EXAMPLE 38

5-chloro-6-(3-chloro-4-methoxyphenyl)-N-cycloheptyl[1,2,4]triazolo[1,5-a]pyrimidin-7-amine

EXAMPLE 39

5-chloro-6-(3-chloro-4-methoxyphenyl)-7-(3,3-dimethyl-1-piperidinyl)[1,2,4]triazolo[1,5-a]pyrimidine

EXAMPLE 40

5-chloro-N-(3-chloropropyl)-N-methyl-6-(2,3,6-trifluorophenyl)[1,2,4]triazolo[1,5-a]pyrimidin-7-amine

EXAMPLE 41

7-(1-azocanyl)-5-chloro-6-(2,3,6-trifluorophenyl)[1,2,4]triazolo[1,5-a]pyrimidine

EXAMPLE 42

5-chloro-6-(2,6-difluorophenyl)-7-(3,6-dihydro-1(2H)-pyridinyl)[1,2,4]triazolo[1,5-a]pyrimidine

EXAMPLE 43

7-(1-azocanyl)-5-chloro-6-(2,6-difluorophenyl[1,2,4]triazolo[1,5-a]pyrimidine

EXAMPLE 44

5-methoxy-6-(2-chloro-6-fluorophenyl)-7-(4-methyl-1-piperidinyl)[1,2,4]triazolo[1,5-a]pyrimidine

EXAMPLE 45

[5-chloro-6-(2-chloro-6-fluorophenyl)[1,2,4]triazolo[1,5-a]pyrimidin-7-yl]methanol

EXAMPLE 46

1-[5-chloro-6-(2,6-difluorophenyl)[1,2,4]triazolo[1,5-a]pyrimidin-7-yl]-4-piperidinol

EXAMPLE 47

5-chloro-7-(4-chloro-1-piperidinyl)-6-(2,6-difluorophenyl)[1,2,4]triazolo[1,5-a]pyrimidine

EXAMPLE 48

5-chloro-7-(4-thiomorpholinyl)-6-(2,3,6-trifluorophenyl)[1,2,4]triazolo[1,5-a]pyrimidine

EXAMPLE 49

5-chloro-6-(2,6-difluorophenyl)-7-(2,4-dimethyl-1-piperidinyl)[1,2,4]triazolo[1,5-a]pyrimidine

EXAMPLE 50

7-(4-methyl-1-piperidinyl)-5-amino-6-(2-chloro-6-fluorophenyl)[1,2,4]triazolo[1,5-a]pyrimidine

EXAMPLE 51

5-chloro-6-(2,6-difluorophenyl)-7-(2,5-dihydro-1H-pyrrol-1-yl)[1,2,4]triazolo[1,5-a]pyrimidine

EXAMPLE 52

5-chloro-6-(2-chloro-6-fluorophenyl)-7-(2,5-dimethyl-2,5-dihydro-1H-pyrrol-1-yl)[1,2,4]triazolo[1,5-a]pyrimidine

EXAMPLE 53

5-chloro-6-(2-chloro-6-fluorophenyl)-7-(2-ethyl-1H-imidazol-1-yl)[1,2,4]triazolo[1,5-a]pyrimidine

EXAMPLE 54

7-(4-bromo-1-piperidinyl)-5-chloro-6-(2-chloro-6-fluorophenyl)[1,2,4]triazolo[1,5-a]pyrimidine

EXAMPLE 55

5-chloro-6-(2-methylphenyl)-7-(4-thiomorpholinyl)[1,2,4]triazolo[1,5-a]pyrimidine

EXAMPLE 56

6-(2-bromophenyl)-N-(sec-butyl)-5-chloro[1,2,4]triazolo[1,5-a]pyrimidin-7-amine

EXAMPLE 57

5-chloro-N-ethyl-6-(4-methoxyphenyl)-N-(2-methyl-2-propenyl)[1,2,4]triazolo[1,5-a]pyrimidin-7-amine

EXAMPLE 58

5-chloro-6-(4-methoxyphenyl)-7-(4-thiomorpholinyl)[1,2,4]triazolo[1,5-a]pyrimidine

EXAMPLE 59

5-chloro-7-(4-chloro-1-piperidinyl)-6-[2-(trifluoromethyl)phenyl][1,2,4]triazolo[1,5-a]pyrimidine

EXAMPLE 60

5-chloro-6-(2-chloro-6-fluorophenyl)-7-[4-(trifluoromethyl)-1-piperidinyl][1,2,4]triazolo[1,5-a]pyrimidine

EXAMPLE 61

7-(4-bromo-1-piperidinyl)-5-chloro-6-(2,6-difluorophenyl)[1,2,4]triazolo[1,5-a]pyrimidine

EXAMPLE 62

7-(4-bromo-1-piperidinyl)-5-chloro-6-(2-chlorophenyl)[1,2,4]triazolo[1,5-a]pyrimidine

EXAMPLE 63

5-chloro-N-ethyl-N-(2-methyl-2-propenyl)-6-(2,4,6-trifluorophenyl)[1,2,4]triazolo[1,5-a]pyrimidin-7-amine

EXAMPLE 64

5-chloro-N-isopropyl-6-(2,4,6-trifluorophenyl)[1,2,4]triazolo[1,5-a]pyrimidin-7-amine

EXAMPLE 65

5-chloro-7-(4-thiomorpholinyl)-6-(2,4,6-trifluorophenyl)[1,2,4]triazolo[1,5-a]pyrimidine

EXAMPLE 66

7-(1-azepanyl)-5-chloro-6-(2,4,6-trifluorophenyl)[1,2,4]triazolo[1,5-a]pyrimidine

EXAMPLE 67

5-chloro-6-(2-chloro-6-fluorophenyl)-7-[2-(1-pyrrolidinyl)-1-cyclopenten-1-yl][1,2,4]triazolo[1,5-a]pyrimidine

EXAMPLE 68

5-chloro-7-(4-isopropyl-1-piperidinyl)-6-(4-methoxyphenyl)[1,2,4]triazolo[1,5-a]pyrimidine

EXAMPLE 69

5-chloro-7-(2,4-dimethyl-1-piperidinyl)-6-(4-methoxyphenyl)[1,2,4]triazolo[1,5-a]pyrimidine

EXAMPLE 70

5-chloro-7-[ethyl(2-methyl-2-propenyl)amino]-6-{4-nitrophenyl}[1,2,4]triazolo[1,5-a]pyrimidine

EXAMPLE 71

7-(1-azepanyl)-5-chloro-6-{4-nitrophenyl}[1,2,4]triazolo[1,5-a]pyrimidine

EXAMPLE 72

N-bicyclo[2.2.1]hept-2-yl-5-chloro-6-(2,4,6-trifluorophenyl)[1,2,4]triazolo[1,5-a]pyrimidin-7-amine

EXAMPLE 73

5-chloro-6-(2,6-difluorophenyl)-N-(2,2,2-trifluoroethyl)[1,2,4]triazolo[1,5-a]pyrimidin-7-amine

EXAMPLE 74

5-chloro-6-(2-chlorophenyl)-N-(2,2,2-trifluoroethyl)[1,2,4]triazolo[1,5-a]pyrimidin-7-amine

EXAMPLE 75

5-chloro-6-(2-chloro-6-fluorobenzyl)-7-tetrahydro-2-furanyl[1,2,4]triazolo[1,5-a]pyrimidine

EXAMPLE 76

7-(allylsulfanyl)-5-chloro-6-(2-chloro-6-fluorophenyl)[1,2,4]triazolo[1,5-a]pyrimidine

EXAMPLE 77

5-chloro-N-ethyl-6-mesityl-N-(2-methyl-2-propenyl)[1,2,4]triazolo[1,5-a]pyrimidin-7-amine

EXAMPLE 78

5-chloro-N-ethyl-6-(2-methoxyphenyl)-N-(2-methyl-2-propenyl)[1,2,4]triazolo[1,5-a]pyrimidin-7-amine

EXAMPLE 79

5-chloro-6-(2-chloro-6-fluorophenyl)-N-hexyl[1,2,4]triazolo[1,5-a]pyrimidin-7-amine

EXAMPLE 80

5-chloro-7-(4-methyl-1-piperidinyl)-6-[4-(methylsulfanyl)phenyl][1,2,4]triazolo[1,5-a]pyrimidine

EXAMPLE 81

5-chloro-N-ethyl-N-(2-methyl-2-propenyl)-6-[4-(methylsulfanyl)phenyl][1,2,4]triazolo[1,5-a]pyrimidin-7-amine

EXAMPLE 82

N-(sec-butyl)-5-chloro-6-[4-(methylsulfanyl)phenyl][1,2,4]triazolo[1,5-a]pyrimidin-7-amine

EXAMPLE 83

5-chloro-6-[4-(methylsulfanyl)phenyl]-7-(4-thiomorpholinyl)[1,2,4]triazolo[1,5-a]pyrimidine

EXAMPLE 84

5-chloro-6-[2,6-dichloro-4-(trifluoromethylphenyl]-7-(4-methyl-1-piperidinyl)[1,2,4]triazolo[1,5-a]pyrimidine

EXAMPLE 85

7-(1-azepanyl)-5-chloro-6-[2,6-dichloro-4-(trifluoromethyl)phenyl][1,2,4]triazolo[1,5-a]pyrimidine

EXAMPLE 86

5-chloro-6-(2-chloro-6-fluorophenyl)-7-[(2,2,2-trifluoroethyl)sulfanyl][1,2,4]triazolo[1,5-a]pyrimidine

EXAMPLE 87

5-chloro-6-(2-chloro-6-fluorophenyl )-7-(4,4-dimethyl-1-piperidinyl)[1,2,4]triazolo[1,5-a]pyrimidine

EXAMPLE 88

5-chloro-6-[2,6-dichloro-4-(trifluoromethyl)phenyl]-N-ethyl-N-(2-methyl-2-propenyl)[1,2,4]triazolo[1,5-a]pyrimidin-7-amine

EXAMPLE 89

5-chloro-6-[2,6-dichloro-4-(trifluoromethyl)phenyl]-7-(4-thiomorpholinyl)[1,2,4]triazolo[1,5-a]pyrimidine

EXAMPLE 90

5-chloro-6-(3,5-difluorophenyl)-7-(4-methyl-1-piperidinyl)[1,2,4]triazolo[1,5-a]pyrimidine

EXAMPLE 91

5-chloro-6-(2-chloro-6-fluorophenyl)-7-(isopropylsulfanyl)[1,2,4]triazolo[1,5-a]pyrimidine

EXAMPLE 92

5-chloro-6-(2-chloro-6-fluorophenyl)-7-tetrahydro-2-furanyl[1,2,4]triazolo[1,5-a]pyrimidine

EXAMPLE 93

4-[5-chloro-7-(4-methyl-1-piperidinyl)[1,2,4]triazolo[1,5-a]pyrimidin-6-yl]aniline

EXAMPLE 94

N-{4-[5-chloro-7-(4-methyl-1-piperidinyl)[1,2,4]triazolo[1,5-a]pyrimidin-6-yl]phenyl}acetamide

EXAMPLE 95

[5-chloro-6-(2-chloro-6-fluorophenyl)[1,2,4]triazolo[1,5-a]pyrimidin-7-yl]methyl acetate

EXAMPLE 96

5-chloro-6-(2-chloro-6-fluorophenyl)-7-(chloromethyl)[1,2,4]triazolo[1,5-a]pyrimidine

EXAMPLE 97 diethyl 2-[6-(2-chloro-6-fluorophenyl)-7-(4-methyl-1-piperidinyl)[1,2,4]triazolo[1,5-a]pyrimidin-5-yl]malonate

EXAMPLE 98

7-(1-azepanylmethyl)-5-chloro-6-(2-chloro-6-fluorophenyl)[1,2,4]triazolo[1,5-a]pyrimidine

EXAMPLE 99

N-allyl-5-chloro-6-(2-chloro-6-fluorophenyl)-N-hexyl[1,2,4]triazolo[1,5-a]pyrimidin-7-amine

EXAMPLE 100

5-chloro-7-(4-methyl-1-piperidinyl)-6-[4-(trifluoromethoxy)phenyl][1,2,4]triazolo[1,5-a]pyrimidine

EXAMPLE 101

5-chloro-7-(4-methyl-1-piperidinyl)-6-(4-phenoxyphenyl[1,2,4]triazolo[1,5-a]pyrimidine

EXAMPLE 102

5-chloro-6-(2-chloro-6-fluorophenyl)-N-(cyclopropylmethyl)-N-propyl[1,2,4]triazolo[1,5-a]pyrimidin-7-amine

EXAMPLE 103

5-chloro-7-(2-methyl-1-piperidinyl)-6-(4-phenoxyphenyl)[1,2,4]triazolo[1,5-a]pyrimidine

EXAMPLE 104

5-chloro-6-{2-chloro-4-nitrophenyl}-7-(4-methyl-1-piperidinyl)[1,2,4]triazolo[1,5-a]pyrimidine

EXAMPLE 105

5-chloro-6-(4-chloro-2,3,5,6-tetrafluorophenyl)-N-cyclopentyl[1,2,4]triazolo[1,5-a]pyrimidin-7-amine

EXAMPLE 106

4-[5-chloro-2-methyl-7-(4-methyl-1-piperidinyl)[1,2,4]triazolo[1,5-a]pyrimidin-6-yl]-N,N-dimethylaniline

EXAMPLE 107

6-(2-chloro-6-fluorophenyl)-5-methyl-7-(4-methyl-1-piperidinyl)[1,2,4]triazolo[1,5-a]pyrimidine

EXAMPLE 108

5-chloro-6-(2-chloro-6-fluorophenyl)-7-[2-(1-pyrrolidinyl)-1-cyclohexen-1-yl][1,2,4]triazolo[1,5-a]pyrimidine

EXAMPLE 109

5-chloro-6-(2-chloro-6-fluorophenyl)-7-(methoxymethyl)[1,2,4]triazolo[1,5-a]pyrimidine

EXAMPLE 110

5-chloro-6-{2-chloro-4-nitrophenyl}-7-[ethyl(2-methyl-2-propenyl)amino][1,2,4]triazolo[1,5-a]pyrimidine

EXAMPLE 111

5-bromo-6-(2-chloro-6-fluorophenyl)-7-(isopropylsulfanyl)[1,2,4]triazolo[1,5-a]pyrimidine

EXAMPLE 112

5-chloro-N-cyclopentyl-6-(4-ethoxy-2,3,5,6-tetrafluorophenyl)[1,2,4]triazolo[1,5-a]pyrimidin-7-amine

EXAMPLE 113

5-chloro-N-methyl-N-(2-methyl-2-propenyl)-6-(2,4,6-trifluorophenyl)[1,2,4]triazolo[1,5-a]pyrimidin-7-amine

EXAMPLE 114

4-bromo-1-[5-chloro-6-(2-chloro-6-fluorophenyl)[1,2,4]triazolo[1,5-a]pyrimidin-7-yl]butyl acetate

EXAMPLE 115 diethyl 2-allyl-2-{[5-chloro-6-(2-chloro-6-fluorophenyl)[1,2,4]triazolo[1,5-a]pyrimidin-7-yl]oxy}malonate

EXAMPLE 116

6-(2-chloro-6-fluorophenyl)-N-ethyl-5-methyl[1,2,4]triazolo[1,5-a]pyrimidin-7-amine

EXAMPLE 117

N-butyl-5-chloro-N-ethyl-6-(2,3,4,5,6-pentafluorophenyl)[1,2,4]triazolo[1,5-a]pyrimidin-7-amine

EXAMPLE 118

6-(2-chloro-6-fluorophenyl)-5-(difluoromethoxy)-7-(4-methyl-1-piperidinyl)[1,2,4]triazolo[1,5-a]pyrimidine

EXAMPLE 119

5-chloro-6-(2-chloro-6-fluorophenyl)-7-[(4-chlorophenyl)sulfanyl][1,2,4]triazolo[1,5-a]pyrimidine

EXAMPLE 120

5-chloro-6-(2-chloro-6-fluorophenyl)-7-[(2-methoxyphenyl)sulfanyl][1,2,4]triazolo[1,5-a]pyrimidine

EXAMPLE 121

5-chloro-6-(2-chloro-6-fluorophenyl)-N-(1,2,2-trimethylpropyl)[1,2,4]triazolo[1,5-a]pyrimidin-7-amine

EXAMPLE 122

5-chloro-6-(2,3,4,5,6-pentafluorophenyl)-N-(1,2,2-trimethylpropyl)[1,2,4]triazolo[1,5-a]pyrimidin-7-amine

EXAMPLE 123

5-chloro-6-(2,4,6-trifluorophenyl)-N-(1,2,2-trimethylpropyl)[1,2,4]triazolo[1,5-a]pyrimidin-7-amine

EXAMPLE 124

5-chloro-6-(4-fluorophenyl)-N-(1,2,2-trimethylpropyl)[1,2,4]triazolo[1,5-a]pyrimidin-7-amine

EXAMPLE 125

5,7-bis(4-methyl-1-piperidinyl)-6-(2,4,6-trifluorophenyl)[1,2,4]triazolo[1,5-a]pyrimidine

EXAMPLE 126

5-chloro-6-(2-methylphenyl)-N-(1,2,2-trimethylpropyl)[1,2,4]triazolo[1,5-a]pyrimidin-7-amine

EXAMPLE 127

5-chloro-6-(2,4,5-trifluorophenyl)-N-(1,2,2-trimethylpropyl)[1,2,4]triazolo[1,5-a]pyrimidin-7-amine

EXAMPLE 128

6-(2-bromophenyl)-5-chloro-N-(1,2,2-trimethylpropyl)[1,2,4]triazolo[1,5-a]pyrimidin-7-amine

EXAMPLE 129

5-chloro-N-isobutyl-N-(2,2,2-trifluoroethyl)-6-(2,4,6-trifluorophenyl)[1,2,4]triazolo[1,5-a]pyrimidin-7-amine

EXAMPLE 130

5-chloro-N-isobutyl-6-(2-methylphenyl)-N-(2,2,2-trifluoroethyl)[1,2,4]triazolo[1,5-a]pyrimidin-7-amine

EXAMPLE 131

5-chloro-6-(2-chloro-6-fluorophenyl)-N-(2,2,2-trifluoro-1-methylethyl)[1,2,4]triazolo[1,5-a]pyrimidin-7-amine

EXAMPLE 132

5-chloro-6-(2,6-difluorophenyl)-N-(2,2,2-trifluoro-1-methylethyl)[1,2,4]triazolo[1,5-a]pyrimidin-7-amine

EXAMPLE 133

5-chloro-N-(2,2,2-trifluoro-1-methylethyl)-6-(2,4,6-trifluorophenyl)[1,2,4]triazolo[1,5-a]pyrimidin-7-amine

EXAMPLE 134

N-allyl-5-chloro-N-isobutyl-6-(2,4,6-trifluorophenyl)[1,2,4]triazolo[1,5-a]pyrimidin-7-amine

EXAMPLE 135

5-chloro-N-(1,2-dimethylpropyl)-6-(2,4,6-trifluorophenyl)[1,2,4]triazolo[1,5-a]pyrimidin-7-amine

EXAMPLE 136

5-chloro-N-isopropyl-N-methyl-6-(2,4,6-trifluorophenyl)[1,2,4]triazolo[1,5-a]pyrimidin-7-amine

EXAMPLE 137

5-chloro-N-isopropyl-N-(2,2,2-trifluoroethyl)-6-(2,4,6-trifluorophenyl)[1,2,4]triazolo[1,5-a]pyrimidin-7-amine

EXAMPLE 138

7-butyl-5-chloro-6-(2,4,6-trifluorophenyl)[1,2,4]triazolo[1,5-a]pyrimidine

EXAMPLE 139

5-chloro-N-(1-phenylethyl)-6-(2,4,6-trifluorophenyl)[1,2,4]triazolo[1,5-a]pyrimidin-7-amine

EXAMPLE 140

5-chloro-6-(2-chlorophenyl)-N-(2,2,2-trifluoro-1-methylethyl)[1,2,4]triazolo[1,5-a]pyrimidin-7-amine

EXAMPLE 141

5-chloro-N-ethyl-N-isobutyl-6-(2,4,6-trifluorophenyl)[1,2,4]triazolo[1,5-a]pyrimidin-7-amine

EXAMPLE 142

5-chloro-6-(2-chloro-6-fluorophenyl)-7-hexyl[1,2,4]triazolo[1,5-a]pyrimidine

EXAMPLE 143

5-chloro-6-(2-methylphenyl)-N,N-bis(2,2,2-trifluoroethyl)[1,2,4]triazolo[1,5-a]pyrimidin-7-amine

EXAMPLE 144

5-chloro-N-cyclopentyl-N-methyl-6-(2,3,4,5,6-pentafluorophenyl)[1,2,4]triazolo[1,5-a]pyrimidin-7-amine

EXAMPLE 145

7-butyl-5-chloro-6-(2,6-difluorophenyl)[1,2,4]triazolo[1,5-a]pyrimidine

EXAMPLE 146

5-chloro-N-(1,2-dimethylpropyl)-N-methyl-6-(2,3,4,5,6-pentafluorophenyl)[1,2,4]triazolo[1,5-a]pyrimidin-7-amine

EXAMPLE 147

5-chloro-6-(2-chloro-6-fluorophenyl)-7-phenyl[1,2,4]triazolo[1,5-a]pyrimidine

EXAMPLE 148

5-chloro-6-(2-chloro-6-fluorophenyl)-7-(2-methylpropanyl)[1,2,4]triazolo[1,5-a]pyrimidine

EXAMPLE 149

5-chloro-6-(2-chloro-6-fluorophenyl)-7-pentyl[1,2,4]triazolo[1,5-a]pyrimidine

EXAMPLE 150

5-chloro-N-(1,2-dimethylpropyl)-N-methyl-6-(2,4,6-trifluorophenyl)[1,2,4]triazolo[1,5-a]pyrimidin-7-amine

EXAMPLE 151

5-chloro-6-(2-chloro-6-fluorophenyl)-7-cyclohexyl[1,2,4]triazolo[1,5-a]pyrimidine

EXAMPLE 152

5-chloro-6-(2-bromo-5-chlorophenyl)-N-(2,2,2-trifluoro-1-methylethyl)[1,2,4]triazolo[1,5-a]pyrimidin-7-amine

EXAMPLE 153

5-chloro-6-(2-chloro-6-fluorophenyl)-7-(3,3,3-trifluoropropyl)[1,2,4]triazolo[1,5-a]pyrimidine

EXAMPLE 154

5-chloro-6-(2-chloro-6-fluorophenyl)-7-(3-methylphenyl)[1,2,4]triazolo[1,5-a]pyrimidine

EXAMPLE 155

[5-chloro-6-(2,4,6-trifluorophenyl)-[1,2,4]triazolo[1,5-a]pyrimidin-7-yl]-(1-p-tolyl-ethyl)-amine

EXAMPLE 156

5-chloro-6-(2,4,6-trifluoro-phenyl)-7-cyclohexyl[1,2,4]triazolo[1,5-a]pyrimidine

EXAMPLE 157

5-chloro-7-cyclohexyl-6-(2,3,4,5,6-pentafluorophenyl)[1,2,4]triazolo[1,5-a]pyrimidine

EXAMPLE 158

5-chloro-6-(2-chloro-6-fluorophenyl)-7-(4,4-difluoro-1-piperidinyl)[1,2,4]triazolo[1,5-a]pyrimidine

EXAMPLE 159

7-(bicyclo[2.2.1]hept-2-ylamino)-5-chloro-6-{2-fluoro-4-nitrophenyl}[1,2,4]triazolo[1,5-a]pyrimidine

EXAMPLE 160

5-chloro-6-{2-fluoro-4-nitrophenyl}-7-(4-methyl-1-piperidinyl)[1,2,4]triazolo[1,5-a]pyrimidine

EXAMPLE 161

5-(methylsulfanyl)-6-(2-chloro-6-fluorophenyl)-7-cyclohexyl[1,2,4]triazolo[1,5-a]pyrimidine

EXAMPLE 162

[5-chloro-6-(2,4,6-trifluorophenyl)[1,2,4]triazolo[1,5-a]pyrimidin-7-yl](2,2,2-trifluoro-1-phenylethyl)-amine

EXAMPLE 163

5-chloro-N-[1-(trifluoromethyl)propyl]-6-(2,4,6-trifluorophenyl)[1,2,4]triazolo[1,5-a]pyrimidin-7-amine

EXAMPLE 164

5-bromo-6-(2-chloro-6-fluorophenyl)-7-cyclohexyl[1,2,4]triazolo[1,5-a]pyrimidine

EXAMPLE 165

6-(2-chloro-6-fluorophenyl)-7-cyclohexyl[1,2,4]triazolo[1,5-a]pyrimidin-5-amine

EXAMPLE 166

[5-chloro-6-(2,4,6-trifluorophenyl)[1,2,4]triazolo[1,5-a]pyrimidin-7-yl]-(2-methyl-1-trifluoromethyl-propyl)amine

EXAMPLE 167

5-chloro-7-(3-cyclohexen-1-yl)-6-(2,4,6-trifluorophenyl)[1,2,4]triazolo[1,5-a]pyrimidine

EXAMPLE 168

5-chloro-7-(1-cyclohexen-1-yl)-6-(2,4,6-trifluorophenyl)[1,2,4]triazolo[1,5-a]pyrimidine

EXAMPLE 169

5-chloro-N-[(1R)-2,2,2-trifluoro-1-methylethyl]-6-(2,4,6-trifluorophenyl)[1,2,4]triazolo[1,5-a]pyrimidin-7-amine

EXAMPLE 170

5-chloro-N-[(1S)-2,2,2-trifluoro-1-methylethyl]-6-(2,4,6-trifluorophenyl)[1,2,4]triazolo[1,5-a]pyrimidin-7-amine

EXAMPLE 171

6-(2,4-difluorophenyl)-5-chloro-N-(2,2,2-trifluoro-1-methylethyl)[1,2,4]triazolo[1,5-a]pyrimidin-7-amine

EXAMPLE 172

5-chloro-6-(2,6-difluoro-4-methoxyphenyl)-7-(4-methyl-1-piperidinyl)[1,2,4]triazolo[1,5-a]pyrimidine

EXAMPLE 173

5-chloro-6-(2,6-difluoro-4-methoxyphenyl)-N-(2,2,2-trifluoro-1-methylethyl)[1,2,4]triazolo[1,5-a]pyrimidin-7-amine

EXAMPLE 174

5-chloro-7-cyclohexyl-6-(2,6-difluoro-4-methoxyphenyl)[1,2,4]triazolo[1,5-a]pyrimidine

EXAMPLE 175

5-chloro-6-(2,6-difluoro-4-methoxyphenyl)-N-[(1S)-2,2,2-trifluoro-1-methylethyl][1,2,4]triazolo[1,5-a]pyrimidin-7-amine

EXAMPLE 176

7-cyclohexyl-6-(2,6-difluoro-4-methoxyphenyl)-5-methoxy[1,2,4]triazolo[1,5-a]pyrimidine

EXAMPLE 177

5-chloro-7-(4-fluorocyclohexyl)-6-(2,4,6-trifluorophenyl)[1,2,4]triazolo[1,5-a]pyrimidine

EXAMPLE 178

5-chloro-6-(2,6-dichloro-4-fluorophenyl)-7-(3,3,3-trifluoropropyl)[1,2,4]triazolo[1,5-a]pyrimidin-7-amine

EXAMPLE 179

N-(sec-butyl)-5-chloro-6-(2,6-dichloro-4-fluorophenyl)[1,2,4]triazolo[1,5-a]pyrimidin-7-amine

EXAMPLE 180

4-{5-chloro-7-[(2,2,2-trifluoro-1-methylethyl)amino][1,2,4]triazolo[1,5-a]pyrimidin-6-yl}-3,6-difluorophenol

EXAMPLE 181

5-chloro-7-(3-cyclohexen-1-yl)-6-(2,6-difluoro-4-methoxyphenyl)[1,2,4]triazolo[1,5-a]pyrimidine

EXAMPLE 182

5-chloro-6-(2,6-difluoro-4-methoxyphenyl)[1,2,4]triazolo[1,5-a]pyrimidin-7-amine

EXAMPLE 183

5-chloro-N-cyclopentyl-6-(2,6-difluoro-4-methoxyphenyl)[1,2,4]triazolo[1,5-a]pyrimidin-7-amine

EXAMPLE 184

5-chloro-6-(2,6-difluoro-4-methoxyphenyl)-7-(3,6-dihydro-1(2H)-pyridinyl)[1,2,4]triazolo[1,5-a]pyrimidine

EXAMPLE 185

5-chloro-6-(2,6-difluoro-4-methoxyphenyl)-7-(4-thiomorpholinyl)[1,2,4]triazolo[1,5-a]pyrimidine

EXAMPLE 186

7-(1-azepanyl)-5-chloro-6-(2,6-difluoro-4-methoxyphenyl)[1,2,4]triazolo[1,5-a]pyrimidine

EXAMPLE 187

5-chloro-6-(2,6-difluoro-4-methoxyphenyl)-N-(1,2,2-trimethylpropyl)[1,2,4]triazolo[1,5-a]pyrimidin-7-amine

EXAMPLE 188

5-chloro-6-(2,6-difluoro-4-methoxyphenyl)-N-ethyl-N-(2-methyl-2-propenyl)[1,2,4]triazolo[1,5-a]pyrimidin-7-amine

EXAMPLE 189

5-chloro-6-(2,6-difluoro-4-methoxyphenyl)-7-(4-fluorocyclohexyl)[1,2,4]triazolo[1,5-a]pyrimidine

EXAMPLE 190

6-(4-{5-chloro-7-[(2,2,2-trifluoro-1-methylethyl)amino][1,2,4]triazolo[1,5-a]pyrimidin-6-yl}-3,5-difluorophenoxy)hexanoic acid

EXAMPLE 191

2,6-difluoro-4-(2-fluoroethoxy)phenyl]-N-(2,2,2-trifluoro-1-methylethyl)[1,2,4]triazolo[1,5-a]pyrimidin-7-amine

EXAMPLE 192

5-chloro-N-isopropyl-6-{2-[(trifluoromethyl)sulfanyl]phenyl}[1,2,4]triazolo[1,5-a]pyrimidin-7-amine

EXAMPLE 193

5-chloro-N-[4-(trifluoromethyl)phenyl]-6-(2,4,6-trifluorophenyl)[1,2,4]triazolo[1,5-a]pyrimidin-7-amine

EXAMPLE 194

5-chloro-N-(4,4,4-trifluoro-2-methylbutyl)-6-(2,4,6-trifluorophenyl)[1,2,4]triazolo[1,5-a]pyrimidin-7-amine

EXAMPLE 195

5-chloro-6-(2,6-difluoro-4-methoxyphenyl)-7-(3-methyl-3-butenyl)[1,2,4]triazolo[1,5-a]pyrimidine

EXAMPLE 196

5-chloro-6-(2,6-difluoro-4-methoxyphenyl)-7-isobutyl[1,2,4]triazolo[1,5-a]pyrimidine

EXAMPLE 197

7-cyclopentyl-6-(2,6-difluoro-4-methoxyphenyl)-5-methoxy[1,2,4]triazolo[1,5-a]pyrimidine

EXAMPLE 198

5-chloro-6-(2-thienyl)-N-[(1R)-2,2,2-trifluoro-1-methylethyl[1,2,4]triazolo[1,5-a]pyrimidin-7-amine

EXAMPLE 199

4-(5-chloro-7-(2,2,2-trifluoro-1-methyl-ethylamino)[1,2,4]triazolo[1,5-a]pyrimidin-6-yl]-3,5-difluoro-phenol

EXAMPLE 200

{5-chloro-6-[2,6-difluoro-4-(2,2,2-trifluoro-ethoxy)-phenyl]-[1,2,4]triazolo[1,5-a]pyrimidin-7-yl}-(2,2,2-trifluoro-1-methyl-ethyl)amine

EXAMPLE 201

5-chloro-6-{2,6-difluoro-4-(methoxyphenyl)-N-(2,2,2-trifluoro-1-methylethyl)[1,2,4]triazolo[1,5-a]pyrimidin-7-amine

EXAMPLE 202

(5-chloro-6-{4-[2-(2-ethoxyethoxy]-ethoxy]-2,6-difluoro-phenyl}[1,2,4]triazolo[1,5-a]pyrimidin-7-yl-)-(2,2,2-trifluoro-1-methylethyl)amine

EXAMPLE 203

(5-chloro-6-{2,6-difluoro-4-[2-(2-methoxy-ethoxy)ethoxy]-phenyl}-[1,2,4]triazolo[1,5-a]pyrimidin-7-yl-)-(2,2,2-trifluoro-1-methylethyl)amine

EXAMPLE 204

5-chloro-6-[2,6-difluoro-4-(3-furan-3-ylmethoxy)phenyl[1,2,4]triazolo[1,5-a]pyrimidin-7-yl]-N-(2,2,2-trifluoro-1-methylethyl)amine

EXAMPLE 205

5-chloro-6-(2,5-difluoro-4-methoxyphenyl)-N-(1,2,2-trimethylpropyl)[1,2,4]triazolo[1,5-a]pyrimidin-7-amine

EXAMPLE 206

7-cyclohexyl-6-[2,6-difluoro-4-(2-methoxyethoxy)phenyl]-5-methoxy[1,2,4]triazolo[1,5-a]pyrimidine

EXAMPLE 207

5-chloro-6-(2-fluoro-4-methoxy-6-chlorophenyl)-N-(2,2,2-trifluoro-1-methylethyl)[1,2,4]triazolo[1,5-a]pyrimidin-7-amine

EXAMPLE 208

5-chloro-6-[2,6-difluoro-4-(2-fluoroethoxy)phenyl]-N-ethyl-N-(2-methyl-2-propenyl)[1,2,4]triazolo[1,5-a]pyrimidin-7-amine

EXAMPLE 209

2-[2-(4-{5-chloro-7-[(2,2,2-trifluoro-1-methylethyl)amino][1,2,4]triazolo[1,5-a]pyrimidin-6-yl}-3,5-difluorophenoxy)ethoxy]ethanol

EXAMPLE 210

5-chloro-6-(2,3-difluoro-4-methoxyphenyl)-N-(2,2,2-trifluoro-1-methylethyl)[1,2,4]triazolo[1,5-a]pyrimidin-7-amine

EXAMPLE 211

5-chloro-6-{4-(2-fluoroethoxy)-2,6-difluorphenyl}-N-(2,2,2-trifluoro-1-methylethyl)[1,2,4]triazolo[1,5-a]pyrimidin-7-amine

EXAMPLE 212

5-chloro-N-(4-chlorobenzyl)-6-(2-chloro-6-fluorophenyl)[1,2,4]triazolo[1,5-a]pyrimidin-7-amine

EXAMPLE 213

5-chloro-6-(2-chloro-6-fluorophenyl)-7-[4-(2-pyridinyl)-1-piperazinyl][1,2,4]triazolo[1,5-a]pyrimidine

EXAMPLE 214

5-chloro-6-(2-chloro-6-fluorophenyl)-N-(1-ethylpentyl)[1,2,4]triazolo[1,5-a]pyrimidin-7-amine

EXAMPLE 215

5-chloro-6-(2-chloro-6-fluorophenyl)-7-[4-(2-chlorophenyl)-1-piperazinyl][1,2,4]triazolo[1,5-a]pyrimidine

EXAMPLE 216

5-chloro-6-(2-chloro-6-fluorophenyl)-7-[4-(4-methoxyphenyl)-3-methyl-1-piperazinyl][1,2,4]triazolo[1,5-a]pyrimidine

EXAMPLE 217

5-chloro-N-cyclopentyl-6-(2-chloro-6-fluorophenyl)[1,2,4]triazolo[1,5-a]pyrimidin-7-amine

EXAMPLE 218

5-chloro-7-phenoxy-6-(4-methoxy-phenyl)[1,2,4]triazolo[1,5-a]pyrimidine

EXAMPLE 219

5-chloro-N-cyclopentyl-6-(4-methylphenyl)[1,2,4]triazolo[1,5-a]pyrimidin-7-amine

EXAMPLE 220

5,7-diphenoxy-6-(4-methoxyphenyl)[1,2,4]triazolo[1,5-a]pyrimidine

EXAMPLE 221

5-chloro-N-cyclopentyl-6-(2-chlorophenyl)[1,2,4]triazolo[1,5-a]pyrimidin-7-amine

EXAMPLE 222

5-chloro-N,N-diethyl-6-[4-methoxyphenyl][1,2,4]triazolo[1,5-a]pyrimidin-7-amine

EXAMPLE 223

5-chloro-N,N-diethyl-6-[2,4-dichlorophenyl][1,2,4]triazolo[1,5-a]pyrimidin-7-amine

EXAMPLE 224

N-bicyclo[2.2.1]hept-2-yl-5-chloro-6-(2,4-dichlorophenyl)[1,2,4]triazolo[1,5-a]pyrimidin-7-amine

EXAMPLE 225

5-chloro-6-(2-chloro-6-fluorophenyl)-7-(1,4-dioxa-8-azaspiro[4.5]dec-8-yl)[1,2,4]triazolo[1,5-a]pyrimidine

EXAMPLE 226

5-cyano-7-(4-methyl-1-piperidinyl)-6-(2-chloro-5-fluorophenyl)[1,2,4]triazolo[1,5-a]pyrimidine

EXAMPLE 227

5-(methylsulfanyl)-7-(4-methyl-1-piperidinyl)-6-(2-chloro-6-fluorophenyl)[1,2,4]triazolo[1,5-a]pyrimidine

EXAMPLE 228

5-(methylsulfanyl)-7-(4-methyl-1-piperidinyl)-6-(2-chloro-5-(methylsulfanyl)phenyl)[1,2,4]triazolo[1,5-a]pyrimidine

EXAMPLE 229

5-chloro-7-(1,4-dioxa-8-azaspiro[4,5]dec-8-yl)-6-(4-methoxyphenyl)[2,4]triazolo[1,5-a]pyrimidine

EXAMPLE 230

5-chloro-N-ethyl-N-(2-methyl-2-propenyl)-6-(4-(methylsulfanyl)phenyl[1,2,4]triazolo[1,5-a]pyrimidin-7-amine

EXAMPLE 231

2-methyl-6,7-di-(4-methoxyphenyl)[1,2,4]triazolo[1,5-a]pyrimidine

EXAMPLE 232

2-methyl-6-phenyl-7-(4-chlorophenyl)[1,2,4]triazolo[1,5-a]pyrimidine

EXAMPLE 233

2-trifluoromethyl-6-phenyl-7-(4-methoxyphenyl)[1,2,4]triazolo[1,5-a]pyrimidine

EXAMPLE 234

5,7-diphenoxy-6-(2-methylpropyl)[1,2,4]triazolo[1,5-a]pyrimidine

EXAMPLE 235

5-chloro-6-(3,4-difluorophenyl)-N-(isopropyl)[1,2,4]triazolo[1,5-a]pyrimidin-7-amine

EXAMPLE 236

5-bromo-6-(4-bromophenyl)-7-dimethylamino[1,2,4]triazolo[1,5-a]pyrimidine

EXAMPLE 237

5-bromo-6-(4-trifluoromethylphenyl)-7-dimethylamino[1,2,4]triazolo[1,5-a]pyrimidine

EXAMPLE 238

5-chloro-6-(3,4-difluorophenyl)-7-dimethylamino[1,2,4]triazolo[1,5-a]pyrimidine

EXAMPLE 239

5-chloro-6-(4-trifluoromethylphenyl)-N-(ethyl)[1,2,4]triazolo[1,5-a]pyrimidin-7-amine

EXAMPLE 240

7-(1-azepanyl)-5-chloro-6-(4-tert-butylphenyl)[1,2,4]triazolo[1,5-a]pyrimidine

EXAMPLE 241 ethyl {[5-chloro-6-(2-chloro-6-fluorophenyl)[1,2,4]triazolo[1,5-a]pyrimidin-7-yl]amino}acetate

EXAMPLE 242 diethyl 5-chloro-6-(2,6-difluorophenyl)[1,2,4]triazolo[1,5-a]pyrimidin-7-malonate

EXAMPLE 243

5-chloro-6-(2,5-difluorophenyl)-N-(3-methyl-2-butenyl)[1,2,4]triazolo[1,5-a]pyrimidin-7-amine

EXAMPLE 244

[5-chloro-6-(2-chloro-6-fluorophenyl)-[1,2,4]triazolo[1,5-a]pyrimidin-7-yl]acetic acid methyl ester

EXAMPLE 245

5-chloro-6-(2,6-difluorophenyl)-7-(2-ethyl-1H-imidazol-1-yl)[1,2,4]triazolo[1,5-a]pyrimidine

EXAMPLE 246

5-chloro-N,N-diethyl-6-[4-(methylsulfanyl)phenyl][1,2,4]triazolo[1,5-a]pyrimidin-7-amine

EXAMPLE 247 ethyl [6-(2-chloro-6-fluorophenyl)-7-(4-methyl-1-piperidinyl)-[1,2,4]triazolo[1,5-a]pyrimidin-5-yl]acetate

EXAMPLE 248

5-chloro-N-ethyl-N-(2-methyl-2-propenyl)-6-(4-phenoxyphenyl)[1,2,4]triazolo[1,5-a]pyrimidin-7-amine

EXAMPLE 249 dimethyl 2-[5-chloro-6-(2-chloro-6-fluorophenyl)[1,2,4]triazolo[1,5-a]pyrimidin-7-yl]malonate

EXAMPLE 250 diethyl 2-{[5-chloro-6-(2-chloro-6-fluorophenyl)[1,2,4]triazolo[1,5-a]pyrimidin-7-yl]oxy}-2-isobutyl-malonate

EXAMPLE 251

2-[5-chloro-6-(2-chloro-6-fluorophenyl)[1,2,4triazolo[1,5-a]pyrimidin-7-yl]-1,3-cyclohexanedione

EXAMPLE 252

2-[5-chloro-6-(2-chloro-6-fluorophenyl)[1,2,4]triazolo[1,5-a]pyrimidin-7-yl]cyclohexanone

EXAMPLE 253

5-chloro-7-(3-nitro-4-methylanilino)-6-(2,4,6-trifluorophenyl) [1,2,4]triazolo[1,5-a]pyrimidine

EXAMPLE 254

7-cyclohexyl-6-[2,6-difluoro-4-(2-methoxyethoxy)phenyl]5-(2-methoxyethoxy)[1,2,4]triazolo[1,5-a]pyrimidine

EXAMPLE 255

7-(3-bromophenyl)-2-ethyl-6-(4-methoxyphenyl)[1,2,4]triazolo[1,5-a]pyrimidine

EXAMPLE 256

7-(3-bromophenyl)-6-(3-chlorophenyl)-2-ethyl[1,2,4]triazolo[1,5-a]pyrimidine

EXAMPLE 257

7-(4-bromophenyl)-2-ethyl-6-[4-(trifluoromethyl)phenyl][1,2,4]triazolo[1,5-a]pyrimidine

EXAMPLE 258

5-chloro-6-(2-chloro-6-fluorophenyl)-N-(3,4,5-trimethoxybenzyl)[1,2,4]triazolo[1,5-a]pyrimidin-7-amine

EXAMPLE 259

7-(2-benzyl-4,5-dihydro-1H-imidazol-1-yl)-5-chloro-6-(2-chloro-6-fluorophenyl)[1,2,4]triazolo[1,5-a]pyrimidine

EXAMPLE 260

N-4-[5-chloro-6-(2-chloro-6-fluorophenyl)[1,2,4]triazolo[1,5-a]pyrimidin-7-yl-N,N-1-diethyl-1,4-pentanediamine

EXAMPLE 261

5-chloro-N-(3-methyl-2-butenyl)-6-phenyl[1,2,4]triazolo[1,5-a]pyrimidin-7-amine

EXAMPLE 262

5-dimethylamino-6-phenyl-N-cyclopentyl[1,2,4]triazolo[1,5-a]pyrimidin-7-amine

EXAMPLE 263

5-chloro-7-[(2-furylmethyl)sulfanyl]-6-(4-methoxyphenyl)[1,2,4]triazolo[1,5-a]pyrimidine

EXAMPLE 264

6-[1,1'-biphenyl]-4-yl-5-chloro-N-cyclopentyl[1,2,4]triazolo[1,5-a]pyrimidin-7-amine

EXAMPLE 265

6-[4-(benzyloxy)phenyl]-5-chloro-N-isopropyl[1,2,4]triazolo[1,5-a]pyrimidin-7-amine

EXAMPLE 266

5-chloro-N-[(2,2-dichlorocyclopropyl)methyl]-6-(3,4,5-trimethoxyphenyl)[1,2,4]triazolo[1,5-a]pyrimidin-7-amine

EXAMPLE 267

N-cyclopentyl-6-(2-fluorophenyl)-5-hydrazino[1,2,4]triazolo[1,5-a]pyrimidin-7-amine

EXAMPLE 268

5-chloro-N-ethyl-6-(2-methylphenyl)[1,2,4]triazolo[1,5-a]pyrimidin-7-amine

EXAMPLE 269

6-(4-tert-butylphenyl)-5-chloro-N-isopropyl[1,2,4]triazolo[1,5-a]pyrimidin-7-amine

EXAMPLE 270

5-chloro-6-[2,6-difluoro-4-[(3-methyl-2-butenyl)oxy]phenyl]-N-(2,2,2-trifluoro-1-methylethyl)-I[1,2,4]triazolo[1,5-a]pyrimidin-7-amine

EXAMPLE 271

5-chloro-6-[2,6-difluoro-4-(1-propenyloxy)phenyl]-N-(2,2,2-trifluoro-1-methylethyl)-I[1,2,4]triazolo[1,5-a]pyrimidin-7-amine

EXAMPLE 272

5-chloro-N-(3-tricyclo[2.2.1.0$^{2,6}$]hept-1-yl)-6-(2,4,6-trifluorophenyl)[1,2,4]triazolo[1,5-a]pyrimidin-7-amine

EXAMPLE 273

5-azido-7-cyclohexyl-6-(2-fluoro-6-chlorophenyl)[1,2,4]triazolo[1,5-a]pyrimidine

EXAMPLE 274

5-azido-6-[2-chloro-6-fluorophenyl]-7-(4-methyl-1-piperidinyl)[1,2,4]triazolo[1,5-a]pyrimidine

EXAMPLE 275

2,5-dichloro-7-(4-methyl-1-piperidinyl)-6-[2-chloro-6-fluorophenyl][1,2,4]triazolo[1,5-a]pyrimidine

We claim:
1. A method of treating or inhibiting the growth of cancerous tumor cells in a mammal in need thereof which comprises administering to said mammal an effective amount of a substituted triazolopyrimidine derivative selected from those of Formula I:

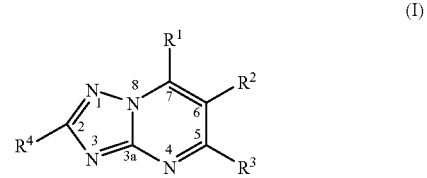

wherein:
$R^1$ is the moiety —$NR^aR^b$;
$R^a$ is H, alkyl of 1 to 12 carbon atoms, said alkyl being optionally substituted with 0 to 3 substituents independently selected from halogen, nitro, hydroxyl, alkyl, alkoxy, haloalkoxy, amino, alkylamino, dialkylamino, aryl, alkoxycarbonyl, carboxyl, alkanoyl, alkylthio, carbamoyl, alkylamido, phenyl, phenoxy, benzyl, benzyloxy, and cycloalkyl,
alkenyl of 2 to 12 carbon atoms, said alkenyl being optionally substituted with 0 to 3 substituents independently selected from halogen, nitro, cyano, hydroxyl, alkyl, alkoxy, amino, alkylamino, dialkylamino, aryl, alkoxycarbonyl, carboxyl, alkanoyl, carbamoyl, alkylamido, phenyl, phenoxy, benzyl, benzyloxy, and cycloalkyl,
cycloalkyl of 3 to 8 carbon atoms, said cycloalkyl being optionally substituted with 0 to 3 substituents independently selected from halogen, alkyl, amino, alkylamino and dialkylamino,
cycloalkenyl of 5 to 10 carbon atoms, said cycloalkenyl being optionally substituted with 0 to 3 substituents independently selected from halogen, alkyl, amino, alkylamino and dialkylamino,
bicycloalkyl of 5 to 10 carbon atoms, said bicycloalkyl being optionally substituted with 0 to 3 substituents independently selected from halogen, and alkyl, tricycloalkyl,
aryl of 6, 10 or 14 carbon atoms, heterocyclyl of 3 to 12 ring atoms, said heterocyclyl being optionally substituted with 0 to 3 substituents independently selected from halogen, hydroxyl, alkyl, alkoxy, amino, alkylamino, dialkylamino, phenyl, and cycloalkyl;
$R^b$ is H, alkyl of 1 to 12 carbon atoms, said alkyl being optionally substituted with 0 to 3 substituents independently selected from halogen, nitro, hydroxyl, alkyl, alkoxy, amino, alkylamino, dialkylamino, aryl, alkoxycarbonyl, carboxyl, alkanoyl, alkylthio, carbamoyl, alkylamido, phenyl, phenoxy, benzyl, heterocyclyl, and cycloalkyl, alkenyl of 2 to 12 carbon atoms, said alkenyl being optionally substituted with 0 to 3 substituents independently selected from halogen, nitro, cyano, hydroxyl, alkyl, alkoxy, amino, alkylamino, dialkylamino, formyl, aryl, alkoxycarbonyl, carboxyl, alkanoyl, carbamoyl, alkylamido, phenyl, phenoxy, benzyl, benzyloxy, heterocyclyl, and cycloalkyl, aryl of 6, 10 or 14 carbon atoms, said aryl being optionally substituted with 0 to 5 substituents independently selected from halogen, nitro, cyano, hydroxyl, alkyl, alkoxy, amino, alkylamino, dialkylamino, formyl, alkoxycarbonyl, carboxyl, alkanoyl, carbamoyl, alkylamido, phenyl, phenoxy, benzyl, heterocyclyl, and cycloalkyl, bicycloalkyl of 5 to 10 carbon atoms, said bicycloalkyl being optionally substituted with 0 to 3 substituents independently selected from halogen, nitro, alkyl, amino, alkylamino, and dialkylamino, cycloalkyl of 3 to 10 carbon atoms, said cycloalkyl being optionally substituted with 0 to 3 substituents independently selected from halogen, alkyl, alkoxy, amino, alkylamino, and dialkylamino, cycloalkenyl of 5 to 10 carbon atoms, said cycloalkenyl being optionally substituted with 0 to 3 substituents independently selected from halogen, alkyl, amino, alkylamino, and dialkylamino, —S-aryl of 6, 10 or 14 carbon atoms, —S-alkyl, —S-alkenyl, —SO$_2$aryl of 6, 10 or 14 carbon atoms;

$R^2$ is phenyl, said phenyl being optionally substituted with 0 to 5 substituents independently selected from halogen, nitro, cyano, alkenyl, thiocyanato, cyanato, hydroxyl, alkyl, haloalkyl, alkoxy, alkenyloxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, and benzyloxy;

$R^3$ is H, halogen, alkyl of 1 to 12 carbon atoms optionally substituted with 0 to 3 substituents selected from, halogen, nitro, cyano, hydroxyl, alkoxycarbonyl and amino, alkoxy of 1 to 12 carbon atoms, aryloxy, —NR$^c$R$^d$, aralkyloxy, alkylthio of 1 to 12 carbon atoms, heterocyclyl of 5 to 6 ring atoms, said heterocyclyl being optionally substituted with 0 to 3 substituents independently selected from halogen, hydroxyl, alkyl, alkoxy, amino, alkylamino, dialkylamino, alkylthio, carbamoyl, alkylamido, phenyl, phenoxy, benzyl, benzyloxy, cyano, amino, alkylamino of 1 to 12 carbon atoms, dialkylamino of 1 to 12 carbon atoms, or —N$_3$;

$R^c$ is H, alkyl of 1 to 12 carbon atoms, said alkyl being optionally substituted with 0 to 3 substituents independently selected from halogen, hydroxyl, alkyl, alkoxy, amino, alkylamino, dialkylamino, and alkoxycarbonyl, $R^d$ is H, alkyl of 1 to 12 carbon atoms, said alkyl being optionally substituted with 0 to 3 substituents independently selected from halogen, hydroxyl, alkyl, alkoxy, amino, alkylamino, dialkylamino, and alkoxycarbonyl;

$R^4$ is H, alkyl of 1 to 12 carbon atoms, said alkyl being optionally substituted with 0 to 3 substituents independently selected from halogen, nitro, cyano, hydroxyl, alkoxy optionally substituted with 0 to 3 substituents selected from halogen, nitro, cyano, hydroxyl, and amino, amino, alkylamino of 1 to 12 carbon atoms optionally substituted with 0 to 3 substituents selected from halogen, nitro, cyano, hydroxyl, and amino, and dialkylamino(1 to 12 carbon atoms) optionally substituted with 0 to 3 substituents selected from, halogen, nitro, cyano, hydroxyl, and amino, and halogen;

provided that when: a) $R^1$ is diethylamino, $R^3$ chloro, $R^4$ is hydrogen, $R^2$ is not 4-trifluoromethylphenyl, 3,4-dichlorophenyl, 4-chlorophenyl, or 3-chloro-4-methoxyphenyl; b) $R^1$ is diethylamino, $R^3$ is bromo, $R^4$ is hydrogen, $R^2$ not 4-trifluoromethylphenyl; c) $R^1$ is isopropylamino, $R^3$ is chloro, $R^4$ is hydrogen, $R^2$ is not 2-benzyloxyphenyl or 3,4,5-trimethoxyphenyl; d) $R^1$ is cyclopentylamino, $R^3$ is chloro, $R^4$ is hydrogen, $R^2$ is not 3,4,5-trimethoxyphenyl, or 2-stilbene; e) $R^1$ is 2-amino-bicyclo(2.2.1.)heptyl, $R^3$ is chloro, $R^4$ is hydrogen, $R^2$ is not 3,4,5-trimethoxyphenyl and f) $R^1$ is diethylamino, $R^3$ is chloro, $R^4$ is hydrogen, $R^2$ is not 4-trifluoromethylphenyl; or a pharmaceutically acceptable salt thereof.

2. The method according to claim 1 wherein $R^a$ is H, alkyl of 1 to 6 carbon atoms, said alkyl being optionally substituted with 0 to 3 substituents independently selected from halogen, nitro, cyano, hydroxyl, alkoxy, amino, alkylamino, dialkylamino, alkoxycarbonyl, carboxyl, alkanoyl, alkylthio, carbamoyl, alkylamido, phenyl, phenoxy, benzyl, and benzyloxy, alkenyl of 2 to 6 carbon atoms, said alkenyl being optionally substituted with 0 to 3 substituents independently selected from halogen, nitro, cyano, hydroxyl, alkoxy, amino, alkylamino, and dialkylamino, alkoxycarbonyl, carboxyl, alkanoyl, carbamoyl, alkylamido, phenyl, phenoxy, benzyl, and benzyloxy, cycloalkyl of 3 to 6 carbon atoms, said cycloalkyl being optionally substituted with 0 to 3 substituents independently selected from halogen, alkyl, amino, alkylamino, and dialkylamino, aryl of 6 carbon atoms, said aryl being optionally substituted with 0 to 5 substituents independently selected from halogen, nitro, cyano, alkenyl, hydroxyl, alkyl, haloalkyl, alkoxy, alkenyloxy, haloalkoxy, amino, alkylamino, dialkylamino, alkoxycarbonyl, carboxyl, alkanoyl, alkylthio, carbamoyl, alkylamido, phenyl, phenoxy, benzyl, benzyloxy, and cycloalkyl, heterocyclyl of 3 to 6 ring atoms, or benzyl, said benzyl being optionally substituted with 0 to 5 substituents independently selected from halogen, hydroxyl, alkyl, alkoxy, amino, alkylamino, dialkylamino, alkoxycarbonyl, carboxyl, alkanoyl, carbamoyl, alkylamido, phenyl, phenoxy, benzyl, benzyloxy, and cycloalkyl;

$R^b$ is H, alkyl of 1 to 6 carbon atoms, said alkyl being optionally substituted with 0 to 3 substituents independently selected from halogen, hydroxyl, alkyl, alkoxy, amino, alkylamino, dialkylamino, alkoxycarbonyl, carboxyl, alkanoyl, alkylthio, carbamoyl, alkylamido, phenyl, phenoxy, benzyl, and cycloalkyl, alkenyl of 2 to 6 carbon atoms, said alkenyl being optionally substituted with 0 to 3 substituents independently selected from halogen, nitro, cyano, hydroxyl, alkyl, alkoxy, amino, alkylamino, dialkylamino, alkoxycarbonyl, carboxyl, alkanoyl, carbamoyl, alkylamido, phenyl, phenoxy, benzyl, benzyloxy, heterocyclyl, and cycloalkyl, aryl of 6 carbon atoms, said aryl being optionally substituted with 0 to 5 substituents independently selected from halogen, nitro, cyano, hydroxyl, alkyl, alkoxy, alkenyloxy, amino, alkylamino, dialkylamino, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, and cycloalkyl, cycloalkyl of 3 to 6 carbon atoms, said cycloalkyl being optionally substituted with 0 to 3 substituents independently selected from halogen, alkyl, alkoxy, amino, alkylamino, and dialkylamino, —S-aryl of 6 or 10 carbon atoms, —S-alkyl of 1 to 6 carbon atoms, heterocyclyl of 3 to 6 ring atoms, said heterocyclyl being optionally substituted with 0 to 3 substituents independently selected from halogen, nitro, cyano, hydroxyl, alkyl, alkoxy, amino, alkylamino, dialkylamino, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, and cycloalkyl, or benzyl, said benzyl being optionally substituted with 0 to 5 substituents independently selected from halogen, nitro, cyano, alkenyl, hydroxyl, alkyl, alkoxy, alkenyloxy, amino, alkylamino, dialkylamino, alkoxycarbonyl, carboxyl, alkanoyl, alkylthio, alkylsulphinyl, alkylsulphonyl, carbamoyl, alkylamido, phenyl, phenoxy, benzyl, benzyloxy, heterocyclyl, and cycloalkyl.

3. The method according to claim 1 wherein $R^a$ or $R^b$ represents an optionally substituted alkyl moiety of 1 to 12 carbon atoms wherein said optionally substituted alkyl is represented by the moiety —C*H($R^e$)($R^f$) where $R^e$ and $R^f$ independently represent an alkyl group of 1 to 12 carbon atoms said alkyl being optionally substituted with 0-3 halogen atoms where C* represents the (R) or (S) isomer.

4. The method according to claim 1 wherein $R^3$ is halogen, alkyl of 1 to 6 carbon atoms, alkoxy of 1 to 6 carbon atoms, alkylthio of 1 to 6 carbon atoms, or —NR$^c$R$^d$; $R^c$ is H, optionally substituted alkyl of 1 to 6 carbon atoms, said alkyl being optionally substituted with 0 to 3 substituents independently selected from halogen, hydroxyl, alkyl, alkoxy, amino, alkylamino, dialkylamino, and alkoxycarbonyl, $R^d$ is H, alkyl of 1 to 6 carbon atoms, said alkyl being optionally substituted with 0 to 3 substituents independently selected from halogen, hydroxyl, alkyl, alkoxy, amino, alkylamino, dialkylamino, and alkoxycarbonyl.

5. The method according to claim 1 wherein $R^4$ is H, alkyl of 1 to 6 carbon atoms, said alkyl being optionally substituted with 0 to 3 substituents independently selected from halogen, nitro, cyano, hydroxyl, alkoxy optionally substituted with 0 to 3 substituents selected from halogen, nitro, cyano, hydroxyl, and amino, amino, alkylamino of 1 to 6 carbon atoms optionally substituted with 0 to 3 substituents selected from halogen, nitro, cyano, hydroxyl and amino, and dialkylamino of 1 to 6 carbon atoms optionally substituted with 0 to 3 substituents selected from halogen, nitro, cyano, hydroxyl and amino.

6. The method according to claim 1 wherein $R^3$ is halogen, alkoxy of 1 to 6 carbon atoms, alkylthio of 1 to 6 carbon atoms, alkylamino of 1 to 6 carbon atoms or dialkylamino of 1 to 6 carbon atoms.

7. The method according to claim 1 wherein $R^4$ is H, alkyl of 1 to 3 carbon atoms, said alkyl being optionally substituted with 0 to 3 substituents independently selected from halogen, nitro, cyano, hydroxyl, alkoxy, haloalkoxy, amino, alkylamino, and dialkylamino.

8. The method according to claim 1 wherein $R^3$ is halogen, alkoxy of 1 to 6 carbon atoms, cyano, haloalkoxy of 1 to 6 carbon atoms, alkylthio of 1 to 6 carbon atoms, or —NR$^c$R$^d$;

$R^c$ is H, amino, alkyl of 1 to 6 carbon atoms, said alkyl being optionally substituted with 0 to 3 substituents independently selected from halogen, alkyl, alkoxy, amino, alkylamino, dialkylamino, aryl, and alkoxycarbonyl;

$R^d$ is H, alkyl of 1 to 6 carbon atoms, said alkyl being optionally substituted with 0 to 3 substituents independently selected from halogen, alkyl, alkoxy, amino, alkylamino, dialkylamino, and alkoxycarbonyl.

9. The method according to claim 1 wherein $R^4$ is H.

10. The method according to claim 1 wherein $R^3$ is halogen, alkoxy of 1 to 6 carbon atoms, —NR$^c$R$^d$, haloalkoxy of 1 to 6 carbon atoms, alkylthio of 1 to 6 carbon atoms, cyano, or —N$_3$;

and $R^4$ is H.

11. The method according to claim 1 wherein $R^1$ is the moiety —NR$^a$R$^b$;

$R^2$ is selected from

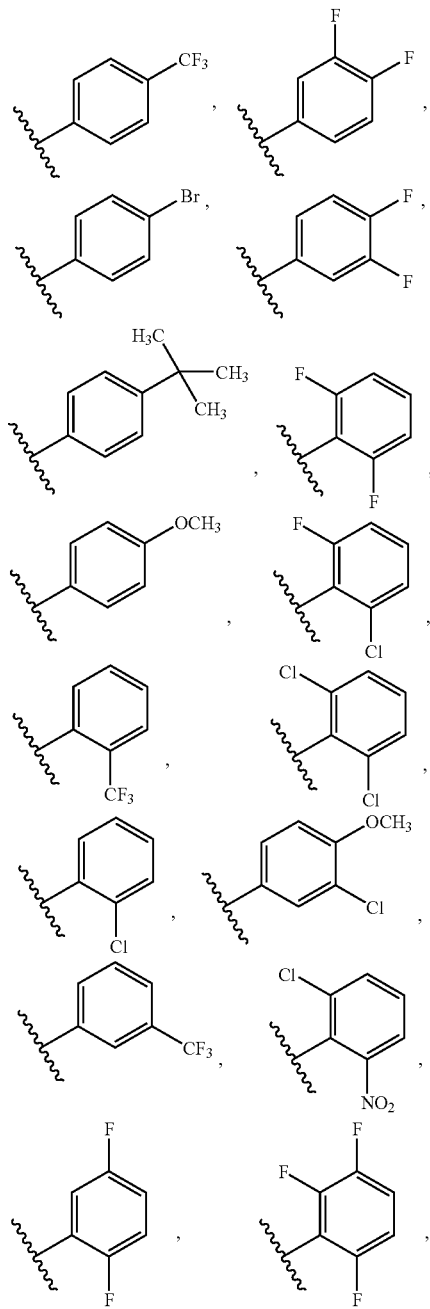

-continued
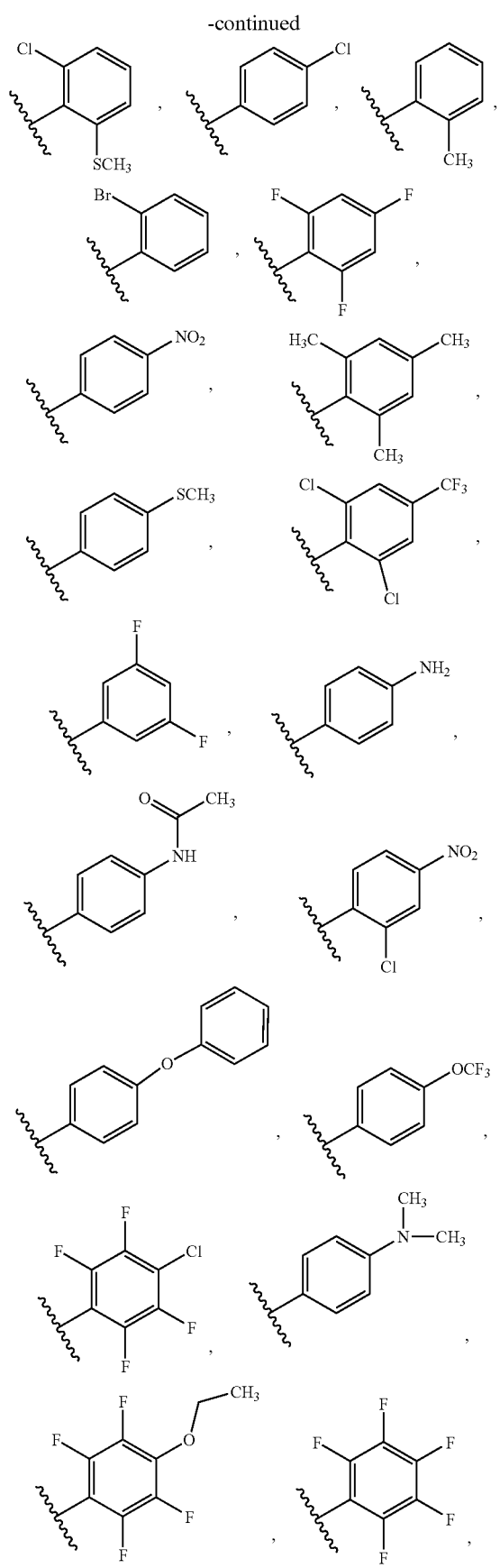
-continued
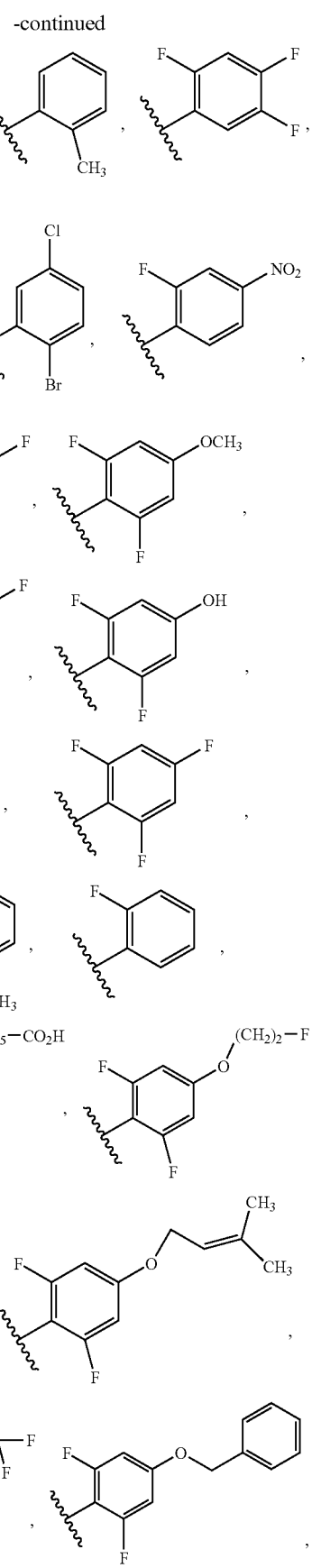

-continued
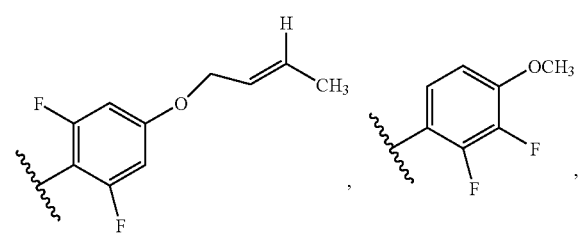
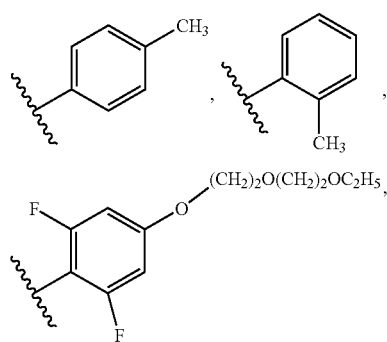
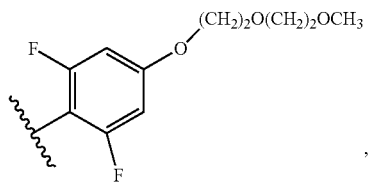
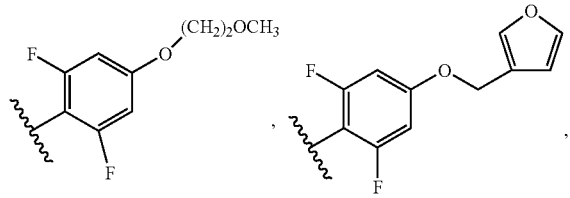
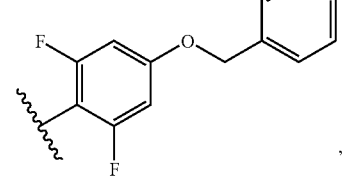
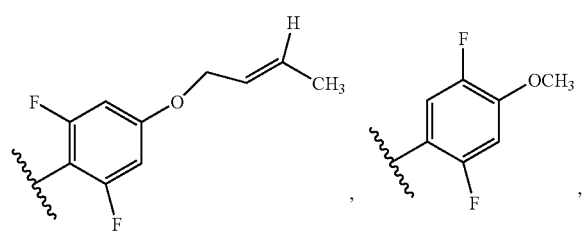
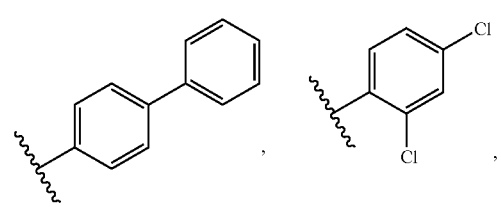
-continued
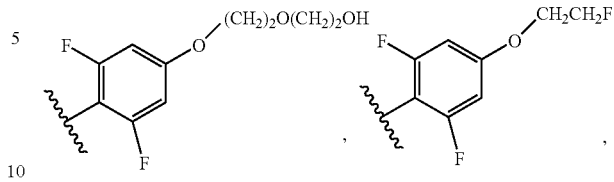
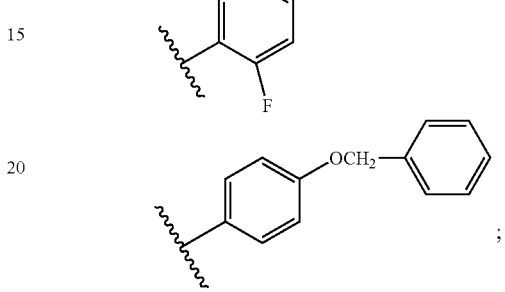
$R^3$ is H, halogen, alkoxy of 1 to 6 carbon atoms, $-NR^cR^d$, alkylthio of 1 to 6 carbon atoms or cyano;
$R^4$ is H or a pharmaceutically acceptable salt thereof.
12. The method according to claim 1 wherein R is selected from
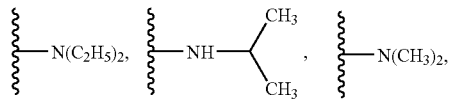
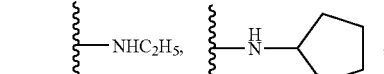
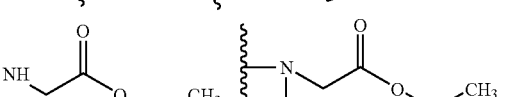
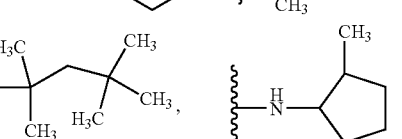
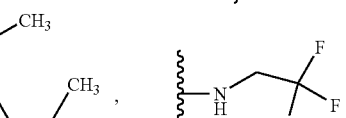
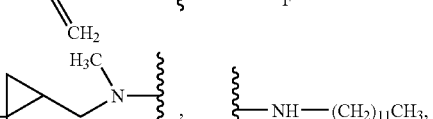
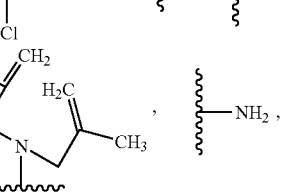

-continued

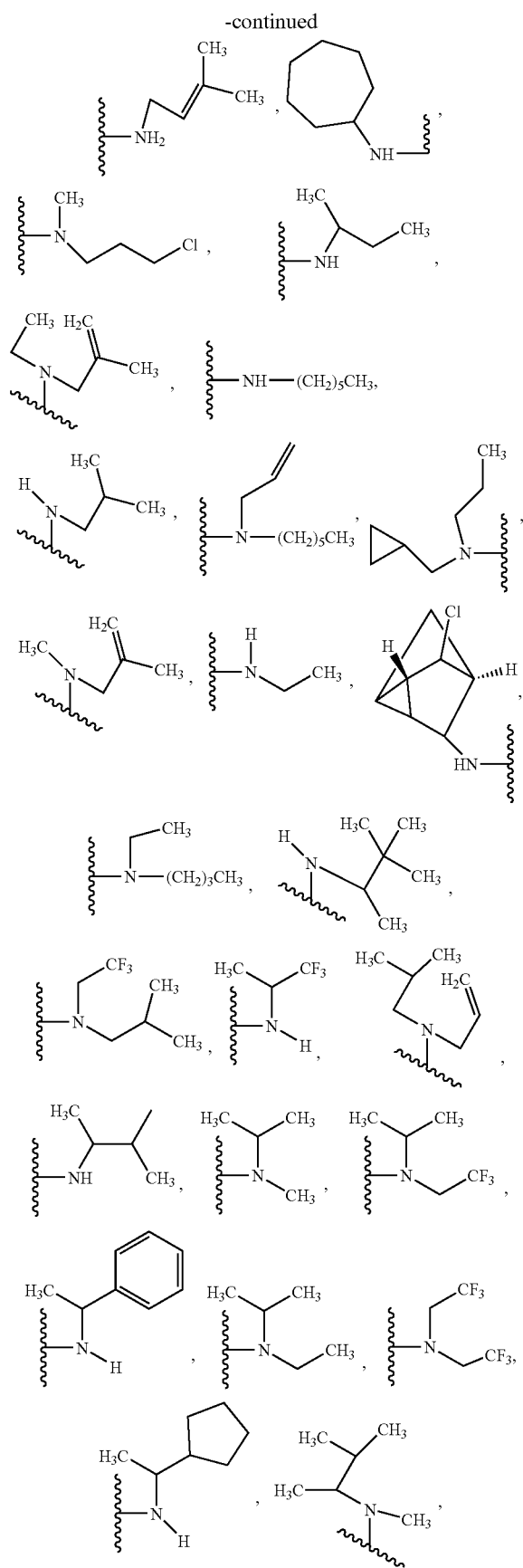

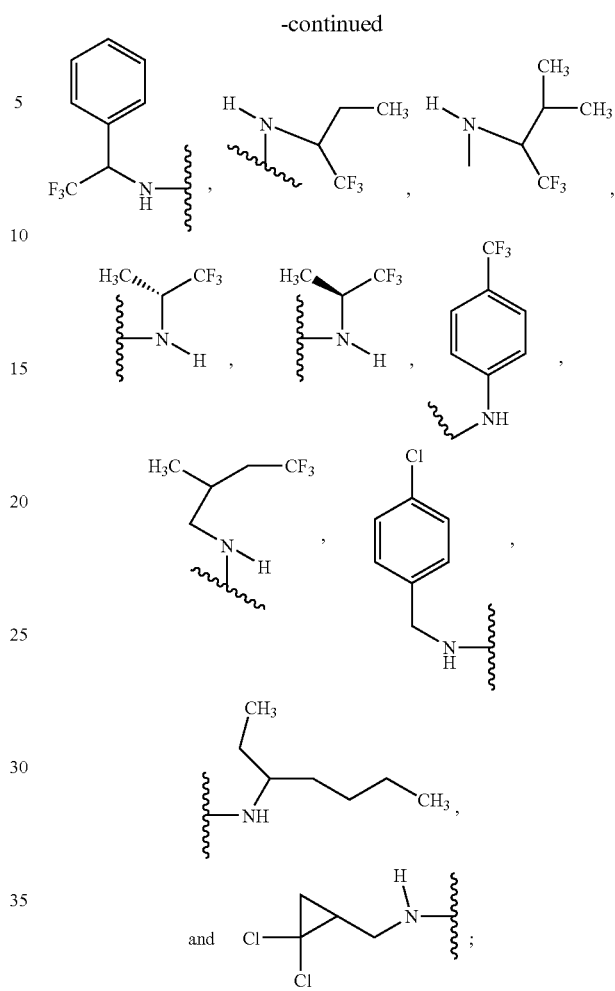

R³ is halogen, alkoxy of 1 to 6 carbon atoms, alkylthio of 1 to 6 carbon atoms or cyano;

R⁴ is H or a pharmaceutically acceptable salt thereof.

13. The method according to claim 1 wherein said substituted triazolopyrimidine derivative is selected from:

methyl [[5-chloro-6-(2-chloro-6-fluorophenyl)[1,2,4]triazolo[1,5-a]pyrimidin-7-yl](methyl)amino]acetate;

5-chloro-6-(2-chloro-6-fluorophenyl)-N-(1,1,3,3-tetramethylbutyl)[1,2,4]triazolo[1,5-a]pyrimidin-7-amine;

5-chloro-6-(2-chloro-6-fluorophenyl)-N-ethyl-N-(2-methyl-2-propenyl)[1,2,4]triazolo[1,5-a]pyrimidin-7-amine;

5-chloro-6-(2-chloro-6-fluorophenyl)-N-(2,2,2-trifluoroethyl)[1,2,4]triazolo[1,5-a]pyrimidin-7-amine;

5-chloro-6-(2-chloro-6-fluorophenyl)-N-[(2,2-dichlorocyclopropyl)methyl]-N-methyl[1,2,4]triazolo[1,5-a]pyrimidin-7-amine;

N-bicyclo[2.2.1]hept-2-yl-5-chloro-6-(3-chloro-4-methoxyphenyl)[1,2,4]triazolo[1,5-a]pyrimidin-7-amine;

5-chloro-6-(2,5-difluorophenyl)-N-dodecyl[1,2,4]triazolo[1,5-a]pyrimidin-7-amine;

N-[5-chloro-6-(2,3,6-trifluorophenyl)[1,2,4]triazolo[1,5-a]pyrimidin-7-yl]-N-isopropylamine 5-chloro-N-ethyl-N-(2-methyl-2-propenyl)-6-(2,3,6-trifluorophenyl)[1,2,4]triazolo[1,5-a]pyrimidin-7-amine;

N-allyl-5-chloro-6-(2-chloro-6-fluorophenyl)-N-(2-methyl-2-propenyl)[1,2,4]triazolo[1,5-a]pyrimidin-7-amine;

5-chloro-6-(2-chloro-6-fluorophenyl)[1,2,4]triazolo[1,5-a]pyrimidin-7-amine;
5-chloro-6-(3-chloro-4-methoxyphenyl)-N-cycloheptyl[1,2,4]triazolo[1,5-a]pyrimidin-7-amine;
5-chloro-N-(3-chloropropyl)-N-methyl-6-(2,3,6-trifluorophenyl)[1,2,4]triazolo[1,5-a]pyrimidin-7-amine;
6-(2-bromophenyl)-N-(sec-butyl)-5-chloro[1,2,4]triazolo[1,5-a]pyrimidin-7-amine;
5-chloro-N-ethyl-6-(4-methoxyphenyl)-N-(2-methyl-2-propenyl)[1,2,4]triazolo[1,5-a]pyrimidin-7-amine;
5-chloro-N-ethyl-N-(2-methyl-2-propenyl)-6-(2,4,6-trifluorophenyl)[1,2,4]triazolo[1,5-a]pyrimidin-7-amine;
5-chloro-N-isopropyl-6-(2,4,6-trifluorophenyl)[1,2,4]triazolo[1,5-a]pyrimidin-7-amine;
5-chloro-7-[ethyl(2-methyl-2-propenyl)amino]-6-{4-nitrophenyl}[1,2,4]triazolo[1,5a]pyrimidine;
N-bicyclo[2.2.1]hept-2-yl-5-chloro-6-(2,4,6-trifluorophenyl)[1,2,4]triazolo[1,5-a]pyrimidin-7-amine;
5-chloro-6-(2,6-difluorophenyl)-N-(2,2,2-trifluoroethyl)[1,2,4]triazolo[1,5-a]pyrimidin-7-amine;
5-chloro-6-(2-chlorophenyl)-N-(2,2,2-trifluoroethyl)[1,2,4]triazolo[1,5-a]pyrimidin-7-amine;
5-chloro-N-ethyl-6-mesityl-N-(2-methyl-2-propenyl)[1,2,4]triazolo[1,5-a]pyrimidin-7-amine;
5-chloro-N-ethyl-6-(2-methoxyphenyl)-N-(2-methyl-2-propenyl)[1,2,4]triazolo[1,5-a]pyrimidin-7-amine;
5-chloro-6-(2-chloro-6-fluorophenyl)-N-hexyl[1,2,4]triazolo[1,5-a]pyrimidin-7-amine;
5-chloro-N-ethyl-N-(2-methyl-2-propenyl)-6-[4-(methylsulfanyl)phenyl][1,2,4]triazolo[1,5-a]pyrimidin-7-amine;
N-(sec-butyl)-5-chloro-6-[4-(methylsulfanyl)phenyl][1,2,4]triazolo[1,5-a]pyrimidin-7-amine;
5-chloro-6-[2,6-dichloro-4-(trifluoromethyl)phenyl]-N-ethyl-N-(2-methyl-2-propenyl)[1,2,4]triazolo[1,5-a]pyrimidin-7-amine;
N-allyl-5-chloro-6-(2-chloro-6-fluorophenyl)-N-hexyl[1,2,4]triazolo[1,5-a]pyrimidin-7-amine;
5-chloro-6-(2-chloro-6-fluorophenyl)-N-(cyclopropylmethyl)-N-propyl[1,2,4]triazolo[1,5-a]pyrimidin-7-amine;
5-chloro-6-(4-chloro-2,3,5,6-tetrafluorophenyl)-N-cyclopentyl[1,2,4]triazolo[1,5-a]pyrimidin-7-amine;
5-chloro-6-{2-chloro-4-nitrophenyl}-7-[ethyl(2-methyl-2-propenyl)amino][1,2,4]triazolo[1,5-a]pyrimidine;
5-chloro-N-cyclopentyl-6-(4-ethoxy-2,3,5,6-tetrafluorophenyl)[1,2,4]triazolo[1,5-a]pyrimidin-7-amine;
5-chloro-N-methyl-N-(2-methyl-2-propenyl)-6-(2,4,6-trifluorophenyl)[1,2,4]triazolo[1,5-a]pyrimidin-7-amine;
6-(2-chloro-6-fluorophenyl)-N-ethyl-5-methyl[1,2,4]triazolo[1,5-a]pyrimidin-7-amine;
N-butyl-5-chloro-N-ethyl-6-(2,3,4,5,6-pentafluorophenyl)[1,2,4]triazolo[1,5-a]pyrimidin-7-amine;
5-chloro-6-(2-chloro-6-fluorophenyl)-N-(1,2,2-trimethylpropyl)[1,2,4]triazolo[1,5-a]pyrimidin-7-amine;
5-chloro-6-(2,3,4,5,6-pentafluorophenyl)-N-(1,2,2-trimethylpropyl)[1,2,4]triazolo[1,5-a]pyrimidin-7-amine;
5-chloro-6-(2,4,6-trifluorophenyl)-N-(1,2,2-trimethylpropyl)[1,2,4]triazolo[1,5-a]pyrimidin-7-amine;
5-chloro-6-(4-fluorophenyl)-N-(1,2,2-trimethylpropyl)[1,2,4]triazolo[1,5-a]pyrimidin-7-amine;
5-chloro-6-(2-methylphenyl)-N-(1,2,2-trimethylpropyl)[1,2,4]triazolo[1,5-a]pyrimidin-7-amine;
5-chloro-6-(2,4,5-trifluorophenyl)-N-(1,2,2-trimethylpropyl)[1,2,4]triazolo[1,5-a]pyrimidin-7-amine;
6-(2-bromophenyl)-5-chloro-N-(1,2,2-trimethylpropyl)[1,2,4]triazolo[1,5-a]pyrimidin-7-amine;
5-chloro-N-isobutyl-N-(2,2,2-trifluoroethyl)-6-(2,4,6-trifluorophenyl)[1,2,4]triazolo[1,5-a]pyrimidin-7-amine;
5-chloro-N-isobutyl-6-(2-methylphenyl)-N-(2,2,2-trifluoroethyl)[1,2,4]triazolo[1,5-a]pyrimidin-7-amine;
5-chloro-6-(2-chloro-6-fluorophenyl)-N-(2,2,2-trifluoro-1-methylethyl)[1,2,4]triazolo[1,5-a]pyrimidin-7-amine;
5-chloro-6-(2,6-difluorophenyl)-N-(2,2,2-trifluoro-1-methylethyl)[1,2,4]triazolo[1,5-a]pyrimidin-7-amine;
5-chloro-N-(2,2,2-trifluoro-1-methylethyl)-6-(2,4,6-trifluorophenyl)[1,2,4]triazolo[1,5-a]pyrimidin-7-amine;
N-allyl-5-chloro-N-isobutyl-6-(2,4,6-trifluorophenyl)[1,2,4]triazolo[1,5-a]pyrimidin-7-amine;
5-chloro-N-(1,2-dimethylpropyl)-6-(2,4,6-trifluorophenyl)[1,2,4]triazolo[1,5-a]pyrimidin-7-amine;
5-chloro-N-isopropyl-N-methyl-6-(2,4,6-trifluorophenyl)[1,2,4]triazolo[1,5-a]pyrimidin-7-amine;
5-chloro-N-isopropyl-N-(2,2,2-trifluoroethyl)-6-(2,4,6-trifluorophenyl)[1,2,4]triazolo[1,5-a]pyrimidin-7-amine;
5-chloro-N-(1-phenylethyl)-6-(2,4,6-trifluorophenyl)[1,2,4]triazolo[1,5-a]pyrimidin-7-amine;
5-chloro-6-(2-chlorophenyl)-N-(2,2,2-trifluoro-1-methylethyl)[1,2,4]triazolo[1,5-a]pyrimidin-7-amine;
5-chloro-N-ethyl-N-isobutyl-6-(2,4,6-trifluorophenyl)[1,2,4]triazolo[1,5-a]pyrimidin-7-amine;
5-chloro-6-(2-methylphenyl)-N,N-bis(2,2,2-trifluoroethyl)[1,2,4]triazolo[1,5-a]pyrimidin-7-amine;
5-chloro-N-cyclopentyl-N-methyl-6-(2,3,4,5,6-pentafluorophenyl)[1,2,4]triazolo[1,5-a]pyrimidin-7-amine;
5-chloro-N-(1,2-dimethylpropyl)-N-methyl-6-(2,3,4,5,6-pentafluorophenyl)[1,2,4]triazolo[1,5-a]pyrimidin-7-amine;
5-chloro-N-(1,2-dimethylpropyl)-N-methyl-6-(2,4,6-trifluorophenyl)[1,2,4]triazolo[1,5-a]pyrimidin-7-amine;
5-chloro-6-(2-bromo-5-chlorophenyl)-N-(2,2,2-trifluoro-1-methylethyl)[1,2,4]triazolo[1,5-a]pyrimidin-7-amine;
[5-chloro-6-(2,4,6-trifluorophenyl)-[1,2,4]triazolo[1,5-a]pyrimidin-7-yl]-(1-p-tolyl-ethyl)-amine;
[5-chloro-6-(2,4,6-trifluorophenyl)[1,2,4]triazolo[1,5-a]pyrimidin-7-yl](2,2,2-trifluoro-1-phenylethyl)-amine;
5-chloro-N-[1-(trifluoromethyl)propyl]-6-(2,4,6-trifluorophenyl)[1,2,4]triazolo[1,5-a]pyrimidin-7-amine;
[5-chloro-6-(2,4,6-trifluorophenyl)[1,2,4]triazolo[1,5-a]pyrimidin-7-yl]-(2-methyl-1-trifluoromethyl-propyl)amine;
5-chloro-N-[(1R)-2,2,2-trifluoro-1-methylethyl]-6-(2,4,6-trifluorophenyl)[1,2,4]triazolo[1,5-a]pyrimidin-7-amine;
6-(2,4-difluorophenyl)-5-chloro-N-(2,2,2-trifluoro-1-methylethyl)[1,2,4]triazolo[1,5-a]pyrimidin-7-amine;
5-chloro-6-(2,6-difluoro-4-methoxyphenyl)-N-(2,2,2-trifluoro-1-methylethyl)[1,2,4]triazolo[1,5-a]pyrimidin-7-amine;
5-chloro-6-(2,6-difluoro-4-methoxyphenyl)-N-[(1S)-2,2,2-trifluoro-1-methylethyl][1,2,4]triazolo[1,5-a]pyrimidin-7-amine;
5-chloro-6-(2,6-dichloro-4-fluorophenyl)-7-(3,3,3-trifluoropropyl)[1,2,4]triazolo[1,5-a]pyrimidin-7-amine;
N-(sec-butyl)-5-chloro-6-(2,6-dichloro-4-fluorophenyl)[1,2,4]triazolo[1,5-a]pyrimidin-7-amine;
4-{5-chloro-7-[(2,2,2-trifluoro-1-methylethyl)amino][1,2,4]triazolo[1,5-a]pyrimidin-6-yl}-3,6-difluorophenol;
5-chloro-6-(2,6-difluoro-4-methoxyphenyl)[1,2,4]triazolo[1,5-a]pyrimidin-7-amine;
5-chloro-N-cyclopentyl-6-(2,6-difluoro-4-methoxyphenyl)[1,2,4]triazolo[1,5-a]pyrimidin-7-amine;
5-chloro-6-(2,6-difluoro-4-methoxyphenyl)-N-(1,2,2-trimethylpropyl)[1,2,4]triazolo[1,5-a]pyrimidin-7-amine;

5-chloro-6-(2,6-difluoro-4-methoxyphenyl)-N-ethyl-N-(2-methyl-2-propenyl)[1,2,4]triazolo[1,5-a]pyrimidin-7-amine;
6-(4-{5-chloro-7-[(2,2,2-trifluoro-1-methylethyl)amino][1,2,4]triazolo[1,5-a]pyrimidin-6-yl}-3,5-difluorophenoxy)hexanoic acid;
2,6-difluoro-4-(2-fluoroethoxy)phenyl]-N-(2,2,2-trifluoro-1-methylethyl)[1,2,4]triazolo[1,5-a]pyrimidin-7-amine;
5-chloro-N-isopropyl-6-{2-[(trifluoromethyl)sulfanyl]phenyl}[1,2,4]triazolo[1,5-a]pyrimidin-7-amine;
5-chloro-N-[4-(trifluoromethyl)phenyl]-6-(2,4,6-trifluorophenyl)[1,2,4]triazolo[1,5-a]pyrimidin-7-amine;
5-chloro-N-(4,4,4-trifluoro-2-methylbutyl)-6-(2,4,6-trifluorophenyl)[1,2,4]triazolo[1,5-a]pyrimidin-7-amine;
4-[5-chloro-7-(2,2,2-trifluoro-1-methyl-ethylamino)[1,2,4]triazolo[1,5-a]pyrimidin-6-yl]-3,5-difluoro-phenol;
{5-chloro-6-[2,6-difluoro-4-(2,2,2-trifluoro-ethoxy)-phenyl]-[1,2,4]triazolo[1,5-a]pyrimidin-7-yl}-(2,2,2-trifluoro-1-methyl-ethyl)amine;
5-chloro-6-(2,6-difluoro-4-methoxyphenyl)-N-(2,2,2-trifluoro-1-methylethyl)[1,2,4]triazolo[1,5-a]pyrimidin-7-amine;
(5-chloro-6-{4-[2-(2-ethoxyethoxy)-ethoxy]-2,6-difluoro-phenyl}[1,2,4]triazolo[1,5a]pyrimidin-7-yl-)-(2,2,2-trifluoro-1-methylethyl)amine;
(5-chloro-6-{2,6-difluoro-4-[2-(2-methoxy-ethoxy)ethoxy]-phenyl}-[1,2,4]triazolo[1,5-a]pyrimidin-7-yl-)-(2,2,2-trifluoro-1-methylethyl)amine;
{5-chloro-6-[2,6-difluoro-4-(furan-3-ylmethoxy)phenyl][1,2,4]triazolo[1,5-a]pyrimidin-7-yl}-N-(2,2,2-trifluoro-1-methylethyl)amine;
5-chloro-6-(2,5-difluoro-4-methoxyphenyl)-N-(1,2,2-trimethylpropyl)[1,2,4]triazolo[1,5-a]pyrimidin-7-amine;
5-chloro-6-(2-fluoro-4-methoxy-6-chlorophenyl)-N-(2,2,2-trifluoro-1-methylethyl)[1,2,4]triazolo[1,5-a]pyrimidin-7-amine;
5-chloro-6-[2,6-difluoro-4-(2-fluoroethoxy)phenyl]-N-ethyl-N-(2-methyl-2-propenyl)[1,2,4]triazolo[1,5-a]pyrimidin-7-amine;
2-[2-[2-(4-{5-chloro-7-[(2,2,2-trifluoro-1-methylethyl)amino][1,2,4]triazolo[1,5-a]pyrimidin-6-yl}-3,5-difluorophenoxy)ethoxy]ethanol;
5-chloro-6-(2,3-difluoro-4-methoxyphenyl)-N-(2,2,2-trifluoro-1-methylethyl)[1,2,4]triazolo[1,5-a]pyrimidin-7-amine;
5-chloro-6-{4-(2-fluoroethoxy)-2,6-difluorphenyl}-N-(2,2,2-trifluoro-1-methylethyl)[1,2,4]triazolo[1,5-a]pyrimidin-7-amine;
5-chloro-N-(4-chlorobenzyl)-6-(2-chloro-6-fluorophenyl)[1,2,4]triazolo[1,5-a]pyrimidin-7-amine;
5-chloro-6-(2-chloro-6-fluorophenyl)-N-(1-ethylpentyl)[1,2,4]triazolo[1,5-a]pyrimidin-7-amine;
5-chloro-N-cyclopentyl-6-(2-chloro-6-fluorophenyl)[1,2,4]triazolo[1,5-a]pyrimidin-7-amine;
5-chloro-N-cyclopentyl-6-(4-methylphenyl)[1,2,4]triazolo[1,5-a]pyrimidin-7-amine;
5-chloro-N-cyclopentyl-6-(2-chlorophenyl)[1,2,4]triazolo[1,5-a]pyrimidin-7-amine;
5-chloro-N,N-diethyl-6-[4-methoxyphenyl][1,2,4]triazolo[1,5-a]pyrimidin-7-amine;
5-chloro-N,N-diethyl-6-[2,4-dichlorophenyl][1,2,4]triazolo[1,5-a]pyrimidin-7-amine;
N-bicyclo[2.2.1]hept-2-yl-5-chloro-6-(2,4-dichlorophenyl)[1,2,4]triazolo[1,5-a]pyrimidin-7-amine;
5-chloro-N-ethyl-N-(2-methyl-2-propenyl)-6-(4-(methylsulfanyl)phenyl)[1,2,4]triazolo[1,5-a]pyrimidin-7-amine;
5-chloro-6-(3,4-difluorophenyl)-N-(isopropyl)[1,2,4]triazolo[1,5-a]pyrimidin-7-amine;
5-bromo-6-(4-bromophenyl)-7-dimethylamino[1,2,4]triazolo[1,5-a]pyrimidine;
5-bromo-6-(4-trifluoromethylphenyl)-7-dimethylamino [1,2,4]triazolo[1,5-a]pyrimidine;
5-chloro-6-(3,4-difluorophenyl)-7-dimethylamino[1,2,4]triazolo[1,5-a]pyrimidine;
5-chloro-6-(4-trifluoromethylphenyl)-N-(ethyl)[1,2,4]triazolo[1,5-a]pyrimidin-7-amine;
ethyl{[5-chloro-6-(2-chloro-6-fluorophenyl)[1,2,4]triazolo[1,5-a]pyrimidin-7-yl]amino}acetate;
5-chloro-6-(2,5-difluorophenyl)-N-(3-methyl-2-butenyl)[1,2,4]triazolo[1,5-a]pyrimidin-7-amine;
5-chloro-N,N-diethyl-6-[4-(methylsulfanyl)phenyl][1,2,4]triazolo[1,5-a]pyrimidin-7-amine;
5-chloro-N-ethyl-N-(2-methyl-2-propenyl)-6-(4-phenoxyphenyl)[1,2,4]triazolo[1,5-a]pyrimidin-7-amine;
5-chloro-7-(3-nitro-4-methylanilino)-6-(2, 4, 6-trifluorophenyl)[1,2,4]triazolo[1,5-a]pyrimidine;
5-chloro-6-(2-chloro-6-fluorophenyl)-N-(3,4,5-trimethoxybenzyl)[1,2,4]triazolo[1,5-a]pyrimidin-7-amine;
N-4-[5-chloro-6-(2-chloro-6-fluorophenyl)[1,2,4]triazolo[1,5-a]pyrimidin-7-yl-N,N-1-diethyl-1,4-pentanediamine;
5-chloro-N-(3-methyl-2-butenyl)-6-phenyl[1,2,4]triazolo[1,5-a]pyrimidin-7-amine;
5-dimethylamino-6-phenyl-N-cyclopentyl[1,2,4]triazolo[1,5-a]pyrimidin-7-amine;
6-[1,1'-biphenyl]-4-yl-5-chloro-N-cyclopentyl[1,2,4]triazolo[1,5-a]pyrimidin-7-amine;
6-[4-(benzyloxy)phenyl]-5-chloro-N-isopropyl[1,2,4]triazolo[1,5-a]pyrimidin-7-amine;
5-chloro-N-[(2,2-dichlorocyclopropyl)methyl]-6-(3,4,5-trimethoxyphenyl)[1,2,4]triazolo[1,5-a]pyrimidin-7-amine;
N-cyclopentyl-6-(2-fluorophenyl)-5-hydrazino[1,2,4]triazolo[1,5-a]pyrimidin-7-amine;
5-chloro-N-ethyl-6-(2-methylphenyl)[1,2,4]triazolo[1,5-a]pyrimidin-7-amine;
6-(4-tert-butylphenyl)-5-chloro-N-isopropyl[1,2,4]triazolo[1,5-a]pyrimidin-7-amine;
5-chloro-6-[2,6-difluoro-4-[(3-methyl-2-butenyl)oxy]phenyl]-N-(2,2,2-trifluoro-1-methylethyl)-1[1,2,4]triazolo[1,5-a]pyrimidin-7-amine;
5-chloro-6-[2,6-difluoro-4-(1-propenyloxy)phenyl]-N-(2,2,2-trifluoro-1-methylethyl)-1[1,2,4]triazolo[1,5-a]pyrimidin-7-amine;
5-chloro-N-(3-tricyclo{2.2.1.0$^{2,6}$]hept-1-yl)-6-(2,4,6-trifluorophenyl)[1,2,4]triazolo[1,5-a]pyrimidin-7-amine;
or a pharmaceutically acceptable salt thereof.

14. The method according to claim 1 wherein said substituted triazolopyrimidine derivative is 5-chloro-N-[(1S)-2,2,2-trifluoro-1-methylethyl]-6-(2,4,6-trifluorophenyl [1,2,4]triazolo[1,5-a]pyrimidin-7-amine or a pharmaceutically acceptable salt thereof.

15. The method according to claim 1 wherein the cancerous tumor cells are selected from the group consisting of colon, lung, prostate, cervical, epidermal, leukemia, skin and brain.

16. The method according to claim 1 wherein the cancerous tumor cells are selected from the group consisting of lung, brain, melanoma, colon, and cervical.

* * * * *